US012567489B2

(12) United States Patent
Meirovitch et al.

(10) Patent No.: US 12,567,489 B2
(45) Date of Patent: Mar. 3, 2026

(54) SYSTEMS AND METHODS FOR DISPLAYING DISTAL FRACTIONAL FLOW RESERVE VALUES IN VASCULAR ANALYSIS

(71) Applicant: Cathworks Ltd., Kfar Saba (IL)

(72) Inventors: Hila Meirovitch, Kfar Saba (IL); Vered Anin, Kfar Saba (IL)

(73) Assignee: Cathworks Ltd., Kfar Saba (IL)

( * ) Notice: Subject to any disclaimer, the term of this patent is extended or adjusted under 35 U.S.C. 154(b) by 0 days.

(21) Appl. No.: 19/030,602

(22) Filed: Jan. 17, 2025

(65) Prior Publication Data

US 2025/0380913 A1      Dec. 18, 2025

Related U.S. Application Data

(60) Provisional application No. 63/708,477, filed on Oct. 17, 2024, provisional application No. 63/659,214, filed on Jun. 12, 2024.

(51) Int. Cl.
*G06T 17/00*          (2006.01)
*A61B 5/00*          (2006.01)
(Continued)

(52) U.S. Cl.
CPC .......... *A61B 5/7435* (2013.01); *A61B 5/0261* (2013.01); *A61B 5/743* (2013.01);
(Continued)

(58) Field of Classification Search
CPC ......... G06T 2207/30101; G06T 7/0012; G06T 2200/04; G06T 2200/24;
(Continued)

(56) References Cited

U.S. PATENT DOCUMENTS 5,150,292 A      9/1992  Hoffmann et al.
5,638,823 A      6/1997  Akay et al.
(Continued)

FOREIGN PATENT DOCUMENTS

AU          2010298333          1/2012
CN          104282009          1/2015
(Continued)

OTHER PUBLICATIONS

Abraham et al., "Alternative routes in road networks", ACM Journal of Experimental Algorithmics, Association of Computing Machinery, vol. 18(1):1.3:2-1.3:17 (2013).
(Continued)

*Primary Examiner* — Hau H Nguyen
(74) *Attorney, Agent, or Firm* — Knobbe, Martens, Olson & Bear, LLP

(57)          ABSTRACT

Systems and methods for displaying flow index values on a user interface. An example method may include receiving medical images imaging a portion of a vasculature of a subject, with the portion of the vasculature including vessels; producing, by automatic processing of the medical images, a three-dimensional vascular model of the portion of the vasculature comprising the one or more vessels based on the medical images; calculating flow index values quantifying vascular function along each of the one or more vessels based on the three-dimensional vascular model; displaying a representation of the three-dimensional vascular model comprising the one or more vessels; and for a designated vessel of the one or more vessels, simultaneously displaying the flow value index for a designated location of the designated vessel along with the flow value index for a predetermined distal location along a length of the designated vessel.

20 Claims, 15 Drawing Sheets

(51) Int. Cl.
    *A61B 5/026*       (2006.01)
    *G06T 7/00*        (2017.01)

(52) U.S. Cl.
    CPC ............ *G06T 7/0012* (2013.01); *G06T 17/00*
        (2013.01); *G06T 2200/24* (2013.01); *G06T*
        *2207/30104* (2013.01); *G06T 2210/41*
        (2013.01)

(58) Field of Classification Search
    CPC . G06T 2207/30104; G06T 2207/30172; G06T
        17/00; G06T 7/11; G06T 2210/41; A61B
        6/504; A61B 5/7475
    See application file for complete search history.

(56)              References Cited

U.S. PATENT DOCUMENTS

| | | | |
|---|---|---|---|
| 6,047,080 A | 4/2000 | Chen et al. |
| 6,186,948 B1 | 2/2001 | Kamiyama et al. |
| 6,236,878 B1 | 5/2001 | Taylor et al. |
| 6,501,848 B1 | 12/2002 | Carroll et al. |
| 6,842,638 B1 | 1/2005 | Suri et al. |
| 7,113,623 B2 | 9/2006 | Chen et al. |
| 7,339,585 B2 | 3/2008 | Verstraelen et al. |
| 7,369,691 B2 | 5/2008 | Kondo et al. |
| 7,574,026 B2 | 8/2009 | Rasche et al. |
| 7,657,299 B2 | 2/2010 | Huizenga et al. |
| 7,693,315 B2 | 4/2010 | Krishnan et al. |
| 7,738,626 B2 | 6/2010 | Weese et al. |
| 7,808,503 B2 | 10/2010 | Duluk, Jr. et al. |
| 7,860,283 B2 | 12/2010 | Begelman et al. |
| 7,864,997 B2 | 1/2011 | Aben |
| 7,912,260 B2 | 3/2011 | Breeuwer et al. |
| 7,970,187 B2 | 6/2011 | Puts et al. |
| 7,983,459 B2 | 7/2011 | Begelman et al. |
| 8,073,224 B2 | 12/2011 | Strobel et al. |
| 8,086,000 B2 | 12/2011 | Weijers et al. |
| 8,090,164 B2 | 1/2012 | Bullitt et al. |
| 8,155,411 B2 | 4/2012 | Hof et al. |
| 8,298,147 B2 | 10/2012 | Huennekens et al. |
| 8,311,748 B2 | 11/2012 | Taylor et al. |
| 8,311,750 B2 | 11/2012 | Taylor |
| 8,315,812 B2 | 11/2012 | Taylor |
| 8,321,150 B2 | 11/2012 | Taylor |
| 8,331,314 B2 | 12/2012 | Quiang et al. |
| 8,496,594 B2 | 7/2013 | Taylor et al. |
| 8,523,779 B2 | 9/2013 | Taylor et al. |
| 8,548,778 B1 | 10/2013 | Hart et al. |
| 8,554,490 B2 | 10/2013 | Tang et al. |
| 8,560,968 B1 | 10/2013 | Nair |
| 8,594,950 B2 | 11/2013 | Taylor |
| 8,715,184 B2 | 5/2014 | Lazebnik |
| 8,768,669 B1 | 7/2014 | Hart et al. |
| 8,771,195 B2 | 7/2014 | Kim et al. |
| 8,787,641 B2 | 7/2014 | Hof et al. |
| 8,812,246 B2 | 8/2014 | Taylor |
| 8,824,752 B1 | 9/2014 | Fonte et al. |
| 8,837,860 B1 | 9/2014 | Grady et al. |
| 8,861,820 B2 | 10/2014 | Fonte et al. |
| 8,917,925 B1 | 12/2014 | Grady et al. |
| 8,934,686 B2 | 1/2015 | Ostrovsky-Berman et al. |
| 8,970,578 B2 | 3/2015 | Voros et al. |
| 9,008,405 B2 | 4/2015 | Fonte et al. |
| 9,042,611 B2 | 5/2015 | Blezek et al. |
| 9,042,613 B2 | 5/2015 | Spilker et al. |
| 9,070,214 B1 | 6/2015 | Grady et al. |
| 9,078,564 B2 | 7/2015 | Taylor |
| 9,087,147 B1 | 7/2015 | Fonte |
| 9,129,418 B2 | 9/2015 | Schormans et al. |
| 9,138,147 B2 | 9/2015 | Schmitt et al. |
| 9,153,047 B1 | 10/2015 | Grady et al. |
| 9,189,600 B2 | 11/2015 | Spilker et al. |
| 9,256,936 B2 | 2/2016 | Jacobs et al. |
| 9,314,584 B1 | 4/2016 | Riley et al. |
| 9,375,191 B2 | 6/2016 | Verstraelen et al. |
| 9,406,141 B2 | 8/2016 | Kelm et al. |
| 9,430,827 B2 | 8/2016 | Kelm et al. |
| 9,466,117 B2 | 10/2016 | Habets et al. |
| 9,471,999 B2 | 10/2016 | Ishii et al. |
| 9,572,495 B2 | 2/2017 | Schmitt et al. |
| 9,576,360 B2 | 2/2017 | Schormans et al. |
| 9,613,186 B2 | 4/2017 | Fonte |
| 9,615,755 B2 | 4/2017 | Riley et al. |
| 9,633,454 B2 | 4/2017 | Lauritsch et al. |
| 9,646,361 B2 | 5/2017 | Koo et al. |
| 9,706,925 B2 | 7/2017 | Taylor |
| 9,743,835 B2 | 8/2017 | Taylor |
| 9,754,082 B2 | 9/2017 | Taylor et al. |
| 9,786,068 B2 | 10/2017 | Ishii et al. |
| 9,801,689 B2 | 10/2017 | Taylor |
| 9,805,465 B2 | 10/2017 | Kyriakou |
| 9,814,433 B2 | 11/2017 | Benishti et al. |
| 9,858,387 B2 | 1/2018 | Lavi et al. |
| 9,870,634 B2 | 1/2018 | Grady et al. |
| 9,888,896 B2 | 2/2018 | Lauritsch et al. |
| 9,934,566 B2 | 4/2018 | Sun et al. |
| 9,940,736 B2 | 4/2018 | Ishii et al. |
| 9,943,233 B2 | 4/2018 | Lavi et al. |
| 9,965,873 B2 | 5/2018 | Grady et al. |
| 9,968,256 B2 | 5/2018 | Taokowsky et al. |
| 9,977,869 B2 | 5/2018 | Lavi et al. |
| 9,999,361 B2 | 6/2018 | Sharma et al. |
| 10,141,074 B2 | 11/2018 | Lavi et al. |
| 10,143,390 B2 | 12/2018 | Ledoux et al. |
| 10,159,529 B2 | 12/2018 | Taylor |
| 10,176,575 B2 | 1/2019 | Isgum et al. |
| 10,210,956 B2 | 2/2019 | Lavi et al. |
| 10,219,704 B2 | 3/2019 | Lavi et al. |
| 10,229,516 B2 | 3/2019 | Aben et al. |
| 10,235,796 B2 | 3/2019 | Aben et al. |
| 10,245,001 B2 | 4/2019 | Redel et al. |
| 10,342,442 B2 | 7/2019 | Hattangadi et al. |
| 10,354,744 B2 | 7/2019 | Sharma et al. |
| 10,360,674 B2 | 7/2019 | Contini et al. |
| 10,363,018 B2 | 7/2019 | Fukuda et al. |
| 10,373,700 B2 | 8/2019 | Sharma et al. |
| 10,376,165 B2 | 8/2019 | Lavi et al. |
| 10,395,366 B2 | 8/2019 | Isgum et al. |
| 10,395,774 B2 | 8/2019 | Lavi et al. |
| 10,420,610 B2 | 9/2019 | Bai et al. |
| 10,424,063 B2 | 9/2019 | Lavi et al. |
| 10,441,235 B2 | 10/2019 | Lavi et al. |
| 10,441,239 B2 | 10/2019 | Abe |
| 10,456,094 B2 | 10/2019 | Fonte et al. |
| 10,463,336 B2 | 11/2019 | Itu et al. |
| 10,470,730 B2 | 11/2019 | Benishti et al. |
| 10,559,388 B2 | 2/2020 | Lavi et al. |
| 10,580,141 B2 | 3/2020 | Freiman et al. |
| 10,580,526 B2 | 3/2020 | Ma et al. |
| 10,595,807 B2 | 3/2020 | Lavi et al. |
| 10,631,737 B2 | 4/2020 | Lavi et al. |
| 10,636,146 B2 | 4/2020 | Zhong et al. |
| 10,650,522 B2 | 5/2020 | Hoi et al. |
| 10,682,180 B2 | 6/2020 | Taylor |
| 10,699,407 B2 | 6/2020 | Isgum et al. |
| 10,702,339 B2 | 7/2020 | Taylor |
| 10,733,792 B2 | 8/2020 | Aben et al. |
| 10,740,961 B2 | 8/2020 | Reiber et al. |
| 10,748,285 B2 | 8/2020 | Igarashi et al. |
| 10,758,200 B2 | 9/2020 | Passerini et al. |
| 10,776,988 B2 | 9/2020 | Grady et al. |
| 10,803,994 B2 | 10/2020 | Lavi et al. |
| 10,803,995 B2 | 10/2020 | Sharma et al. |
| 10,828,109 B2 | 11/2020 | Redel |
| 10,854,329 B2 | 12/2020 | Mohr et al. |
| 10,964,017 B2 | 3/2021 | Pack et al. |
| 10,964,071 B2 | 3/2021 | Grady et al. |
| 11,004,198 B2 | 5/2021 | Isgum et al. |
| 11,017,531 B2 | 5/2021 | Harish et al. |
| 11,031,136 B2 | 6/2021 | Grass et al. |
| 11,051,779 B2 | 7/2021 | Turca et al. |
| 11,055,845 B2 | 7/2021 | Nickisch et al. |
| 11,076,770 B2 | 8/2021 | Lavi et al. |
| 11,081,237 B2 | 8/2021 | Lavi et al. |

(56) References Cited

U.S. PATENT DOCUMENTS

| | | | |
|---|---|---|---|
| 11,083,377 B2 | 8/2021 | Bouwman et al. |
| 11,083,524 B2 | 8/2021 | Taylor |
| 11,087,884 B2 | 8/2021 | Sankaran et al. |
| 11,090,118 B2 | 8/2021 | Taylor |
| 11,116,575 B2 | 9/2021 | Taylor |
| 11,127,503 B2 | 9/2021 | Rabbat et al. |
| 11,138,733 B2 | 10/2021 | Lavi et al. |
| 11,141,123 B2 | 10/2021 | Homann et al. |
| 11,160,524 B2 | 11/2021 | Lavi et al. |
| 11,179,043 B2 | 11/2021 | Haase et al. |
| 11,185,368 B2 | 11/2021 | Spilker et al. |
| 11,195,278 B2 | 12/2021 | Nickisch et al. |
| 11,202,612 B2 | 12/2021 | Sakaguchi |
| 11,216,944 B2 | 1/2022 | Reiber et al. |
| 11,272,845 B2 | 3/2022 | Cheline et al. |
| 11,278,208 B2 | 3/2022 | Lavi et al. |
| 11,282,170 B2 | 3/2022 | Gauriau et al. |
| 11,288,811 B2 | 3/2022 | Tu et al. |
| 11,288,813 B2 | 3/2022 | Grady et al. |
| 11,295,864 B2 | 4/2022 | Benishti et al. |
| 11,298,187 B2 | 4/2022 | Taylor |
| 11,304,665 B2 | 4/2022 | Sharma et al. |
| 11,308,621 B2 | 4/2022 | Tu et al. |
| 11,328,824 B2 | 5/2022 | Fonte |
| 11,341,631 B2 | 5/2022 | Song et al. |
| 11,375,904 B2 | 7/2022 | Igarashi |
| 11,382,569 B2 | 7/2022 | Grady et al. |
| 11,389,130 B2 | 7/2022 | Itu et al. |
| 11,398,029 B2 | 7/2022 | Grady et al. |
| 11,406,337 B2 | 8/2022 | Lavi et al. |
| 11,406,339 B2 | 8/2022 | Mistretta et al. |
| 11,409,422 B2 | 8/2022 | Olivan Bescos et al. |
| 11,410,308 B2 | 8/2022 | Gulsun et al. |
| 11,423,532 B2 | 8/2022 | Takahashi et al. |
| 11,424,036 B2 | 8/2022 | Fonte et al. |
| 11,424,038 B2 | 8/2022 | Grady et al. |
| 11,443,428 B2 | 9/2022 | Petersen et al. |
| 11,445,923 B2 | 9/2022 | Tu et al. |
| 11,462,326 B2 | 10/2022 | Wang et al. |
| 11,462,329 B2 | 10/2022 | Rabbat et al. |
| 11,468,567 B2 | 10/2022 | Groth et al. |
| 11,482,339 B2 | 10/2022 | Koo et al. |
| 11,490,867 B2 | 11/2022 | Homann et al. |
| 11,494,904 B2 | 11/2022 | Fonte et al. |
| 11,495,357 B2 | 11/2022 | Ma et al. |
| 11,501,485 B2 | 11/2022 | Grady et al. |
| 11,508,460 B2 | 11/2022 | Wang et al. |
| 11,510,587 B2 | 11/2022 | Kristanto et al. |
| 11,521,755 B2 | 12/2022 | Taylor et al. |
| 11,523,744 B2 | 12/2022 | Freiman et al. |
| 11,538,161 B2 | 12/2022 | Wang et al. |
| 11,540,931 B2 | 1/2023 | Grady et al. |
| 11,557,036 B2 | 1/2023 | Liao et al. |
| 11,557,069 B2 | 1/2023 | Senzig et al. |
| 11,559,274 B2 | 1/2023 | Auvray et al. |
| 11,564,746 B2 | 1/2023 | Spilker et al. |
| 11,564,748 B2 | 1/2023 | Thienphrapa et al. |
| 11,574,406 B2 | 2/2023 | Chen et al. |
| 11,576,621 B2 | 2/2023 | Sharma et al. |
| 11,576,626 B2 | 2/2023 | Fonte et al. |
| 11,576,637 B2 | 2/2023 | Schmitt et al. |
| 11,576,639 B2 | 2/2023 | Song et al. |
| 11,583,340 B2 | 2/2023 | Taylor |
| 11,589,924 B2 | 2/2023 | Passerini et al. |
| 11,599,996 B2 | 3/2023 | Isgum et al. |
| 11,607,189 B2 | 3/2023 | Tu et al. |
| 11,610,309 B2 | 3/2023 | Kweon et al. |
| 11,610,318 B2 | 3/2023 | Grady et al. |
| 11,615,529 B2 | 3/2023 | Chitiboi |
| 11,615,894 B2 | 3/2023 | Lavi et al. |
| 11,617,620 B2 | 4/2023 | Tran et al. |
| 11,633,118 B2 | 4/2023 | Freiman et al. |
| 11,638,609 B2 | 5/2023 | Sankaran et al. |
| 11,642,171 B2 | 5/2023 | Jaquet et al. |
| 11,653,833 B2 | 5/2023 | Sanders et al. |
| 11,664,128 B2 | 5/2023 | Haase et al. |
| 11,666,236 B2 | 6/2023 | Lavi et al. |
| 11,672,434 B2 | 6/2023 | Tochterman et al. |
| 11,678,853 B2 | 6/2023 | Gulsun et al. |
| 11,678,937 B2 | 6/2023 | Choi et al. |
| 11,688,502 B2 | 6/2023 | Anderson et al. |
| 11,690,518 B2 | 7/2023 | Haase et al. |
| 11,694,339 B2 | 7/2023 | Schormans et al. |
| 11,707,196 B2 | 7/2023 | Lavi et al. |
| 11,707,242 B2 | 7/2023 | Van Walsum et al. |
| 11,710,569 B2 | 7/2023 | Grass et al. |
| 11,728,037 B2 | 8/2023 | Lavi et al. |
| 11,741,574 B2 | 8/2023 | Kweon et al. |
| 11,741,602 B2 | 8/2023 | Reiber et al. |
| 11,744,472 B2 | 9/2023 | Zhao et al. |
| 11,744,544 B2 | 9/2023 | Sheehan et al. |
| 11,748,902 B2 | 9/2023 | Bai et al. |
| 11,756,195 B2 | 9/2023 | Kweon et al. |
| 11,769,254 B2 | 9/2023 | Song et al. |
| 11,776,149 B2 | 10/2023 | Wang et al. |
| 11,779,225 B2 | 10/2023 | Adiyoso |
| 11,779,233 B2 | 10/2023 | Huo et al. |
| 11,779,294 B2 | 10/2023 | Liu et al. |
| 11,786,202 B2 | 10/2023 | Yin et al. |
| 11,793,575 B2 | 10/2023 | Taylor |
| 11,803,966 B2 | 10/2023 | Denzinger et al. |
| 11,810,290 B2 | 11/2023 | Flohr et al. |
| 11,810,661 B2 | 11/2023 | Barley et al. |
| 11,816,836 B2 | 11/2023 | Isgum et al. |
| 11,816,837 B2 | 11/2023 | Lavi et al. |
| 11,826,106 B2 | 11/2023 | Hart et al. |
| 11,826,175 B2 | 11/2023 | Itu et al. |
| 11,847,547 B2 | 12/2023 | Wang et al. |
| 11,861,825 B2 | 1/2024 | Van Pelt et al. |
| 11,861,839 B2 | 1/2024 | Weese et al. |
| 11,861,851 B2 | 1/2024 | Figueroa-Alvarez et al. |
| 11,869,142 B2 | 1/2024 | Bai et al. |
| 11,883,225 B2 | 1/2024 | Sankaran et al. |
| 11,896,416 B2 | 2/2024 | Huo et al. |
| 11,901,081 B2 | 2/2024 | Huo et al. |
| 11,918,291 B2 | 3/2024 | Grass et al. |
| 11,931,195 B2 | 3/2024 | Itu et al. |
| 11,937,963 B2 | 3/2024 | Lavi et al. |
| 11,944,387 B2 | 4/2024 | Sankaran et al. |
| 11,948,677 B2 | 4/2024 | Ghose et al. |
| 11,948,695 B2 | 4/2024 | Taylor et al. |
| 11,980,492 B2 | 5/2024 | Venugopal et al. |
| 11,983,473 B2 | 5/2024 | Aben et al. |
| 11,986,280 B2 | 5/2024 | Grady et al. |
| 11,995,834 B2 | 5/2024 | Neumann et al. |
| 12,016,635 B2 | 6/2024 | Taylor |
| 12,023,189 B2 | 7/2024 | Haase et al. |
| 12,027,253 B2 | 7/2024 | Schoebinger et al. |
| 12,029,494 B2 | 7/2024 | Taylor |
| 12,035,976 B2 | 7/2024 | Choi et al. |
| 12,039,729 B2 | 7/2024 | Kweon et al. |
| 12,042,249 B2 | 7/2024 | Haase et al. |
| 12,048,575 B2 | 7/2024 | Vaillant et al. |
| 12,051,192 B2 | 7/2024 | Aben et al. |
| 12,051,202 B2 | 7/2024 | Freiman et al. |
| 12,051,497 B2 | 7/2024 | Grady et al. |
| 12,062,198 B2 | 8/2024 | Liu et al. |
| 12,067,729 B2 | 8/2024 | Thamm et al. |
| 12,079,994 B2 | 9/2024 | Lavi et al. |
| 12,086,981 B2 | 9/2024 | Bai et al. |
| 12,089,977 B2 | 9/2024 | Isgum et al. |
| 12,094,112 B2 | 9/2024 | Gulsun et al. |
| 12,094,188 B2 | 9/2024 | Li et al. |
| 12,094,596 B2 | 9/2024 | Wang et al. |
| 12,100,174 B2 | 9/2024 | Vaillant et al. |
| 12,100,502 B2 | 9/2024 | Cimen et al. |
| 12,109,061 B2 | 10/2024 | Itu et al. |
| 12,109,065 B2 | 10/2024 | Sheehan et al. |
| 12,112,471 B2 | 10/2024 | Viti et al. |
| 12,112,483 B2 | 10/2024 | Grady et al. |
| 12,115,014 B2 | 10/2024 | Haase et al. |
| 12,118,724 B2 | 10/2024 | Van Pelt et al. |
| 12,119,117 B2 | 10/2024 | Wang et al. |
| 12,125,217 B2 | 10/2024 | Venugopal et al. |

(56) References Cited

U.S. PATENT DOCUMENTS

| | | |
|---|---|---|
| 12,125,261 B2 | 10/2024 | Petersen et al. |
| 12,131,525 B2 | 10/2024 | Groth et al. |
| 12,136,209 B2 | 11/2024 | Haase et al. |
| 12,138,026 B2 | 11/2024 | Grady et al. |
| 12,138,027 B2 | 11/2024 | Lavi et al. |
| 12,142,384 B2 | 11/2024 | Rabbat et al. |
| 12,175,631 B2 | 12/2024 | Kweon et al. |
| 12,175,669 B2 | 12/2024 | Wang et al. |
| 12,176,094 B2 | 12/2024 | Taylor et al. |
| 12,178,557 B2 | 12/2024 | Grady et al. |
| 12,186,062 B2 | 1/2025 | Fonte et al. |
| 12,190,503 B2 | 1/2025 | Denzinger et al. |
| 12,190,504 B2 | 1/2025 | Aben et al. |
| 12,193,793 B2 | 1/2025 | Bouwman et al. |
| 12,198,335 B2 | 1/2025 | Haase et al. |
| 12,207,961 B2 | 1/2025 | Liu et al. |
| 12,211,208 B2 | 1/2025 | Bruch-El et al. |
| 12,211,250 B2 | 1/2025 | Kweon et al. |
| 12,217,427 B2 | 2/2025 | Schreckenberg et al. |
| 12,217,872 B2 | 2/2025 | Lavi et al. |
| 12,229,956 B2 | 2/2025 | Kim et al. |
| 12,236,600 B2 | 2/2025 | Lavi et al. |
| 12,268,545 B2 | 4/2025 | Aben |
| 12,283,052 B2 | 4/2025 | Bhowmick et al. |
| 12,299,075 B2 | 5/2025 | Muehlberg et al. |
| 12,307,660 B2 | 5/2025 | Yang et al. |
| 12,307,672 B2 | 5/2025 | Tu et al. |
| 12,315,076 B1 | 5/2025 | Farkash et al. |
| 12,343,119 B2 | 7/2025 | Lavi et al. |
| 12,354,755 B2 | 7/2025 | Benishti et al. |
| 2003/0105401 A1 | 6/2003 | Jago et al. |
| 2004/0019264 A1 | 1/2004 | Suurmond et al. |
| 2004/0066958 A1 | 4/2004 | Chen et al. |
| 2005/0041842 A1 | 2/2005 | Frakes et al. |
| 2005/0043614 A1 | 2/2005 | Huizenga et al. |
| 2005/0249327 A1 | 11/2005 | Wink et al. |
| 2005/0272992 A1 | 12/2005 | O'Donnell et al. |
| 2006/0036167 A1 | 2/2006 | Shina |
| 2006/0074285 A1 | 4/2006 | Zarkh et al. |
| 2006/0084862 A1 | 4/2006 | Suurmond et al. |
| 2006/0098010 A1 | 5/2006 | Dwyer |
| 2007/0031019 A1 | 2/2007 | Lesage et al. |
| 2007/0167833 A1 | 7/2007 | Redel et al. |
| 2008/0020362 A1 | 1/2008 | Cotin et al. |
| 2008/0187199 A1 | 8/2008 | Gulsun et al. |
| 2008/0205722 A1 | 8/2008 | Schaefer et al. |
| 2009/0016483 A1 | 1/2009 | Kawasaki et al. |
| 2009/0016587 A1 | 1/2009 | Strobel et al. |
| 2009/0171321 A1 | 7/2009 | Callaghan |
| 2009/0299640 A1 | 12/2009 | Ellis et al. |
| 2009/0312648 A1 | 12/2009 | Zhang et al. |
| 2010/0010428 A1 | 1/2010 | Yu et al. |
| 2010/0017171 A1 | 1/2010 | Spilker et al. |
| 2010/0021025 A1 | 1/2010 | Hof et al. |
| 2010/0067760 A1 | 3/2010 | Zhang et al. |
| 2010/0125197 A1 | 5/2010 | Fishel |
| 2010/0160764 A1 | 6/2010 | Steinberg et al. |
| 2010/0160773 A1 | 6/2010 | Cohen et al. |
| 2010/0161023 A1 | 6/2010 | Cohen et al. |
| 2010/0220917 A1 | 9/2010 | Steinberg et al. |
| 2010/0239140 A1 | 9/2010 | Ruijters et al. |
| 2010/0296709 A1 | 11/2010 | Ostrovsky-Berman et al. |
| 2010/0298719 A1 | 11/2010 | Thrysoe et al. |
| 2011/0015530 A1 | 1/2011 | Misawa |
| 2011/0091377 A1 | 4/2011 | Alani et al. |
| 2011/0096907 A1 | 4/2011 | Mohamed |
| 2011/0134433 A1 | 6/2011 | Yamada |
| 2011/0135175 A1 | 6/2011 | Ostrovsky-Berman et al. |
| 2011/0142313 A1 | 6/2011 | Pack et al. |
| 2011/0182492 A1 | 7/2011 | Grass et al. |
| 2012/0014574 A1 | 1/2012 | Ferschel et al. |
| 2012/0041318 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0059249 A1 | 3/2012 | Verard et al. |
| 2012/0062841 A1 | 3/2012 | Stetson et al. |
| 2012/0072190 A1 | 3/2012 | Sharma et al. |
| 2012/0075284 A1 | 3/2012 | Rivers et al. |
| 2012/0150048 A1 | 6/2012 | Kang et al. |
| 2012/0177275 A1 | 7/2012 | Suri |
| 2012/0230565 A1 | 9/2012 | Steinberg et al. |
| 2012/0236032 A1 | 9/2012 | Arvidsson |
| 2012/0243761 A1 | 9/2012 | Senzig et al. |
| 2013/0028490 A1 | 1/2013 | Kim et al. |
| 2013/0054214 A1 | 2/2013 | Taylor |
| 2013/0060133 A1 | 3/2013 | Kassab et al. |
| 2013/0094745 A1 | 4/2013 | Sundar |
| 2013/0158476 A1 | 6/2013 | Olson |
| 2013/0182936 A1 | 7/2013 | Yoshihara et al. |
| 2013/0202170 A1 | 8/2013 | Blezek et al. |
| 2013/0226003 A1 | 8/2013 | Edic et al. |
| 2013/0229621 A1 | 9/2013 | Stetson et al. |
| 2013/0324842 A1 | 12/2013 | Mittal et al. |
| 2014/0005535 A1 | 1/2014 | Edic et al. |
| 2014/0046642 A1 | 2/2014 | Hart et al. |
| 2014/0086461 A1 | 3/2014 | Yao et al. |
| 2014/0094693 A1 | 4/2014 | Cohen et al. |
| 2014/0094697 A1 | 4/2014 | Petroff et al. |
| 2014/0100451 A1 | 4/2014 | Tolkowsky et al. |
| 2014/0121513 A1 | 5/2014 | Tolkowsky et al. |
| 2014/0142398 A1 | 5/2014 | Patil et al. |
| 2014/0180035 A1 | 6/2014 | Anderson |
| 2014/0187920 A1* | 7/2014 | Millett .................. A61B 6/504 |
| | | 600/424 |
| 2014/0200867 A1 | 7/2014 | Lavi et al. |
| 2014/0249790 A1 | 9/2014 | Spilker et al. |
| 2014/0270442 A1 | 9/2014 | Jung |
| 2014/0303495 A1 | 10/2014 | Fonte et al. |
| 2014/0371578 A1 | 12/2014 | Auvray et al. |
| 2015/0092999 A1 | 4/2015 | Schmitt et al. |
| 2015/0201897 A1 | 7/2015 | Kyriakou |
| 2015/0213600 A1 | 7/2015 | Kyriakou |
| 2015/0250395 A1 | 9/2015 | Igarashi |
| 2015/0265162 A1 | 9/2015 | Lavi et al. |
| 2015/0265222 A1 | 9/2015 | Sakaguchi |
| 2015/0297373 A1 | 10/2015 | Schmitt et al. |
| 2015/0302578 A1 | 10/2015 | Grady et al. |
| 2015/0335304 A1 | 11/2015 | Lavi et al. |
| 2015/0339847 A1 | 11/2015 | Benishti et al. |
| 2015/0342551 A1 | 12/2015 | Lavi et al. |
| 2015/0374243 A1 | 12/2015 | Itu et al. |
| 2016/0007945 A1 | 1/2016 | Taylor |
| 2016/0015349 A1 | 1/2016 | Ohuchi et al. |
| 2016/0022371 A1 | 1/2016 | Sauer et al. |
| 2016/0035088 A1 | 2/2016 | Abramoff et al. |
| 2016/0035103 A1 | 2/2016 | Stawiaski et al. |
| 2016/0073928 A1 | 3/2016 | Soper et al. |
| 2016/0110866 A1 | 4/2016 | Taylor |
| 2016/0110867 A1 | 4/2016 | Taylor |
| 2016/0128661 A1 | 5/2016 | Taylor |
| 2016/0157802 A1 | 6/2016 | Anderson |
| 2016/0157808 A1 | 6/2016 | Merritt et al. |
| 2016/0228000 A1 | 8/2016 | Spaide |
| 2016/0247279 A1 | 8/2016 | Lavi et al. |
| 2016/0371456 A1 | 12/2016 | Taylor et al. |
| 2017/0018116 A1 | 1/2017 | Sun et al. |
| 2017/0039736 A1 | 2/2017 | Aben et al. |
| 2017/0161897 A1 | 6/2017 | Hoffmann et al. |
| 2017/0224418 A1 | 8/2017 | Boettner et al. |
| 2017/0238904 A1 | 8/2017 | Perrey |
| 2017/0258433 A1 | 9/2017 | Gulsun et al. |
| 2017/0286628 A1 | 10/2017 | Shim |
| 2017/0325770 A1 | 11/2017 | Edic et al. |
| 2018/0032653 A1 | 2/2018 | Aben et al. |
| 2018/0033192 A1 | 2/2018 | deVaan et al. |
| 2018/0075221 A1 | 3/2018 | Vergaro et al. |
| 2018/0089829 A1 | 3/2018 | Zhong et al. |
| 2018/0102189 A1 | 4/2018 | Hosoi et al. |
| 2018/0182096 A1 | 6/2018 | Grady et al. |
| 2018/0211386 A1 | 7/2018 | Ma et al. |
| 2018/0235561 A1 | 8/2018 | Lavi et al. |

(56) References Cited

U.S. PATENT DOCUMENTS

| | | |
|---|---|---|
| 2018/0243033 A1 | 8/2018 | Tran et al. |
| 2018/0268941 A1* | 9/2018 | Lavi .................... A61B 5/1075 |
| 2018/0271614 A1 | 9/2018 | Kunio |
| 2018/0280088 A1 | 10/2018 | Davies |
| 2018/0315193 A1 | 11/2018 | Paschalakis et al. |
| 2018/0330507 A1 | 11/2018 | Schormans et al. |
| 2018/0344173 A1 | 12/2018 | Tu et al. |
| 2018/0344174 A9 | 12/2018 | Schmitt et al. |
| 2019/0005737 A1 | 1/2019 | Auvray et al. |
| 2019/0019347 A1 | 1/2019 | Auvray et al. |
| 2019/0038356 A1* | 2/2019 | Schmitt .................... G06T 7/60 |
| 2019/0130578 A1 | 5/2019 | Gulsun et al. |
| 2019/0156159 A1 | 5/2019 | Kopparapu |
| 2019/0172205 A1 | 6/2019 | Mao et al. |
| 2019/0180880 A1 | 6/2019 | Lavi et al. |
| 2019/0282199 A1 | 9/2019 | Merritt |
| 2019/0362494 A1 | 11/2019 | Wang et al. |
| 2019/0380593 A1 | 12/2019 | Bouwman et al. |
| 2020/0126229 A1 | 4/2020 | Lavi et al. |
| 2020/0138521 A1 | 5/2020 | Aben et al. |
| 2020/0143526 A1 | 5/2020 | Wang et al. |
| 2020/0160509 A1 | 5/2020 | Pack et al. |
| 2020/0222018 A1 | 7/2020 | van Walsum et al. |
| 2020/0226422 A1 | 7/2020 | Li et al. |
| 2020/0265958 A1 | 8/2020 | Haase et al. |
| 2020/0337664 A1 | 10/2020 | Homann et al. |
| 2020/0349708 A1 | 11/2020 | Igarashi et al. |
| 2020/0380493 A1 | 12/2020 | Morales et al. |
| 2020/0388363 A1 | 12/2020 | Docktor et al. |
| 2020/0394795 A1 | 12/2020 | Isgum et al. |
| 2021/0022617 A1 | 1/2021 | Zhao et al. |
| 2021/0035290 A1 | 2/2021 | Aben et al. |
| 2021/0042927 A1 | 2/2021 | Amis et al. |
| 2021/0085397 A1 | 3/2021 | Passerini et al. |
| 2021/0209757 A1 | 7/2021 | Min et al. |
| 2021/0244293 A1 | 8/2021 | Belleville |
| 2021/0244299 A1* | 8/2021 | Tochterman ........... A61B 6/463 |
| 2021/0244475 A1 | 8/2021 | Taylor |
| 2021/0259559 A1 | 8/2021 | Tu et al. |
| 2021/0267690 A1 | 9/2021 | Taylor |
| 2021/0272030 A1 | 9/2021 | Sankaran et al. |
| 2021/0275124 A1 | 9/2021 | Huo et al. |
| 2021/0280318 A1 | 9/2021 | Huo et al. |
| 2021/0282731 A1 | 9/2021 | Vaillant et al. |
| 2021/0282860 A1 | 9/2021 | Taylor |
| 2021/0290308 A1 | 9/2021 | Mihalef et al. |
| 2021/0298706 A1 | 9/2021 | Tu et al. |
| 2021/0298708 A1 | 9/2021 | Aben et al. |
| 2021/0334963 A1 | 10/2021 | Isgum et al. |
| 2021/0338088 A1 | 11/2021 | Bouwman et al. |
| 2021/0345889 A1 | 11/2021 | Tu et al. |
| 2021/0358634 A1 | 11/2021 | Sankaran et al. |
| 2021/0361176 A1 | 11/2021 | Huo et al. |
| 2021/0374950 A1 | 12/2021 | Gao et al. |
| 2021/0383539 A1 | 12/2021 | Haase et al. |
| 2021/0401400 A1 | 12/2021 | Sheehan et al. |
| 2022/0012876 A1 | 1/2022 | Sommer et al. |
| 2022/0012878 A1 | 1/2022 | Aoyama |
| 2022/0015730 A1 | 1/2022 | Haase et al. |
| 2022/0036646 A1 | 2/2022 | Song et al. |
| 2022/0039769 A1 | 2/2022 | M et al. |
| 2022/0054022 A1 | 2/2022 | Van Lavieren et al. |
| 2022/0079455 A1 | 3/2022 | Haase et al. |
| 2022/0079540 A1 | 3/2022 | Sankaran et al. |
| 2022/0079563 A1 | 3/2022 | Kemp |
| 2022/0087544 A1 | 3/2022 | Schmitt et al. |
| 2022/0092775 A1 | 3/2022 | Denzinger et al. |
| 2022/0092784 A1 | 3/2022 | Tu et al. |
| 2022/0101535 A1 | 3/2022 | Thamm et al. |
| 2022/0110687 A1 | 4/2022 | Spilker et al. |
| 2022/0125398 A1 | 4/2022 | Aben |
| 2022/0151580 A1 | 5/2022 | Itu et al. |
| 2022/0156918 A1 | 5/2022 | Chitiboi et al. |
| 2022/0164950 A1 | 5/2022 | Aben et al. |
| 2022/0164953 A1 | 5/2022 | Gulsun et al. |
| 2022/0167938 A1 | 6/2022 | Grass et al. |
| 2022/0172368 A1 | 6/2022 | Lavi et al. |
| 2022/0175260 A1 | 6/2022 | Sonck et al. |
| 2022/0183655 A1 | 6/2022 | Huang et al. |
| 2022/0211280 A1 | 7/2022 | Lavi et al. |
| 2022/0211439 A1 | 7/2022 | Sankaran et al. |
| 2022/0215534 A1 | 7/2022 | Bai et al. |
| 2022/0230312 A1 | 7/2022 | Choi et al. |
| 2022/0233081 A1 | 7/2022 | Cheline et al. |
| 2022/0254028 A1 | 8/2022 | Liu et al. |
| 2022/0254131 A1 | 8/2022 | Lavi et al. |
| 2022/0261997 A1 | 8/2022 | Liu et al. |
| 2022/0262000 A1 | 8/2022 | Haase et al. |
| 2022/0273180 A1 | 9/2022 | Lavi et al. |
| 2022/0277447 A1 | 9/2022 | Wang et al. |
| 2022/0287668 A1 | 9/2022 | Gulsun et al. |
| 2022/0301156 A1 | 9/2022 | Fang et al. |
| 2022/0310265 A1 | 9/2022 | Benishti et al. |
| 2022/0319004 A1 | 10/2022 | Bruch-el et al. |
| 2022/0319116 A1 | 10/2022 | Wang et al. |
| 2022/0335612 A1 | 10/2022 | Bruch-El et al. |
| 2022/0344033 A1 | 10/2022 | Wang et al. |
| 2022/0351369 A1 | 11/2022 | Haase et al. |
| 2022/0359063 A1 | 11/2022 | Tombropoulos et al. |
| 2022/0374807 A1 | 11/2022 | Mahmood |
| 2022/0378383 A1 | 12/2022 | Chen et al. |
| 2022/0392076 A1 | 12/2022 | Seo |
| 2022/0392616 A1 | 12/2022 | Ghose et al. |
| 2022/0415510 A1 | 12/2022 | Wang et al. |
| 2023/0005113 A1 | 1/2023 | Li et al. |
| 2023/0028300 A1 | 1/2023 | Lichy et al. |
| 2023/0037338 A1 | 2/2023 | Wang et al. |
| 2023/0038364 A1 | 2/2023 | Bhowmick et al. |
| 2023/0052595 A1 | 2/2023 | Langoju et al. |
| 2023/0071558 A1 | 3/2023 | Vaidya et al. |
| 2023/0084748 A1 | 3/2023 | Lavi et al. |
| 2023/0086196 A1 | 3/2023 | Chitiboi et al. |
| 2023/0095242 A1 | 3/2023 | Liu et al. |
| 2023/0097133 A1 | 3/2023 | Bai et al. |
| 2023/0097267 A1 | 3/2023 | Schwemmer et al. |
| 2023/0102646 A1 | 3/2023 | Birkhold et al. |
| 2023/0108647 A1 | 4/2023 | Tu et al. |
| 2023/0113721 A1 | 4/2023 | Kassel et al. |
| 2023/0117179 A1 | 4/2023 | Jule et al. |
| 2023/0142152 A1 | 5/2023 | Venugopal et al. |
| 2023/0142219 A1 | 5/2023 | Makino |
| 2023/0144624 A1 | 5/2023 | Venugopal et al. |
| 2023/0144795 A1 | 5/2023 | Wang et al. |
| 2023/0148977 A1 | 5/2023 | Fonte et al. |
| 2023/0177677 A1 | 6/2023 | Yuan et al. |
| 2023/0186472 A1 | 6/2023 | Kweon et al. |
| 2023/0196582 A1 | 6/2023 | Grady et al. |
| 2023/0197286 A1 | 6/2023 | Grady et al. |
| 2023/0230235 A1 | 7/2023 | Isgum et al. |
| 2023/0237648 A1 | 7/2023 | Gulsun et al. |
| 2023/0237652 A1 | 7/2023 | Flexman et al. |
| 2023/0245301 A1 | 8/2023 | Wang et al. |
| 2023/0252628 A1 | 8/2023 | Haase et al. |
| 2023/0252632 A1 | 8/2023 | Shalhon Livne et al. |
| 2023/0260107 A1 | 8/2023 | Dhatt et al. |
| 2023/0263401 A1 | 8/2023 | Escaned-Barbosa et al. |
| 2023/0277247 A1 | 9/2023 | Taylor et al. |
| 2023/0298176 A1 | 9/2023 | Choi et al. |
| 2023/0298180 A1 | 9/2023 | Kweon et al. |
| 2023/0307144 A1 | 9/2023 | He et al. |
| 2023/0309943 A1 | 10/2023 | van Walsum et al. |
| 2023/0320789 A1 | 10/2023 | Bai et al. |
| 2023/0326127 A1 | 10/2023 | Zhong et al. |
| 2023/0334659 A1 | 10/2023 | Kuo et al. |
| 2023/0352152 A1 | 11/2023 | Grady et al. |
| 2023/0355107 A1 | 11/2023 | Haase et al. |
| 2023/0355196 A1 | 11/2023 | Kang et al. |
| 2023/0355197 A1 | 11/2023 | Florent et al. |
| 2023/0360803 A1 | 11/2023 | Sankaran et al. |
| 2023/0368378 A1 | 11/2023 | Kim et al. |
| 2023/0368878 A1 | 11/2023 | Molenda |
| 2023/0386037 A1 | 11/2023 | Denzinger et al. |
| 2023/0394654 A1 | 12/2023 | Hampe et al. |
| 2023/0404525 A1 | 12/2023 | Sheehan et al. |

(56) References Cited

U.S. PATENT DOCUMENTS

| | | |
|---|---|---|
| 2023/0410307 A1 | 12/2023 | Nickisch et al. |
| 2024/0029529 A1 | 1/2024 | Scalisi |
| 2024/0029868 A1 | 1/2024 | Gulsun et al. |
| 2024/0046465 A1 | 2/2024 | Sharma et al. |
| 2024/0047043 A1 | 2/2024 | Flexman et al. |
| 2024/0050159 A1 | 2/2024 | Hart et al. |
| 2024/0065772 A1 | 2/2024 | Levi et al. |
| 2024/0078676 A1 | 3/2024 | Van Pelt et al. |
| 2024/0096479 A1 | 3/2024 | Kraus et al. |
| 2024/0099589 A1 | 3/2024 | Lavi et al. |
| 2024/0099683 A1 | 3/2024 | Cimen et al. |
| 2024/0104719 A1 | 3/2024 | Gulsun et al. |
| 2024/0126958 A1 | 4/2024 | Aben et al. |
| 2024/0130674 A1 | 4/2024 | Sonck et al. |
| 2024/0130796 A1 | 4/2024 | Song et al. |
| 2024/0164865 A1 | 5/2024 | Kottenstette et al. |
| 2024/0169540 A1 | 5/2024 | Bouwman et al. |
| 2024/0185485 A1 | 6/2024 | Salomon et al. |
| 2024/0185509 A1 | 6/2024 | Kovler et al. |
| 2024/0206838 A1 | 6/2024 | Lavi et al. |
| 2024/0212159 A1 | 6/2024 | Katzmann et al. |
| 2024/0215937 A1 | 7/2024 | Itu et al. |
| 2024/0221355 A1 | 7/2024 | Kweon et al. |
| 2024/0260919 A1 | 8/2024 | Venugopal et al. |
| 2024/0273723 A1 | 8/2024 | Tison et al. |
| 2024/0315777 A1 | 9/2024 | Choi et al. |
| 2024/0324870 A1 | 10/2024 | Wong |
| 2024/0346644 A1 | 10/2024 | Venugopal |
| 2024/0346648 A1 | 10/2024 | Kim et al. |
| 2024/0366409 A1 | 11/2024 | Xiang et al. |
| 2024/0374148 A1 | 11/2024 | Haase et al. |
| 2024/0386547 A1 | 11/2024 | Nadakuditi et al. |
| 2024/0386652 A1 | 11/2024 | Grady et al. |
| 2024/0387045 A1 | 11/2024 | Lynch et al. |
| 2024/0394875 A1 | 11/2024 | Van Der Horst et al. |
| 2024/0394996 A1 | 11/2024 | Hitschrich et al. |
| 2024/0404031 A1 | 12/2024 | Auvray et al. |
| 2024/0404057 A1 | 12/2024 | Florent et al. |
| 2024/0407656 A1 | 12/2024 | This et al. |
| 2024/0412365 A1 | 12/2024 | Kim |
| 2024/0420331 A1 | 12/2024 | Kim et al. |
| 2024/0423575 A1 | 12/2024 | Itu et al. |
| 2024/0428477 A1 | 12/2024 | Salehi et al. |
| 2025/0022133 A1 | 1/2025 | Wissel et al. |
| 2025/0032079 A1 | 1/2025 | Gomez et al. |
| 2025/0054628 A1 | 2/2025 | Anin et al. |
| 2025/0069347 A1 | 2/2025 | Lavi et al. |
| 2025/0072971 A1 | 3/2025 | Jeong et al. |
| 2025/0072972 A1 | 3/2025 | Won et al. |
| 2025/0078261 A1 | 3/2025 | DePaoli et al. |
| 2025/0078268 A1 | 3/2025 | Kim et al. |
| 2025/0078288 A1 | 3/2025 | Pedrizzetti et al. |
| 2025/0082218 A1 | 3/2025 | Fonte et al. |
| 2025/0086794 A1 | 3/2025 | Aben et al. |
| 2025/0090032 A1 | 3/2025 | Bouwman et al. |
| 2025/0090034 A1 | 3/2025 | Grady et al. |
| 2025/0099060 A1 | 3/2025 | Turcea et al. |
| 2025/0104228 A1 | 3/2025 | Neumann et al. |
| 2025/0117941 A1 | 4/2025 | Bruch-El et al. |
| 2025/0124578 A1 | 4/2025 | Kim et al. |
| 2025/0127473 A1 | 4/2025 | Ku |
| 2025/0131567 A1 | 4/2025 | Kitslaar et al. |
| 2025/0131568 A1 | 4/2025 | Lavi et al. |
| 2025/0138709 A1 | 5/2025 | Boucneau et al. |
| 2025/0139779 A1 | 5/2025 | Won et al. |
| 2025/0157032 A1 | 5/2025 | Kim et al. |
| 2025/0166177 A1 | 5/2025 | Kwon et al. |
| 2025/0166196 A1 | 5/2025 | Lavi et al. |
| 2025/0166843 A1 | 5/2025 | Lavi et al. |

FOREIGN PATENT DOCUMENTS

| | | |
|---|---|---|
| CN | 113837985 | 12/2021 |
| CN | 113935976 | 1/2022 |
| EP | 1396274 | 3/2004 |
| EP | 2163272 | 3/2010 |
| EP | 2633815 A1 | 9/2013 |
| EP | 2779907 | 9/2014 |
| EP | 2873371 | 5/2015 |
| EP | 3125764 | 2/2017 |
| EP | 2633815 B1 | 6/2017 |
| EP | 3363350 | 8/2018 |
| EP | 2977922 | 3/2019 |
| EP | 3460688 | 3/2019 |
| EP | 3477551 | 5/2019 |
| EP | 3763285 | 1/2021 |
| EP | 3847956 | 7/2021 |
| EP | 2776960 | 9/2021 |
| EP | 3534372 | 9/2021 |
| EP | 3871184 | 9/2021 |
| EP | 3881758 | 9/2021 |
| EP | 3884868 | 9/2021 |
| EP | 3282380 | 11/2021 |
| EP | 3282381 | 11/2021 |
| EP | 3903672 | 11/2021 |
| EP | 3912139 | 11/2021 |
| EP | 3664026 | 2/2022 |
| EP | 3945469 | 2/2022 |
| EP | 3949860 | 2/2022 |
| EP | 3951705 | 2/2022 |
| EP | 3076854 | 4/2022 |
| EP | 3979259 | 4/2022 |
| EP | 3982324 | 4/2022 |
| EP | 3258446 | 5/2022 |
| EP | 4002288 | 5/2022 |
| EP | 4026143 | 7/2022 |
| EP | 4026491 | 7/2022 |
| EP | 4026492 | 7/2022 |
| EP | 4029438 | 7/2022 |
| EP | 3298959 | 9/2022 |
| EP | 3989828 | 11/2022 |
| EP | 3157411 | 12/2022 |
| EP | 3606437 | 12/2022 |
| EP | 4104765 | 12/2022 |
| EP | 4113434 | 1/2023 |
| EP | 4131150 | 2/2023 |
| EP | 4137053 | 2/2023 |
| EP | 4145391 | 3/2023 |
| EP | 4156112 | 3/2023 |
| EP | 3169237 | 4/2023 |
| EP | 4160528 | 4/2023 |
| EP | 4160543 | 4/2023 |
| EP | 4170579 | 4/2023 |
| EP | 4186417 | 5/2023 |
| EP | 3403582 | 6/2023 |
| EP | 3743883 | 6/2023 |
| EP | 3989832 | 8/2023 |
| EP | 4220553 | 8/2023 |
| EP | 4224416 | 8/2023 |
| EP | 3652747 | 9/2023 |
| EP | 4104766 | 9/2023 |
| EP | 4238500 | 9/2023 |
| EP | 3602485 | 10/2023 |
| EP | 4064181 | 11/2023 |
| EP | 3602487 | 12/2023 |
| EP | 4300419 | 1/2024 |
| EP | 4312184 | 1/2024 |
| EP | 3404667 | 2/2024 |
| EP | 3878366 | 4/2024 |
| EP | 3457413 | 5/2024 |
| EP | 4005472 | 5/2024 |
| EP | 4369290 | 5/2024 |
| EP | 4176814 | 7/2024 |
| EP | 4413927 | 8/2024 |
| EP | 4418206 | 8/2024 |
| EP | 3846176 | 9/2024 |
| EP | 3881758 B1 | 9/2024 |
| EP | 3564963 | 10/2024 |
| EP | 4056110 | 10/2024 |
| EP | 4439476 | 10/2024 |
| EP | 3644857 | 2/2025 |
| EP | 4548838 | 5/2025 |
| EP | 4555935 | 5/2025 |
| JP | H07-271976 | 10/1995 |

(56) References Cited

FOREIGN PATENT DOCUMENTS

| | | |
|---|---|---|
| JP | H08-131429 | 5/1996 |
| JP | 2003-508152 | 3/2003 |
| JP | 2003-514600 | 4/2003 |
| JP | 2004-243117 | 9/2004 |
| JP | 2007-502644 | 2/2007 |
| JP | 2007-325920 | 12/2007 |
| JP | 4177217 B2 | 11/2008 |
| JP | 2010-042247 | 2/2010 |
| JP | 2011-212314 | 10/2011 |
| JP | 2012-043498 | 3/2012 |
| JP | 2013-090799 | 5/2013 |
| JP | 2010-505493 | 7/2013 |
| JP | 2013-534154 | 9/2013 |
| JP | 2014-064915 | 4/2014 |
| JP | 2014-128631 | 7/2014 |
| JP | 2014-198241 | 10/2014 |
| JP | 2015-527901 | 9/2015 |
| JP | 2017-516535 | 6/2017 |
| JP | 2018-057835 | 4/2018 |
| JP | 2018-089364 | 6/2018 |
| NL | 2012324 | 8/2015 |
| WO | WO 2001/21057 | 3/2001 |
| WO | WO 2007/066249 | 6/2007 |
| WO | WO 2010/033971 | 3/2010 |
| WO | WO 2011/038044 | 3/2011 |
| WO | WO 2011/039685 | 4/2011 |
| WO | WO 2012/021037 | 2/2012 |
| WO | WO 2012/021307 | 2/2012 |
| WO | WO 2012/043498 | 4/2012 |
| WO | WO 2012/173697 | 12/2012 |
| WO | WO 2013/102880 | 7/2013 |
| WO | WO 2014/027692 | 2/2014 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/017420 | 2/2015 |
| WO | WO 2015/059706 | 4/2015 |
| WO | WO 2016/135330 | 9/2016 |
| WO | WO 2016/161356 | 10/2016 |
| WO | WO 2017/056007 | 4/2017 |
| WO | WO 2017/199245 | 11/2017 |
| WO | WO 2017/199246 | 11/2017 |
| WO | WO 2017/200381 | 11/2017 |
| WO | WO 2018/060529 | 4/2018 |
| WO | WO 2018/165478 | 9/2018 |
| WO | WO 2018/178272 | 10/2018 |
| WO | WO 2018/184779 | 10/2018 |
| WO | WO 2019/002510 | 1/2019 |
| WO | WO 2019/101630 | 5/2019 |
| WO | WO 2020/053099 | 3/2020 |
| WO | WO 2020/084101 | 4/2020 |
| WO | WO 2020/201942 | 10/2020 |
| WO | WO 2020/212459 | 10/2020 |
| WO | WO 2021/016071 | 1/2021 |
| WO | WO 2021/059165 | 4/2021 |
| WO | WO 2021/144230 | 7/2021 |
| WO | WO 2021/175039 | 9/2021 |
| WO | WO 2021/191909 | 9/2021 |
| WO | WO 2021/221949 | 11/2021 |
| WO | WO 2021/258835 | 12/2021 |
| WO | WO 2022/000727 | 1/2022 |
| WO | WO 2022/000729 | 1/2022 |
| WO | WO 2022/000733 | 1/2022 |
| WO | WO 2022/000734 | 1/2022 |
| WO | WO 2022/000976 | 1/2022 |
| WO | WO 2022/000977 | 1/2022 |
| WO | WO 2022/002765 | 1/2022 |
| WO | WO 2022/019765 | 1/2022 |
| WO | WO 2022/069208 | 4/2022 |
| WO | WO 2022/086326 | 4/2022 |
| WO | WO 2022/109902 | 6/2022 |
| WO | WO 2022/109903 | 6/2022 |
| WO | WO 2022/109904 | 6/2022 |
| WO | WO 2022/109907 | 6/2022 |
| WO | WO 2022/136043 | 6/2022 |
| WO | WO 2022/161239 | 8/2022 |
| WO | WO 2022/167940 | 8/2022 |
| WO | WO 2022/184736 | 9/2022 |
| WO | WO 2022/199238 | 9/2022 |
| WO | WO 2022/235162 | 11/2022 |
| WO | WO 2022/261641 | 12/2022 |
| WO | WO 2023/277283 | 1/2023 |
| WO | WO 2023/057296 | 4/2023 |
| WO | WO 2023/099144 | 6/2023 |
| WO | WO 2023/104538 | 6/2023 |
| WO | WO 2023/115576 | 6/2023 |
| WO | WO 2023/146401 | 8/2023 |
| WO | WO 2023/152688 | 8/2023 |
| WO | WO 2023/191380 | 10/2023 |
| WO | WO 2023/224369 | 11/2023 |
| WO | WO 2022/228464 | 12/2023 |
| WO | WO 2024/022809 | 2/2024 |
| WO | WO 2024/023048 | 2/2024 |
| WO | WO 2024/034748 | 2/2024 |
| WO | WO 2024/074309 | 4/2024 |
| WO | WO 2024/083538 | 4/2024 |
| WO | WO 2024/121060 | 6/2024 |
| WO | WO 2024/151926 | 7/2024 |
| WO | WO 2024/156859 | 8/2024 |
| WO | WO 2024/160583 | 8/2024 |
| WO | WO 2024/177428 | 8/2024 |
| WO | WO 2024/200348 | 10/2024 |
| WO | WO 2024/230129 | 11/2024 |
| WO | WO 2024/240737 | 11/2024 |
| WO | WO 2024/244323 | 12/2024 |
| WO | WO 2024/254971 | 12/2024 |
| WO | WO 2024/238747 | 1/2025 |
| WO | WO 2025/002905 | 1/2025 |
| WO | WO 2025/023995 | 1/2025 |
| WO | WO 2025/032545 | 2/2025 |
| WO | WO 2025/032546 | 2/2025 |
| WO | WO 2025/039396 | 2/2025 |
| WO | WO 2025/042123 | 2/2025 |
| WO | WO 2025/044005 | 3/2025 |
| WO | WO 2025/055208 | 3/2025 |
| WO | WO 2025/060217 | 3/2025 |

OTHER PUBLICATIONS

Andriotis et al., "A new method of three-dimensional coronary artery reconstruction from X-Ray angiography: Validation against a virtual phantom and multislice computed tomography", Catheterization and Cardiovascular Interventions, vol. 71:28-43 (2008).

Barnea, "Model-based estimation of coronary vessel diameter in angiographic images", Proceedings of the 20th Annual International Conference of the IEEE Engineering in Medicine and Biology Society, vol. 20:513-516 (1998).

Barratt et al., "Reconstruction and quantification of the carotid artery bifurcation from 3-D ultrasound images", IEEE Transactions on Medical Imaging, vol. 23(5):567-583 (2004).

Barrett et al., "Interactive live-wire 1-3 boundary extraction", Medical Image Analysis, Oxford University Press, vol. 1(4):331-341 (1997).

Bullitt et al., "Determining malignancy of brain tumors by analysis of vessel shape", Medical Image Computing and Computer-Assisted Intervention, MICCAI 2004 Conference Proceedings, Lecture notes in Computer Science, LNCS, 3217:645-653 (2004).

Caiati et al., "New noninvasive method for coronary flow reserve assessment: Contrast-enhanced transthoracic second harmonic echo doppler", Circulation, vol. 99:771-778 (1999).

Caiati et al., "Detection, location, and severity assessment of left anterior descneding coronary artery stenoses by means of contrast-enhanced transthoracic harmonic echo dopper", European Heart Journal, vol. 30:1797-1806 (2009).

Chen et al., "3-D reconstruction of coronary arterial tree to optimize angiographic visualization", IEEE Transactions on Medical Imaging, vol. 19(4):318-336 (2000).

Chung, "Image segmentation methods for detecting blood vessels in angiography", 2006 9th International Conference on Control, Automation, Robotics and Vision, Singapore, pp. 1-6 (2006).

(56) References Cited

OTHER PUBLICATIONS

Dickie et al., "Live-vessel: interactive vascular image segmentation with simultaneous extraction of optimal medial and boundary paths", Technical Report TR 2009-23, School of Computing Science, Simon Fraser University, Burnaby, BC, Canada, Nov. 2009.

Frangi et al., "Multiscale vessel and enhancement filtering", Medical Image Computing and Computer- Assisted Intervention, MICCA '98 Lecture Notes in Computer Science, vol. 1496:130-137 (1998).

Fraz, "Blood vessel segmentation methodologies, in retinal images—a survey", Computer Methods and Programs in Biomedicine, vol. 108:407-433 (2012).

Fusejima, "Noninvasive measurement of coronary artery blood flow using combined two-dimensional and doppler echocardiography", JACC vol. 10(5):1024-1031 (1987).

Google Maps Tips 10: Drag-and-Drop Alter Your Directions, Feb. 18, 2015, XP093093278, retrieved from the internet: https://www.youtube.com/watch?v=8pYqjiZh6gw, retrieved on Oct. 19, 2023.

Hawkes et al., "Validation of volume blood flow measurements using three-dimensional distance-concentration functions detived from digital X-Ray angiograms", Investigative Radiology, vol. 29(4):434-442 (1994).

Hoffmann et al., "Determination of instantaneous and average blood flow rates from digital angiograms of vessel phantoms using distance-density curves", Investigative Radiology, vol. 26(3):207-212 (1991).

Holdsworth et al., "Quantitative angiographic blood-flow measurement using pulsed intra-arterial injection", Medical Physics, vol. 26(10):2168-2175 (1999).

Huo et al., "Intraspecific scaling laws of vascular trees", J.R. Soc. Interface vol. 9:190-200 (2012).

Hwang et al., "Diagnostic performance of resting and hyperemic invasive physiological indices to define myocardial ischemia", JACC: Cardiovascular Interventions, vol. 10(8):751-760 (2017).

Janssen et al., "New approaches for the assessment of vessel sizes in quantitative (cardio-)vascular X-ray analysis", Int J Cardiovasc Imaging vol. 26:259-271 (2010).

Jiang et al., "Vascular tree reconstruction by minimizing a physiological functional cost", 2010 IEEE Computer Society Conference on Computer Vision and Pattern Recognition—workshops, San Francisco, CA, pp. 178-185, doi: 10.1109/CVPRW.2010.5543593.

Kappetein et al, "Current percutaneous coronary intervention and coronary artery bypass grafting practices for three-vessel and left main coronary artery disease: Insights from the SYNTAX run-in phase", European Journal of Cardio-Thoracic Surgery, vol. 29:486-491 (2010).

Kass et al., "Snakes: active contour models", Int. J. Comput. Vis. vol. 1:321-331 (1987).

Kern, "Serial lesion FFR made simple", Cath Lab Digest, vol. 20(9)(2012), in 2 pages, [retrieved on on Sep. 25, 2024], retrieved from the internet: https://www.hmpgloballearningnetwork.com/site/cathlab/articles/serial-lesion-ffr-made-simple.

Kirkeeide, "Coronary obstructions, morphology and physiologic significance", Quantitative Coronary Arteriography, Chap. 11:229-244 (1991).

Lethen et al., "Validation of noninvasive assessment of coronary flow velocity reserve in the right coronary artery—A comparison of transthoracic echocardiographic results with intracoronary doppler flow wire measurements", European Heart Journal, vol. 24:1567-1575 (2003).

Li et al, "Minimization of region-scalable fitting energy for image segmentation", in IEEE Transactions on Image Processing, vol. 17(10):1940-1949 (2008).

Marchenko, et al., "Vascular editor: from angiographic images to 3D vascular models", Journal of Digital Imaging, vol. 23:386-398 (2010).

Meimoun et al., "Non-invasive assessment of coronary flow and coronary flow reserve by transthoracic doppler echocardiography: a magic tool for the real world", European Journal of Echocardiography, vol. 9:449-457 (2008).

Mercer-Rosa et al., "Illustration of the additional value of real-time 3-dimensional echocardiography to conventional transthoracic and transesophageal 2-dimensional echocardiography in imaging muscular ventricular septal defects: does this have any impact on individual patient treatment", Journal of the American Society of Echocardiography, vol. 19(12):1511-1519 (2006).

Molloi et al., "Quantification of fractional flow reserve using angiographic image data", World Congress on Medical Physics and Biomedical Engineering, Munich, Germany, Sep. 7-12, 2009.

Molloi et al., "Estimation of coronary artery hyperemic blood flow based on arterial lumen volume using angiographic images", Int J Cardiovasc Imaging, vol. 28:1-11 (2012).

Neng et al., "Pre-stenting angiography-FFR based physiological map provides virtual intervention and predicts physiological and clinical outcomes", Catheterization and Cardio vascular Interventions, Wiley-Liss, New York, NY, vol. 101(6):1053-1061 (2023).

Ng et al., "Novel QCA methodologies and angiographic scores", Int J Cardiovasc Imaging vol. 27:157-165 (2011).

Nijjer et al., "Pre-angioplasty instantaneous wave-free ratio pull-back provides virtual intervention and predicts hemodynamic outcome for serial lesions and diffuse coronary artery disease", JACC: Cardiovascular Interventions, vol. 7(12):1386-1396 (2014).

Pellot et al, "A 3D reconstruction of vascular structures from two X-Ray angiograms using an adapted simulated annealing algorithm", IEEE Transactions of Medical Imaging, vol. 13(1):48-60 (1994).

Pijls et al., "Experimental basis of determining maximum coronary, myocardial, and collateral blood flow by pressure measurements for assessing functional stenosis severity before and after percutaneous transluminal coronary angioplasty", Circulation, vol. 87:1354-1367 (1993).

Pinho et al., "Assessment and stenting of tracheal stenosis using deformable shape models", Medical Image Analysis, vol. 15(2):250-266 (2010).

Polytimi et al., "Close to transplant renal artery stenosis and percutaneous transluminal treatment", Journal of Transplantation, vol. 2011, 7 pages (2011).

Rabbat et al., "Interpreting results of coronary computed tomography angiography-derived fractional flow reserve in clinical practice", Journal of Cardiovascular Computed Tomography, vol. 11(5):1-6 (2017).

Rimac et al., "Clinical value of post-percutaneous coronary intervention fractional flow reserve value: A systematic review and meta-analysis", Am Heart J. vol. 183:1-9 (2017).

Sarwal et al., "3-D reconstruction of coronary arteries", Proceedings of the 16th Annual Intl. Conference of the IEEE Engineering in Medicine and Biology Society, Engineering Advances: New Opportunities for Biomedical Engineers, Nov. 3, 1994, pp. 504-505.

Sato et al., "A viewpoint determination system for stenosis diagnosis and quantification in coronary angiogrphic image acquisition", IEEE Transactions on Medical Imaging, vol. 17(1):121-137 (1998).

Seifalian et al., "A new algorithm for deriving pulsatile blood flow waveforms tested using simulated dynamic angiographic data", Neuroradiology, vol. 31:263-269 (1989).

Seifalian et al., "Blood flow measurements using 3D distance-concentration functions derived from digital x-ray angiograms", Cardiovascular Imaging, Chap. 33:425-442 (1996).

Seifalian et al., "Validation of a quantitative radiographic technique to estimate pulsatile blood flow waveforms using digital subtraction angiographic data", Journal of Biomedical Engineering, vol. 13(3):225-233 (1991).

Shang et al., "Vascular active contour for vessel tree segmentation", in IEEE Transactions on Biomedical Engineering, vol. 58(4):1023-1032 (2011).

Shpilfoygel et al., "Comparison of methods for instantaneous angiographic blood flow measurement", Medical Physics, vol. 26(6):862-871 (1999).

Sianos et al., "The SYNTAX score: an angiographic tool grading the complexity of coronary artery disease", Euro Intervention, vol. 1(2):219-227 (2005).

Siogkas et al., "Quantification of the effect of percutaneous coronary angioplasty on a stenosed right coronary artery", 2010 10th IEEE Intl. Conference on Information Technology and Applications in Biomedicine, Nov. 3-5, 210, pp. 1-4 (2010).

(56) References Cited

OTHER PUBLICATIONS

Slomka et al., "Fully automated wall motion and thickening scoring system for myocardial perfusion SPECT: Method development and validation in large population", Journal of Nuclear Cardiology, vol. 19(2):291-302 (2012).

Sprague et al., "Coronary x-ray angiographic reconstruction and image orientation", Medical Physics, vol. 33(3):707-718 (2006).

Sun et al., "Coronary CT angiography: current status and continuing challenges", The British Journal of Radiology, vol. 85:495-510 (2012).

Takarada et al., "An angiographic technique for coronary fractional flow reserve measurement: in vivo validation", International Journal of Cardiovascular Imaging, published online pp. 1-10, Aug. 31, 2012.

Termeer et al., "Visualization of myocardial perfusion derived from coronary anatomy", IEEE Transactions on Visualization and Computer Graphics, vol. 14(6):1595-1602 (2008).

Tomasello et al., "Quantitative coronary angiography in the interventional cardiology", Advances in the Diagnosis of Coronary Atherosclerosis, Chap. 14:255-272 (2011).

Tsigkas et al., "Rapid and precise computation of fractional flow reserve from routine two-dimensional coronary angiograms based on fluid mechanics: The pilot FFR2D study", Journal of Clinical Medicine, vol. 13:1-13 (2024).

Tu et al., Assessment of obstruction length and optimal viewing angle from biplane X-ray angiograms, Int J Cardiovasc Imaging, vol. 26:5-17 (2010).

Tu et al., "In vivo assessment of optimal viewing angles from X-ray coronary angiography", EuroIntervention, vol. 7:112-120 (2011).

Tu et al., "In vivo assessment of bifurcation optimal viewing angles and bifurcation angles by three-dimentional (3D) quantitative coronary angiography", Int J Cardiovasc Imaging, published online Dec. 15, 2011, in 9 pages.

Tu et al., "The impact of acquisition angle differences on three-dimensional quantitative coronary angiography", Catheterization and Cardiovascular Interventions, vol. 78:214-222 (2011).

Tuinenburg et al., "Dedicated bifurcation analysis: basic principles", Int J Cardiovasc Imaging, vol. 27:167-174 (2001).

Voci et al., "Coronary flow: a new asset for the echo lab?", European Heart Journal, vol. 25:1867-1879 (2004).

Volcano Corporation, iFR instant wave-free RatioTM, "An introduction to iFR ScoutTM Pullback Measurements, Moving from Justified PCI to Guided PCI", 2015, in 11 pages, [retrieved on Aug. 29, 2024]. Retrieved from the Internet <URL: https://www.usa.philips.com/c-dam/b2bhc/master/education-resources/technologies/igt/iFR-Scout-In-Service.pdf>.

Weickert et al., "A scheme for coherence-enhancing diffusion filtering with optimized rotation invariance", Computer Vision, Graphics, and Pattern Recognition Group, Technical Report, Computer Science Series, pp. 1-20 (2000).

Weickert, "Anisotropic diffusion in image processing", ECMI, published by Teubner Stuttgart, Germany, 181 pages (2008).

Weickert et al., "A scheme for coherence-enhancing diffusion filtering with optimized rotation invariance", Journal of Visual Communication and Image Representation, vol. 13(1-2):103-118 (2002).

Wang et al., "Optimal viewing angle determination for multiple vessel segments in coronary angiographic image", IEEE Transactions on Nuclear Science, vol. 61(3):1290-1303 (2014).

Wang et al., "Global optimization angiographic viewing angles for coronary arteries with multiple segments", 35th Annual International Conference of the IEEE EMBS, pp. 2640-2643, Osaka, Japan, Jul. 3-7, 2013.

Wong et al., "Quantification of fractional flow reserve based on angiographic image data", The International Journal of Cardiac Imaging, vol. 28(1):13-22 (2012).

Wong et al., "Determination of fractional flow reserve (FFR) based on scaling laws: a simulation study", Physics in Medicine and Biology, vol. 53:3995-4011 (2008).

Wong et al., "Automated technique for angiographic determination of coronary blood flow and lumen volume", Acad. Radiol. vol. 13:186-194 (2006).

Xu et al., "Snakes, shapes, and gradient vector flow", IEEE Transactions on Image Processing, vol. 7:359-369 (1998).

Yang et al., "Attention-based multi-fidelity machine learning model for fractional flow reserve assessment", Computer Methods in Applied Mechanics and Engineering, vol. 432(117338):1-16 (2024).

Yang et al., "Novel approach for 3-D reconstruction of coronary arteries from two uncalibrated angiographic images", IEEE Transactions on Image Processing, vol. 18(7):1563-1572 (2009).

Youssef et al., "Role of computed tomography coronary angiography in the detection of vulnerable plaque, where does it stand among others?", Angiology, vol. 1(2):1000111-1-1000111-8 (2013).

Zhang et al., "Quantification of coronary microvascular resistance using angiographic images for volumetric blood flow measurement: in vivo validation", Am J Physio Heart Circ vol. 300(6):H2096-H2104 (2011).

Fearon et al., "Accuracy of fractional flow reserve derived from coronary angiography", Circulation, vol. 139:477-484 (2019).

Kornowski et al., "Online angiography image-based FFR assessment during coronary catheterization: A single-center study", The Journal of Invasive Cardiology, vol. 30:1-6 (2018).

Omori et al., "Angiogram based fractional flow reserve in patients with dual/triple vessel coronary artery disease", International Journal of Cardiology, https://doi.org/10.1016/j.ijcard.2019301-072, in 6 pages (2019).

Pellicano et al., "Validation study of image-based fractional flow reserve during coronary angiography", Circ Cardiovasc Interv, downloaded on Sep. 16, 2017 at https://circinterventions.ahajournals.org, pp. 1-12 (2017).

The CathWorks FFRANGIO™ System, The Wayback Machine, https://web.archive.org/web/20220424014347/https://www.cathworks/cathworks-ffrangio/, accessed on Apr. 29, 2025, in 9 pages (2022).

Witberg et al., "Diagnostic performance of angiogram-derived fractional flow reserve", JACC: Cardiovascular Interventions, vol. 13(4):488-497 (2020).

Invitation to Pay Additional Fees in application No. PCT/IB2025/055962, dated Sep. 16, 2025, in 16 pages.

* cited by examiner

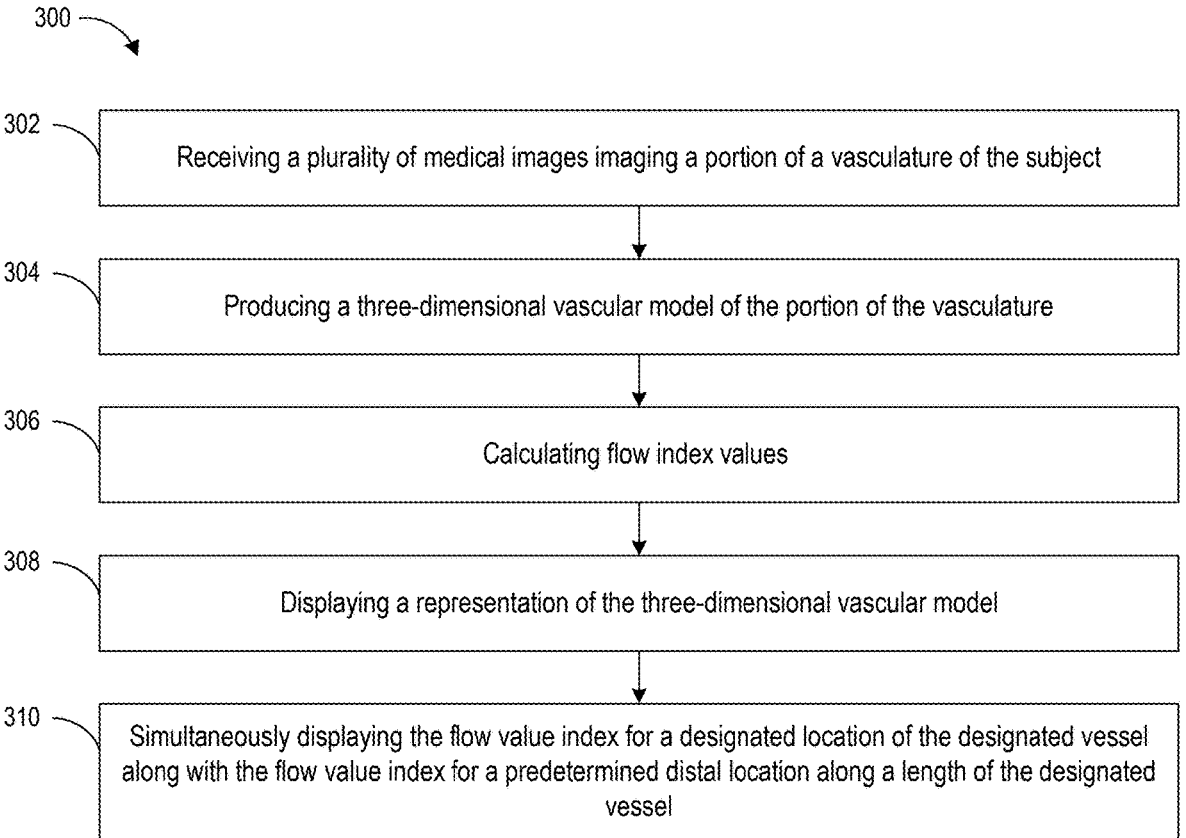

300

302 — Receiving a plurality of medical images imaging a portion of a vasculature of the subject 304 — Producing a three-dimensional vascular model of the portion of the vasculature 306 — Calculating flow index values 308 — Displaying a representation of the three-dimensional vascular model 310 — Simultaneously displaying the flow value index for a designated location of the designated vessel along with the flow value index for a predetermined distal location along a length of the designated vessel

602 — Receiving an input to display a QR code

604 — Generating the QR code according to the input

606 — Displaying the QR code

700 —

702 — Providing a security measure to an application running on a mobile device of a user by restricting access to the application 704 — Accessing the mobile device camera to capture image of QR code generated of vascular model information for a patient 706 — Presenting the vascular model information

SYSTEMS AND METHODS FOR DISPLAYING DISTAL FRACTIONAL FLOW RESERVE VALUES IN VASCULAR ANALYSIS

CROSS-REFERENCE TO RELATED APPLICATIONS

This application claims priority to U.S. Prov. Patent App. No. 63/659,214 and U.S. Prov. Patent App. No. 63/708,477, each of which is hereby incorporated herein by reference in its entirety.

BACKGROUND

Cardiovascular disease (CVD) is a leading cause of morbidity and mortality, with an estimated 244.1 million people worldwide with CVD, particularly due to the subsect of CVD, coronary artery disease (CAD). CAD can include acute coronary syndromes (ACS) and stable angina pectoris (SAP). CAD may involve a prolonged asymptomatic developmental phase, with clinical manifestations that often result in angina pectoris, acute myocardial infarction (MI), or cardiac death. The underlying mechanism that may cause CAD involves atherosclerotic lesions of the coronary arteries. Atherosclerosis is a plaque buildup that narrows the coronary arteries and decreases blood flow to the heart, resulting in ischemia or coronary stenosis.

Revascularization is the preferred therapy for patients with moderate to severe ischemia or stenosis, resulting in significant improvements for the patient due. Revascularization strategies include many techniques such as open-heart surgery, coronary artery bypass grafting (CABG), and percutaneous coronary intervention (PCI) methods such as balloon angioplasty, bare-meta stents (BMS), and first- and second-generation drug-eluting stents (DES). The severity of CAD can be assessed through vascular computer models.

SUMMARY

The systems, methods, and devices described herein each have several aspects, no single one of which is solely responsible for its desirable attributes. Without limiting the scope of this disclosure, several non-limiting features will now be discussed briefly.

One aspect of the disclosure provides a method for vascular assessment including: receiving a plurality of medical images imaging a portion of a vasculature of a subject, wherein the portion of the vasculature includes one or more vessels; producing, by automatic processing of the medical images, a three-dimensional vascular model of the portion of the vasculature including the one or more vessels based on the medical images; calculating flow index values quantifying vascular function along each of the one or more vessels based on the three-dimensional vascular model; displaying a representation of the three-dimensional vascular model including the one or more vessels; and for a designated vessel of the one or more vessels, simultaneously displaying the flow value index for a designated location of the designated vessel along with the flow value index for a predetermined distal location along a length of the designated vessel.

The method of the preceding paragraph can include any sub-combination of the following features: wherein the predetermined distal location is 80% of a length of the designated vessel; wherein the predetermined distal location is located at 80% of a length of the designated vessel, measured from a proximal end of the designated vessel; wherein the predetermined distal location is located between about 50% and 100% of a length of the designated vessel, measured from a proximal end of the designated vessel; wherein the predetermined distal location is proximal to a distal end of the designated vessel; wherein the predetermined distal location is identified via an icon displayed in connection with the three-dimensional vascular model; wherein the icon allows for the predetermined distal location to be adjustable along the designated vessel; wherein the icon restricts the predetermined distal location to be static along the designated vessel; wherein the predetermined distal location is based on one or more geometric characteristics, wherein the one or more geometric characteristic includes a target diameter of the designated vessel; wherein the predetermined distal location is based on a combination of a target distance along the designated vessel and one or more geometric characteristics, wherein the one or more geometric characteristic includes a target diameter of the designated vessel; wherein the designated vessel is automatically selected; wherein the designated vessel is manually selected; wherein the flow value index for the designated location is displayed above the flow value index for a predetermined distal location along a length of the designated vessel.

Another aspect of the disclosure provides a system including: a non-transitory data store storing computer-executable instructions; and a processor in communication with the non-transitory data store, wherein the computer-executable instructions, when executed by the processor, cause the processor to: receive a plurality of medical images imaging a portion of a vasculature of a subject, wherein the portion of the vasculature includes one or more vessels; produce, by automatic processing of the medical images, a three-dimensional vascular model of the portion of the vasculature including the one or more vessels based on the medical images; calculate flow index values quantifying vascular function along each of the one or more vessels based on the three-dimensional vascular model; display a representation of the three-dimensional vascular model including the one or more vessels; and for a designated vessel of the one or more vessels, simultaneously display the flow value index for a designated location of the designated vessel along with the flow value index for a predetermined distal location along a length of the designated vessel.

The system of the preceding paragraph can include any sub-combination of the following features: wherein the predetermined distal location is 80% of a length of the designated vessel; wherein the predetermined distal location is located between about 50% and 100% of a length of the designated vessel, measured from a proximal end of the designated vessel; wherein the predetermined distal location is proximal to a distal end of the designated vessel; wherein the predetermined distal location is identified via an icon displayed in connection with the three-dimensional vascular model; wherein receipt of user input to adjust the icon causes adjustment of the predetermined distal location along the designated vessel; wherein the icon is static.

Another aspect of the disclosure provides a method including: displaying a representation of a three-dimensional vascular model including a three-dimensional (3D) sizing tool that surrounds a portion of the three-dimensional vascular model, wherein the portion includes a volume of the three-dimensional vascular model which is based on a mapping of geometrical information of one or more vessels which form the three-dimensional vascular model to a length along the portion; displaying an interface for adjusting the 3D sizing tool, wherein an area along the interface corresponds to a length of the 3D sizing tool; receiving input to adjust the length of the 3D sizing tool via the area along the interface; and adjusting the length of the 3D sizing tool according to the input.

The method of the preceding paragraph can include any sub-combination of the following features: wherein the geometrical information includes at least one of vessel radius or vessel diameter; wherein the method, further includes: receiving user input to adjust a position of the 3D sizing tool along the three-dimensional vascular model; and adjusting the position of the 3D sizing tool along the three-dimensional vascular model, wherein a visual appearance of the 3D sizing tool is adjusted based on geometrical information associated with the three-dimensional vascular model; wherein the method, further includes adjusting the position along the three-dimensional vascular model in conjunction with movement of the area along the interface; wherein the method, further includes displaying the mapping of geometrical information to the length along the portion in the interface; wherein the method, further includes selecting, via the interface, a pullback curve to display a mapping between individual FFR values and individual positions along the three-dimensional vascular model; wherein the method, further includes, based on the 3D sizing tool being adjusted along the three-dimensional vascular model and the 3D sizing tool surrounding a bifurcated vessel, adjusting a position of the 3D sizing tool along a first vessel, wherein the bifurcated vessel includes the first vessel and a second vessel.

Another aspect of the disclosure provides a system including: a non-transitory data store storing computer-executable instructions; and a processor in communication with the non-transitory data store, wherein the computer-executable instructions, when executed by the processor, cause the processor to: display a representation of a three-dimensional vascular model including a three-dimensional (3D) sizing tool that surrounds a portion of the three-dimensional vascular model, wherein the portion includes a volume of the three-dimensional vascular model for which to determine a mapping of geometrical information to a length along the portion; display an interface for adjusting the 3D sizing tool, wherein an area along the interface corresponds to a length of the 3D sizing tool; receive input to adjust the length of the 3D sizing tool via the area along the interface; and adjust the length of the 3D sizing tool according to the input.

The system of the preceding paragraph can include any sub-combination of the following features: wherein the geometrical information includes at least one of radius, one or more vessel diameter; wherein the computer-executable instructions, when executed by the processor, cause the processor to: receive an input to adjust a position of the 3D sizing tool along the three-dimensional vascular model; and adjust the position along the three-dimensional vascular model; wherein the computer-executable instructions, when executed by the processor, cause the processor to adjust the position along the three-dimensional vascular model in conjunction with movement of the area along the interface; wherein the computer-executable instructions, when executed by the processor, cause the processor to display the mapping of geometrical information to the length along the portion in the interface; wherein the computer-executable instructions, when executed by the processor, cause the processor to select, via the interface, a pullback curve to display a mapping between individual FFR values and individual positions along the three-dimensional vascular model; wherein the computer-executable instructions, when executed by the processor, cause the processor to, when the 3D sizing tool is adjusted along the three-dimensional vascular model and the 3D sizing tool surrounds a bifurcated vessel, adjust a position of the 3D sizing tool along a first vessel, wherein the bifurcated vessel having the first vessel and a second vessel.

Another aspect of the disclosure provides one or more non-transitory computer-readable media including computer-executable instructions that, when executed by a computing system, cause the computing system to: display a representation of a three-dimensional vascular model including a three-dimensional (3D) sizing tool that surrounds a portion of the three-dimensional vascular model, wherein the portion includes a volume of the three-dimensional vascular model for which to determine a mapping of geometrical information to a length along the portion; display an interface for adjusting the 3D sizing tool, wherein an area along the interface corresponds to a length of the 3D sizing tool; receive input to adjust the length of the 3D sizing tool via the area along the interface; and adjust the length of the 3D sizing tool according to the input.

The one or more non-transitory computer-readable media of the preceding paragraph can include any sub-combination of the following features: wherein the geometrical information includes at least one of radius, one or more vessel diameter; wherein the instructions further include: receiving an input to adjust a position of the 3D sizing tool along the three-dimensional vascular model; and adjusting the position along the three-dimensional vascular model; wherein the instructions further include adjusting the position along the three-dimensional vascular model in conjunction with movement of the area along the interface; wherein the instructions further include displaying the mapping of geometrical information to the length along the portion in the interface; wherein the instructions further include selecting, via the interface, a pullback curve to display a mapping between individual FFR values and individual positions along the three-dimensional vascular model.

Another aspect of the disclosure provides method including: presenting a cardiac analysis on a user interface; receiving, on the user interface, user input to display at least one QR code configured to share the cardiac analysis; in response to the input, generating the at least one QR code which encodes at least a portion of the cardiac analysis and removes protected health information (PHI), wherein the portion includes one or more of a screenshot or a report associated with the cardiac analysis; and displaying the at least one QR code on the user interface.

The method of the preceding paragraph can include any sub-combination of the following features: wherein displaying the at least one QR code on the user interface further includes displaying an animated QR code, wherein the animated QR code alternates a displayed QR code by sequentially cycling through a plurality of QR codes; wherein displaying the at least one QR code on the user interface further includes displaying a series of QR codes, wherein the series of QR codes includes two or more of the at least one QR code displayed on the user interface; wherein displaying the at least one QR code on the user interface further includes displaying each of the at least one QR code according to threshold frequency; wherein the threshold frequency is between 5 Hz and 24 Hz; wherein the method further includes, in response to a mobile device capturing the at least one QR code, causing transfer of data to the mobile device; wherein the method further includes causing transfer of the data relating to the cardiac analysis with removed PHI to the mobile device; wherein the method further includes generating the at least one QR code that encodes: log data, the one or more screenshots, and the one or more reports, wherein the log data includes medical device network performance, wherein the one or more screenshots include redacted medical information of a patient, and wherein the one or more reports include medical diagnostic information regarding the patient; wherein the method further includes in response to a mobile device capturing the at least one QR code, causing transfer of data relating to the log data, the one or more screenshots, and the one or more reports to the mobile device; wherein the cardiac analysis is an interactive cardiac analysis responsive to user input, and wherein the method further includes: causing presentation, via a user device based on the QR code, of the interactive cardiac analysis, wherein the interactive cardiac analysis is responsive to user input received via the user device.

Another aspect of the disclosure provides a system including: a non-transitory data store storing computer-executable instructions; and a processor in communication with the non-transitory data store, wherein the computer-executable instructions, when executed by the processor, cause the processor to: present a cardiac analysis on a user interface; receive, on the user interface, an input to display at least one QR code to share the cardiac analysis; in response to the input, generate the at least one QR code that encodes at least a portion of the cardiac analysis and removes protected health information (PHI); and display the at least one QR code on the user interface.

The system of the preceding paragraph can include any sub-combination of the following features: wherein the computer-executable instructions, when executed by the processor, cause the processor to display an animated QR code, wherein the animated QR code alternates a displayed QR code by sequentially cycling through a plurality of QR codes; wherein the computer-executable instructions, when executed by the processor, cause the processor to display a series of QR codes, wherein the series of QR codes includes two or more of the at least one QR code displayed on the user interface; wherein the computer-executable instructions, when executed by the processor, cause the processor to display each of the at least one QR code according to threshold frequency; wherein the threshold frequency is between 5 Hz and 24 Hz; wherein the computer-executable instructions, when executed by the processor, cause the processor to, in response to a mobile device capturing the at least one QR code, cause transfer of data to the mobile device; wherein the computer-executable instructions, when executed by the processor, cause the processor to cause transfer of the data relating to the cardiac analysis with removed PHI to the mobile device; wherein the computer-executable instructions, when executed by the processor, cause the processor to generate the at least one QR code that encodes at least one of: log data, one or more screenshots, and one or more reports, wherein the log data includes medical device network performance, wherein the one or more screenshots include redacted medical information of a patient, and wherein the one or more reports include medical diagnostic information regarding the patient; wherein the computer-executable instructions, when executed by the processor, cause the processor to, in response to a mobile device capturing the at least one QR code, cause transfer of data relating to the log data, one or more screenshots, and one or more reports to the mobile device.

Another aspect of the disclosure provides one or more non-transitory computer-readable media including computer-executable instructions that, when executed by a computing system, cause the computing system to: present a cardiac analysis on a user interface; receive, on the user interface, an input to display at least one QR code to share the cardiac analysis; in response to the input, generate the at least one QR code that encodes at least a portion of the cardiac analysis and removes protected health information (PHI); and display the at least one QR code on the user interface.

The system of the preceding paragraph can include any sub-combination of the following features: wherein displaying the at least one QR code on the user interface further includes displaying an animated QR code, wherein the animated QR code alternates a displayed QR code by sequentially cycling through a plurality of QR codes; wherein displaying the at least one QR code on the user interface further includes displaying a series of QR codes, wherein the series of QR codes includes two or more of the at least one QR code displayed on the user interface; wherein displaying the at least one QR code on the user interface further includes displaying each of the at least one QR code according to threshold frequency; wherein the threshold frequency is between 5 Hz and 24 Hz; wherein the instructions further include, in response to a mobile device capturing the at least one QR code, causing transfer of data to the mobile device; wherein the instructions further include causing transfer of the data relating to the cardiac analysis with removed PHI to the mobile device; wherein the instructions further include generating the at least one QR code that encodes at least one of: log data, one or more screenshots, and one or more reports, wherein the log data includes medical device network performance, wherein the one or more screenshots include redacted medical information of a patient, and wherein the one or more reports include medical diagnostic information regarding the patient; wherein the instructions further include, in response to a mobile device capturing the at least one QR code, causing transfer of data relating to the log data, one or more screenshots, and one or more reports to the mobile device.

BRIEF DESCRIPTION OF DRAWINGS

Throughout the drawings, reference numbers are re-used to indicate correspondence between referenced elements. The drawings are provided to illustrate embodiments of the subject matter described herein and not to limit the scope thereof.

FIG. 3 illustrates is a flowchart of an example process for simultaneously displaying a flow value index for a designated location and a flow value index for a predetermined distal location.

DETAILED DESCRIPTION

Overview

Figure 1A:
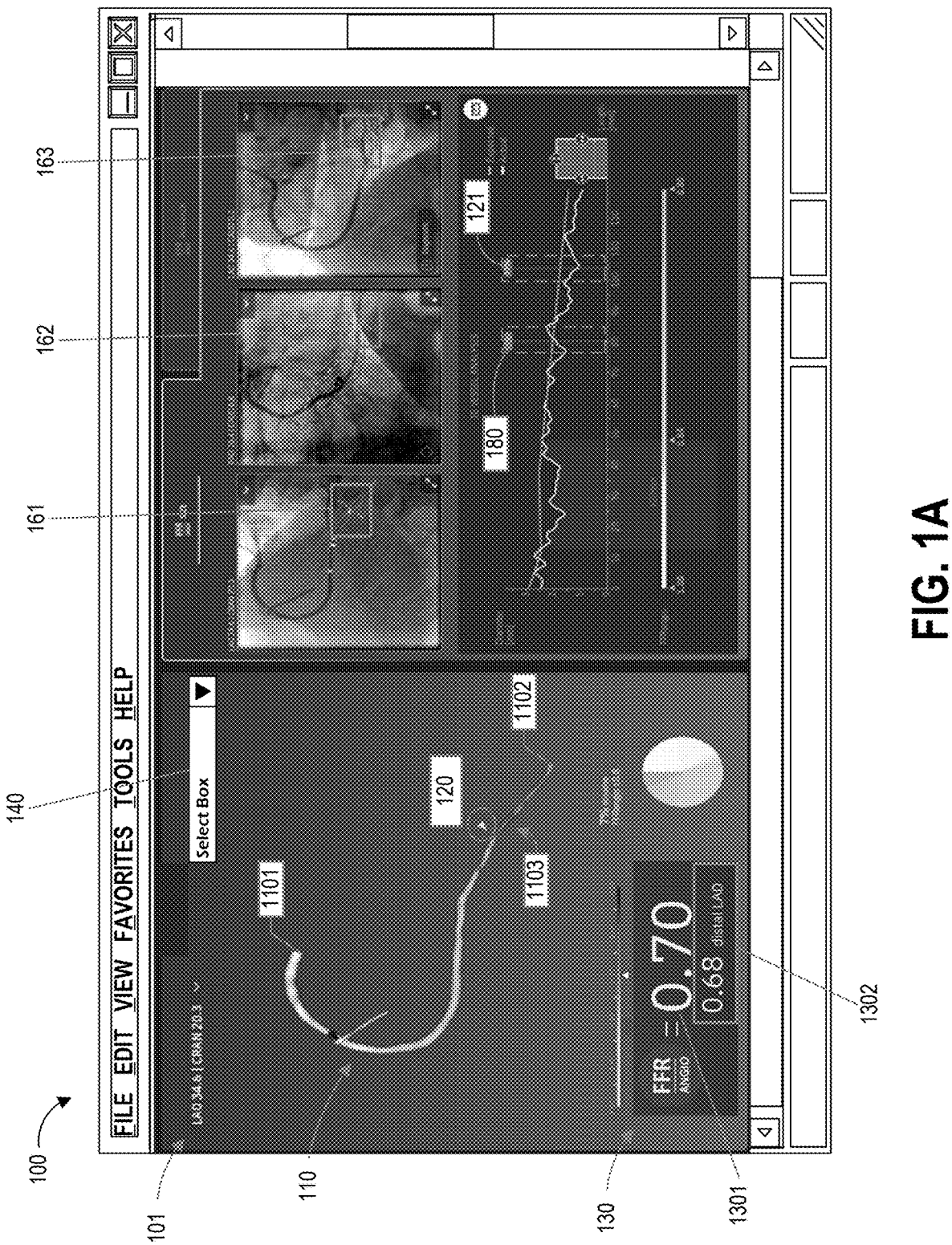
FIGS. 1A, 1B, 1C, 1D, and 1E illustrate examples of a user interface for displaying vascular information for a patient, including a flow value index and a distal flow value index.

This specification describes techniques to present information which is advantageous for a medical professional when performing a cardiac analysis of a patient. Specifically, this specification describes simplified user interface flows and back-end features to enable the quick, and accurate, analysis of cardiac images, such as angiographic images, used to determine the cardiac analysis. For example, and as will be escribed, a three-dimensional model associated with a portion of a patient's vasculature may be presented. In this example, different indices of vascular function, such as fractional flow reserve (FFR) values, may be presented as mapped to different lengths along one or more vessels of the patient's vasculature. A user may select a particular length along a vessel and view the corresponding FFR value. Advantageously, a distal FFR value may be simultaneously presented. As will be described, the distal FFR value may indicate an FFR value which is a threshold percentage from an end of the vessel (e.g., 80% from the end, 75% from the end). This may allow the medical professional to understand both an instant FFR value (e.g., at a selected location) along with a substantially ending FFR value for the same vessel. Thus, medical professional may determine an overall health associated with a vessel along with specific FFR values along the vessel.

As described herein, a system may analyze medical images to determine vessels which are matching (e.g., correspond with each other) between the medical images. Based on this matching, the system may generate a three-dimensional model of a portion of a patient's vasculature. For example, the three-dimensional model may reflect three-dimensional geometry information associated with vessels which form the portion. Example geometry information may include, for example, diameter or radii associated with individual locations along lengths of the vessels. The system may then determine FFR values for the individual locations. This information may be referred to herein as a cardiac analysis. Description related to determining or calculating an index indicative of vascular function is included in U.S. Pat. No. 10,595,807 and incorporated herein by reference in its entirety.

A user may leverage an interactive user interface which presents results or information associated with the above-described cardiac analysis. For example, FIG. 1 illustrates a representation of a three-dimensional model along with a mapping between geometrical information (e.g., diameter) and length along a vessel. As another example, FIG. 8C illustrates a representation of a three-dimensional model along with a mapping between FFR value and length along a vessel. As described herein, a user may select a particular length along a vessel and view the FFR value (e.g., instantaneous FFR value) for that particular length. Advantageously, the three-dimensional model may update to reflect the FFR value, for example proximate to the three-dimensional model. In addition, a distal FFR value for that vessel may be simultaneously presented as being proximate to the three-dimensional model. In this way, the user may understand the overall health of the vessel. As may be appreciated, the vessel may have negative health effects based on one or more lesions being included in the vessel. Thus, a specific FFR value along the vessel may reflect a constraining of the vessel and the distal FFR value may be used to inform the overall health of the vessel due to the one or more lesions.

In addition to presenting distal FFR values, this application describes techniques to share the above-described cardiac analysis. For example, a matrix barcode (e.g., a QR code) may be presented in a user interface. In this example, the matrix barcode may encode a snapshot of the cardiac analysis. A user device may use its camera to capture an image of the matrix barcode to obtain the snapshot. As another example, an animated matrix barcode (e.g., a series of QR codes, such as those adjusting at a particular frequency) may be used to encode underlying data which forms the cardiac analysis. For this example, the underlying data may include mappings between geometrical information and lengths along vessels used in the cardiac analysis. The underlying data may also include mappings between FFR values and lengths along the vessels.

As will be described, personal health information (PHI), or other private information, may advantageously be removed prior to encoding as matrix barcode(s). In this way, the user of the user device may view the cardiac analysis with all PHI removed thus preserving patient privacy while enabling other users to view the information.

Figure 8A:
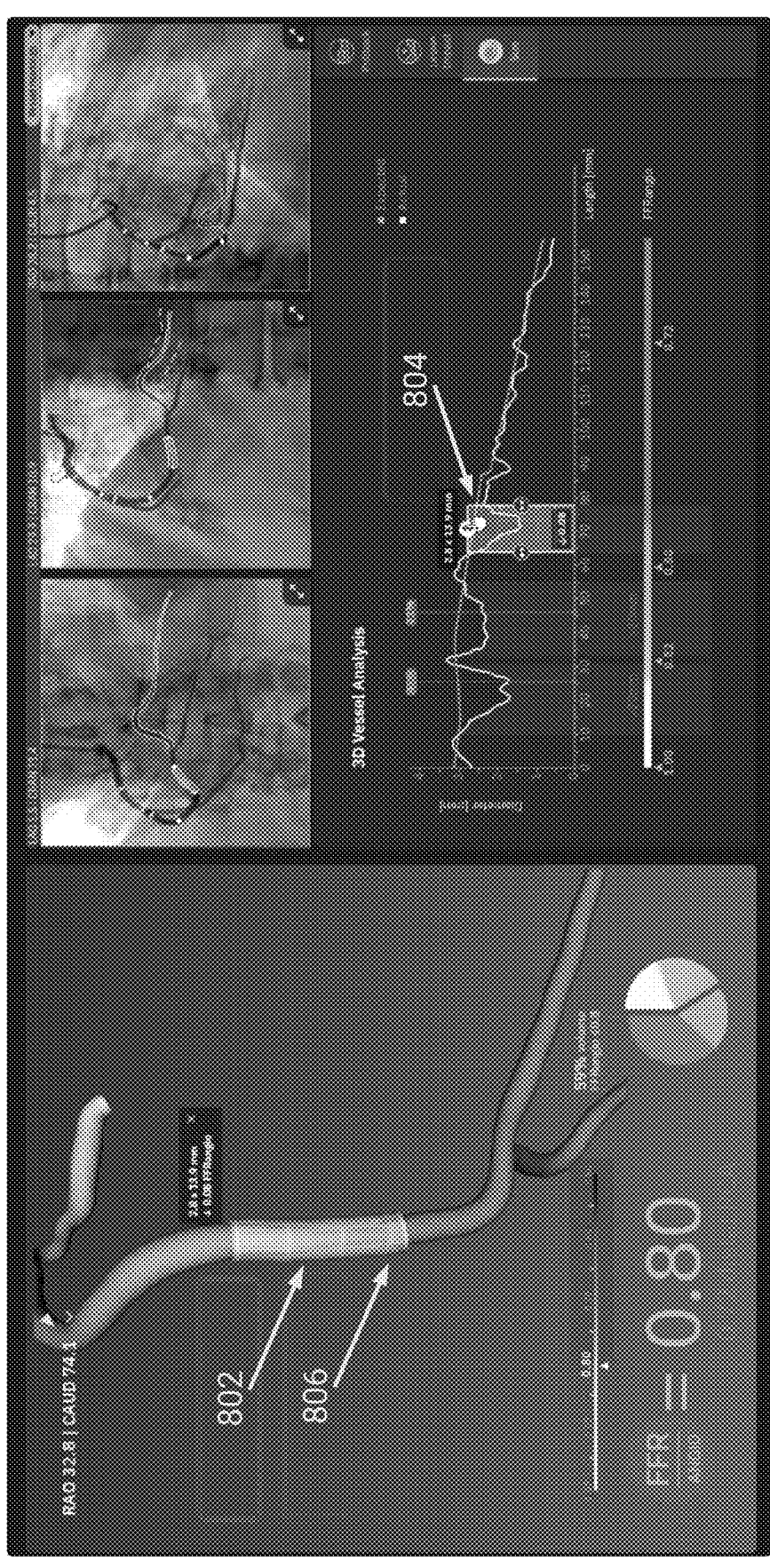
FIGS. 8A-8C illustrate example user interfaces which include a three-dimensional sizing tool.
Figure 8B:
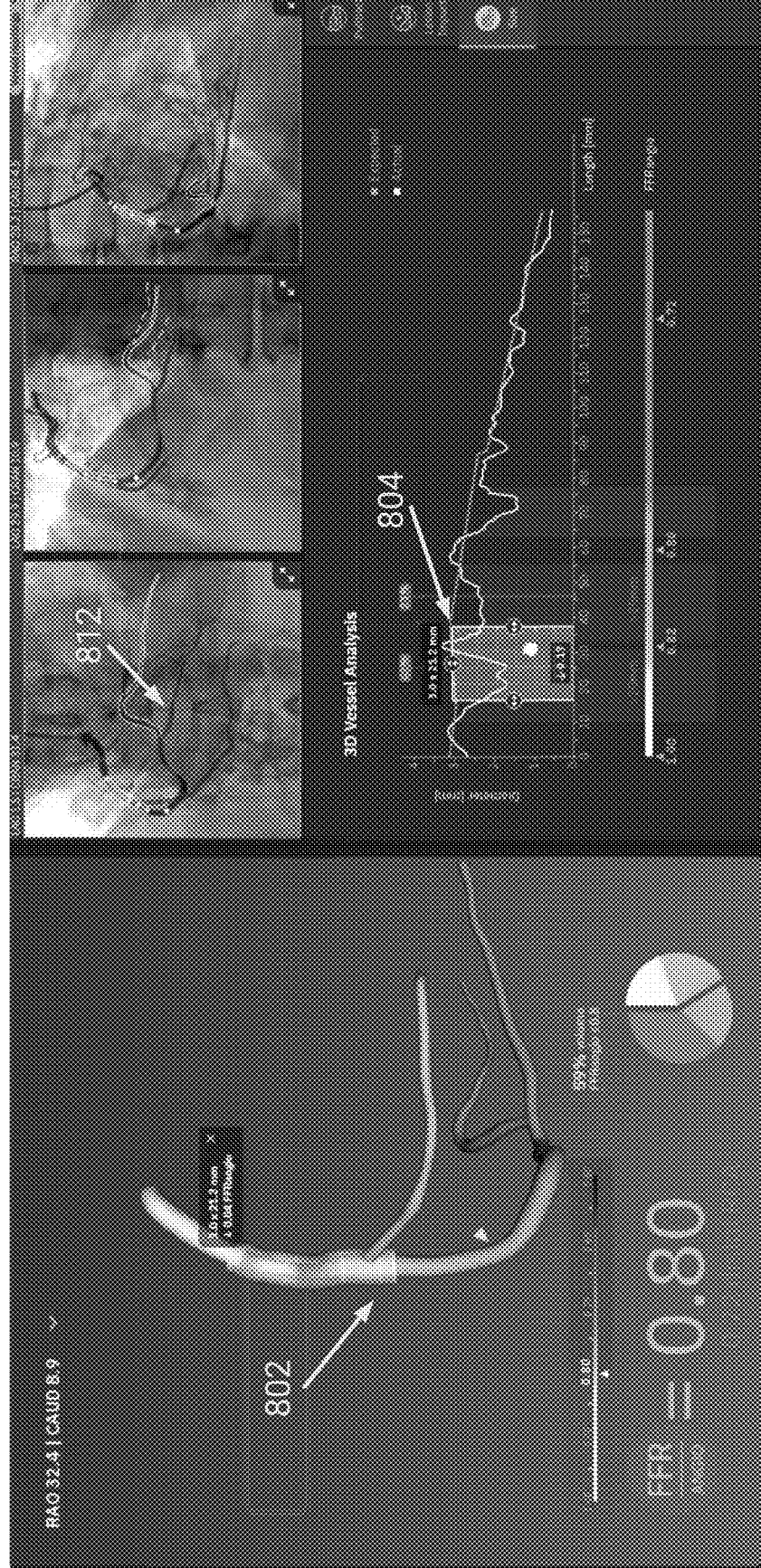
Figure 8C:
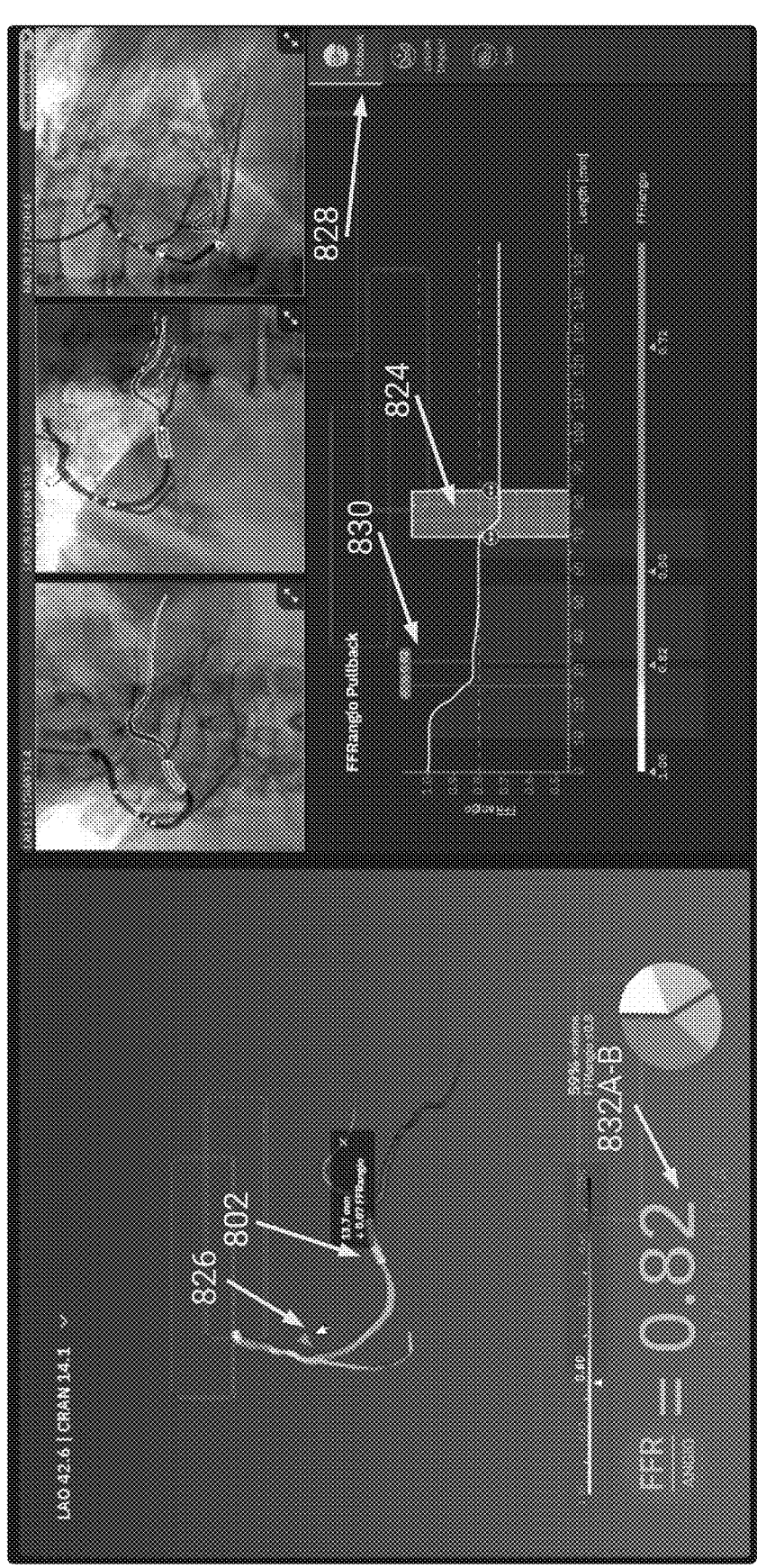

Additionally, the user interface described herein, such as those in FIGS. 8A-8C, may include a three-dimensional representation of geometrical information for a specified range of lengths along a vessel. The three-dimensional representation, which is referred to herein as a three-dimensional sizing tool, provides an easy-to-understand graphical understanding of constriction associated with a lesion in a vessel. For example, the three-dimensional sizing tool may be positioned about a vessel included in the three-dimensional representation of the portion of vasculature. The position may correspond to the selected range of lengths along the vessel. In this example, the sizing tool may be illustrated as a sleeve surrounding the vessel. To inform geometrical information, the three-dimensional sizing tool may be adjusted in diameter along the length of the vessel.

The figures and description herein may be combined, for example a user interface may present a distal FFR value, a three-dimensional sizing tool, QR code, and so on.

The above and other features will now be described in more detail.

"QCA" is not intended to be limiting and may be used to refer to any other minimally invasive coronary physiology assessment, such as 2D radiography, 3D quantitative assessments, etc.

"Ischemia," "stenosis," and/or "coronary stenosis" are not intended to be limiting and may be interchanged or refer to any other condition related to the narrowing of the vessels that may be treated through revascularization. "Lesions" refer to the portion of the cardiac vasculature where the vessel is narrower and is not intended to be limited to relating to ischemia or coronary stenosis, but to any CAD.

"Stent" is not intended to be limiting and may refer to any other method of widening a vessel, whether by physical intervention, chemical intervention, any other intervention, or a combination of interventions. Although "stent" is used in reference to PCI, this is not intended to be limiting for either, and any other widening method may be utilized for PCI, or any other revascularization technique can utilize a stent.

In some embodiments, additionally or alternatively, the vasculature may be of another organ, for example, a kidney, a retina, and/or a brain. It should be understood, where cardiac vasculature is described in particular, that implicit reference is also made to embodiments relating to the vasculature of another organ.

Example User Interface

FIGS. 1A, 1B, 1C, 1D, and 1E show various examples of a user interface for vascular assessment. As illustrated in FIG. 1A, a user interface 100 includes an interface 101, a vessel 110, an icon 120, a vessel length marker 121, a parameter display 130, a select box 140, distal markers 161, 162, and 163, and a target lesion marker 180. The vessel 110 features a proximal end 1101, a distal end 1102, and a distal point 1103. The parameter display 130 further includes a flow value index 1301 and a distal flow value index 1302, which are displayed in conjunction with the vessel 110. The user interface 100 serves as a platform for the vascular assessment method, providing a user interface for interaction and visualization of the vascular data. The interface 101 facilitates user interaction with the user interface 100, allowing for the selection and manipulation of various features within the user interface 100.

The vessel 110 represents a three-dimensional model of a portion of a subject's vasculature, with the proximal end 1101 and the distal end 1102 indicating the extent of the vessel 110 within the model. The distal point 1103 is a location along the length of the vessel 110, which can be identified and assessed using the user interface 100. The proximal end 1101 and the distal end 1102 of the vessel 110 may provide model boundaries for assessing vascular health and the determination of the severity and location of potential stenosis or blockages. The user interface 100 may identify the proximal end 1101 and the distal end 1102 based on the analysis of flow value index (may also be referred to herein as "Fractional Flow Reserve" and/or "FFR") values along the vessel. In some examples, a user may identify the proximal end 1101 and the distal end 1102 from a vessel model, images, a threshold FFR value, or another technique applicable to identifying the proximal end 1101 and the distal end 1102. For example, the user may interact with the user interface to select an image corresponding to the vessel model to select the proximal end 1101. The proximal end 1101 may represent a starting point of the vessel for performing vascular assessments. In some examples, the proximal end 1101 may correspond to where the FFR value is at its maximum (for example, an FFR value of 1.00). The FFR value of 1.00 may indicate optimal blood flow and serves as a reference point for comparison along the vessel. In some examples, the proximal end 1101 may correspond to a point located near the origin or entry point of the vessel within the cardiovascular system. The distal end 1102 may correspond to an endpoint or termination of the vessel. In some examples, the distal end 1102 may be located along the vessel where the FFR value falls below a threshold (for example, an FFR value of 0.80). The FFR threshold may indicate a reduced blood flow and may be used to determine the extent and severity of any potential stenosis or blockages. By identifying the proximal end 1101 and the distal end 1102, the user interface 100 may establish spatial boundaries of the vessel and defines the length of the vessel between these points. The spatial boundaries may provide a reference for evaluating the impact of lesions or obstructions on blood flow and assist in determining the appropriate course of action for a patient.

The distal point 1103 may indicate a reference point along the vessel 110. In some examples, the user interface 100 may estimate a distal FFR value measured at the distal point 1103. In this manner, displaying the distal FFR value and the distal point 1103 may present a reference for a user to assess the severity of any potential stenosis or blockage and illustrate a location along the vessel for performing a medical procedure. By measuring the FFR value at this specific location, which may be approximately 80% along the length of the vessel between the proximal end 1101 and the distal end 1102, the user can evaluate the impact of any lesions or obstructions on the blood flow within the vessel. In some cases, measuring the FFR value can be based on geometric characteristics alone or in combination with a percentage of the length of the vessel. In some examples, the distal point 1103 may be anywhere along the vessel 110. For example, the distal point 1103 may be between approximately 50% and approximately 100% along a length of the vessel 110 between the proximal end 1101 and the distal end 1102, for example, between 55% and approximately 95%, between 60% and approximately 90%, between approximately 65% and approximately 85%, between approximately 70% and approximately 80%, between approximately 75% and approximately 75%, or any value or range between any of these values or ranges or any value or range bounded by any combination of these values, although values or ranges outside these values or ranges can be used in some cases. In some examples, the distal point 1103 may be absent from the vessel 110. The distal point 1103, along with the FFR values measured at different locations along the vessel, enables the user to assess the appropriate course of treatment. This information aids in enhances patient care and improving outcomes in the management of cardiovascular diseases.

The icon 120 may be displayed in association with the vessel 110 and serves as a visual indicator for the user to identify and interact with specific points along the vessel 110. The icon 120 in FIG. 1 serves as a visual marker that can be adjusted by a user to indicate a specific point along the vessel 110 where an FFR value is to be measured. The position of the icon 120 may correspond to the value displayed in the parameter display 130, providing a clear visual representation of the location being assessed. In some examples, the icon 120 may be static, positioned along the vessel 110 without an ability to adjust a position of the icon 120 along a length of the vessel. In some examples, a position of the icon 120 is adjustable. For example, a user interface 100 may adjust the position of the icon 120 in response to receiving a user's input. The adjustability of the icon 120 allows the user interface 100 to precisely mark the desired point along the vessel 110 for FFR measurement. The user interface 100 may adjust the icon 120 along the vessel 110 to select the exact location where the FFR value is to be determined.

In some examples, the position of the icon 120 may correspond to a position of the vessel length marker 121. For example, the vessel length marker 121 may adjust laterally along a 3D vessel analysis graph (e.g., based on user input), plotting a vessel diameter according to the vessel length. In this way, the vessel length marker 121 may adjust along an axis of the vessel length, which causes a position of the icon 120 to be adjusted along the vessel 110. The updated position of the icon 120 may cause the FFR value (e.g., flow value index 1301) to be updated to correspond with that position. The distal FFR value may be constant as it represents a value distal to the end of the vessel. In some examples, the vessel length marker 121 adjusting towards a minimum length (such as a length of "0") may adjust the icon 120 towards the proximal end 1101 (or the distal end 1102 in some cases). In some examples, the vessel length marker 121 adjusting towards a maximum length may adjust the icon 120 towards the distal end 1102 (or the proximal end 1101 in some cases).

The above-described flexibility enables the user interface 100 to target specific areas of interest, such as regions with suspected stenosis or areas where the vessel's health needs to be evaluated. The parameter display 130, in conjunction with the icon 120, provides real-time feedback to the user. As the icon 120 is adjusted along the vessel 110, the user interface 100 may compute and update the FFR value to display the FFR value in the parameter display 130. This immediate visual feedback allows the user to assess the impact of different locations along the vessel 110 on the FFR value, aiding in the decision-making process. By adjusting the icon 120 and correlating its position with the displayed FFR value in the parameter display 130, the user interface 100 enhances the precision and accuracy of FFR measurements. This feature empowers the user to make informed clinical judgments based on the specific locations along the vessel 110 that are being evaluated, ultimately leading to improved patient care and treatment outcomes.

The parameter display 130 provides quantitative information about the vascular function at specific locations along the vessel 110, including the flow value index 1301 and the distal flow value index 1302, which are displayed to give a comprehensive understanding of the vascular assessment. The parameter display 130 in FIG. 1 may provide vascular information to the user during the vascular assessment process. The parameter display 130 may allow the user to quickly recognize and interpret both the FFR value and the distal FFR value, facilitating efficient decision-making without the need for repeated calculations or invasive procedures. The parameter display 130 may present the FFR value corresponding to the specific point along the vessel identified by the adjustable icon 120. The FFR value represents the fractional flow reserve at the selected location, providing insights into the hemodynamic significance of any potential stenosis or blockage. By displaying the FFR value in real-time, the parameter display 130 enables the user to assess the severity of the condition and make informed treatment decisions promptly. In addition to the FFR value, the parameter display 130 also includes the distal FFR value. This value corresponds to the FFR measurement at the predetermined distal point 1103 along the vessel. By simultaneously displaying both the FFR value and the distal FFR value, the parameter display 130 allows the user to compare and evaluate the impact of lesions or obstructions along the vessel's length. The parameter display 130 simultaneously displaying both the FFR value and the distal FFR value on the same display eliminates the need for the user to perform additional calculations or invasive procedures to obtain this information. This streamlined presentation enhances efficiency and expedites the interpretation of results, enabling the user to quickly assess the significance of any lesions or obstructions along the vessel. The efficient workflow ultimately leads to improved patient care and treatment outcomes.

In some examples, the parameter display 130 may be positioned anywhere along the interface 101. For example, as illustrated, the parameter display 130 is located in a bottom-left position of the interface 101. In some examples, the parameter display 130 may be located at a bottom-right position of the interface 101 (or a top-left, top-right, central, bottom-center, top-center location, or another position relative to the interface 101). In some examples, the parameter display 130 may be hidden until the interface 101 receives a prompt from the user. In some examples, the parameter display 130 may include the text "FFR," "ANGIO," "DISTAL," or other words to represent the content of the parameter display.

The distal flow value index 1302 may display a distal FFR value associated with a blood vessel. In some examples, the distal flow value index 1302 may correspond to a distal FFR value of a displayed blood vessel (such as, vessel 110) shown on the user interface 100. A system (for example, system 200 in FIG. 2) may compute the distal FFR value associated with one or more positions along the blood vessel and/or geometry characteristics of the blood vessel.

The system may identify one or more positions to compute the distal FFR value based on a distance along a length of the blood vessel, as disclosed herein. The system may calculate the distal FFR according to a distal point 1103, as disclosed herein. For example, a position to compute the distal FFR value may correspond to 80% of a length associated with the blood vessel. The system may identify the one or more positions according to a target distance along a length of the blood vessel. For example, the target distance may be a distance from an end of the blood vessel (such as, 80% of a length between a proximal end 1101 and a distal end 1102). The system may compare a position with the target distance to determine whether to compute the distal FFR value. In some cases, when the position is less than the target distance, the system may identify another position past the target distance.

The system may identify one or more positions to compute the distal FFR value based on one or more geometric characteristic of the blood vessel. The geometric characteristic may include one or more of a diameter (e.g., measurement of a blood vessel opening for blood to flow), radius, blood vessel wall thickness, or another geometric characteristic of the blood vessel. The geometric characteristic(s) may be with respect to various positions along the blood vessel. The system may identify one or more positions that satisfy geometric characteristic thresholds (for example, including a target diameter, target radius, target thickness of the blood vessel, etc.). In some examples, the system may identify a position along a vessel in which the diameter or radius is below a threshold.

In some examples, the system may identify the one or more positions according to a function (or model) using the geometric characteristics and the distance along the vessel. For example, the system may compare a plurality of diameters along the vessel to a threshold diameter. The system may order positions associated with the plurality of diameters according to how close the positions are to a target distance. The system may select the position that is closest to the target distance and meets the threshold diameter. In some cases, the system may identify a first position along the blood vessel to compute a distal FFR value according to the target distance from an end of the blood vessel (such as, 80% of a length between a proximal end 1101 and a distal end 1102). In some cases, the system may determine that the first position corresponds to geometric characteristics that are unable to meet the geometric characteristic threshold. For example, the diameter of the blood vessel at the first position may be below a target diameter value. Accordingly, the system may identify a second position along the blood vessel with geometric characteristics meeting the geometric characteristic threshold and past the target distance along the blood vessel to compute the distal FFR value. For example, the second position may be at a distance satisfying the target distance (such as 75% of the total length of the blood vessel) with a diameter satisfying the target diameter. In some cases, the system may identify the position identified to meet the target distance and geometric characteristic threshold as the distal point 1103.

In some examples, the system may compute the distal FFR value according to the geometry characteristics of the blood vessel. The display 100 may then provide the calculated distal FFR value as the distal flow value index 1302.

The flow value index 1301 may be positioned adjacent to the distal flow value index 1302. For example, as illustrated, the distal flow value index 1302 may be positioned below the flow value index 1301. In some examples, the distal flow value index 1302 may be positioned above the flow value index 1301 (or to the left/right, diagonal, larger, smaller, or another position or size relative to the flow value index 1301). In some examples, the distal flow value index 1302 may appear when a selection of a main vessel of the vessel 110 occurs. In some examples, the distal flow index 1302 may be always present on the interface 101. The flow value index 1301 may be located anywhere along the interface 101 separate from where the distal flow value index 1302 is located. For example, the flow value index 1301 may be positioned in a bottom-left corner of the interface 101, while the distal flow value index 1302 may be positioned at another location of the interface 101. In some examples, the interface 101 may display the flow value index 1301 without the distal flow value index 1302 (or display the distal flow value index 1302 without the flow value index 1301). In some examples, the flow value index 1301 may be a numerical value (such as "0.70" as illustrated). The distal flow value index 1302 may be a numerical value (such as "0.68" as illustrated). In some examples, the flow value index 1301 (and/or the distal flow value index 1302) may be displayed on a graph, table, visualization, or another form to represent the flow value index 1301 on the interface 101. In some examples, the flow value index 1301 (and/or distal flow value index 1302) may update in real-time. For example, the flow value index 1301 may update according to selected images or a model displayed on the interface 101. In some examples, the distal flow value index 1302 (and/or flow value index 1301) may update a display, while the flow value index 1301 (and/or distal flow value index 1302) remains the same.

The select box 140 in FIG. 1 may allow a user to select from various options within the user interface 100, including the selection of different QR codes for the user interface 100 to display. As will be described below, the QR codes may be analyzed by end-user devices (e.g., mobile devices, laptops, tablets) to obtain information encoded by the QR codes. For example, the end-user devices may include cameras which can capture images of the QR codes.

In some examples, the select box 140 may provide the ability to choose a type of QR code to generate by the user interface 100. For example, a first option in the select box 140 may be a debugging mode QR code. When selected, the user interface 100 may generate a QR code including debugging information and diagnostic data related to the vascular assessment process. This QR code can be used for troubleshooting and debugging purposes, allowing authorized personnel to analyze and identify any issues or errors that may occur during the assessment. Another option in the select box 140 is a medical information QR code. When selected, the user interface 100 may generate a QR including patient-specific information, such as vascular information, vascular model, dynamic reports, medical history, test results, and other relevant data. The QR code generated from the second option is intended for use in securely sharing medical information with authorized healthcare professionals or for storage in the patient's medical records. The medical information QR code is designed to comply with privacy regulations and ensure the confidentiality and integrity of sensitive patient data. Whether for debugging purposes or securely sharing medical information, the select box 140 allows users to tailor the QR code generation process to their requirements.

The distal markers 161, 162, and 163 may include visual indicators along diagnostic images to denote specific points of interest or measurement locations for a vessel. For example, the distal markers 161, 162, 163 may indicate a distal point (such as distal point 1103). The distal markers 161, 162, and 163 in FIG. 1 may be associated with the distal point 1103 of the vessel. These markers serve as visual indicators in the respective images, representing specific distal locations along the vessel. In some examples, the user interface 100 may adjust a position of the distal point 1103, which in turn may adjust locations for where the distal markers 161, 162, and 163 are positioned in their respective images. The distal markers 161, 162, and 163 may provide visual indications for identifying and referencing specific points along the vessel for analysis. By adjusting the distal point 1103, the user interface 100 can precisely select the desired location for assessing the vessel's health and functionality. This adjustability allows for flexibility in targeting areas of interest or suspected abnormalities along the vessel. The association between the distal markers 161, 162, 163 and the distal point 1103 provides visual correlations to assist the user with identifying the specific locations of interest in the images. The visual correlations may facilitate the interpretation of the vascular assessment results and aids in the identification of potential obstructions or abnormalities along the vessel. By adjusting the distal point 1103, the user interface 100 can effectively update the position of the distal markers 161, 162, and 163 in their respective images. In this manner, the user interface 100 may enhance accuracy and precision of the assessment process, allowing for targeted analysis and evaluation of the vessel's condition. Overall, the distal markers 161, 162, and 163, in association with the adjustable distal point 1103, provide a tool for user to identify and assess specific locations along the vessel.

The target lesion marker 180 may correspond to a selected lesion associated with the vessel 110. For example, the user interface 100 may receive input identifying a position along the vessel 110 for a selected lesion. The user interface 100 may display the position of the selected lesion with the target lesion marker 180.

FIGS. 1B, 1C, 1D, 1E show example user interfaces illustrating blood vessel assessments as disclosed herein. As illustrated in FIGS. 1B, 1C, 1D, and 1E, user interfaces 400a, 400b, 400c include an interface 401, a vessel 410, an icon 420, a vessel length marker 421, a parameter display 430, a select box 440, distal markers 461, 462, and 463, and target lesion marker 480. The vessel 410 features a proximal end 4101, a distal end 4102, and a distal point 4103. The parameter display 430 further includes a flow value index 4301 and a distal flow value index 4302, which are displayed in conjunction with the vessel 410. The user interface 400a serves as a platform for the vascular assessment method, providing a user interface for interaction and visualization of the vascular data. The interface 401 facilitates user interaction with the user interfaces 400a, 400b, 400c, allowing for the selection and manipulation of various features within the user interfaces 400a, 400b, 400c.

The user interfaces 400a, 400b, 400c may include elements and functions similar (or substantially similar) to the user interface 100 described in FIG. 1A. For example, the interface 401, the vessel 410, the icon 420, the vessel length marker 421, the parameter display 430, the select box 440, the distal markers 461, 462, 463, and the target lesion marker 480 may each be the same (or substantially similar) to the interface 101, the vessel 110, the icon 120, the vessel length marker 121, the parameter display 130, the select box 140, the distal markers 161, 162, 163, and the target lesion marker 180 as disclosed in FIG. 1A, respectively. Additionally, the proximal end 4101, the distal end 4102, and the distal point 4103 may each be the same (or substantially similar) to the proximal end 1101, the distal end 1102, and the distal point 1103. The flow value index 4301 and the distal flow value index 4302 may also each be the same (or substantially similar) to the flow value index 1301 and the distal flow value index 1302.

Figure 1B:
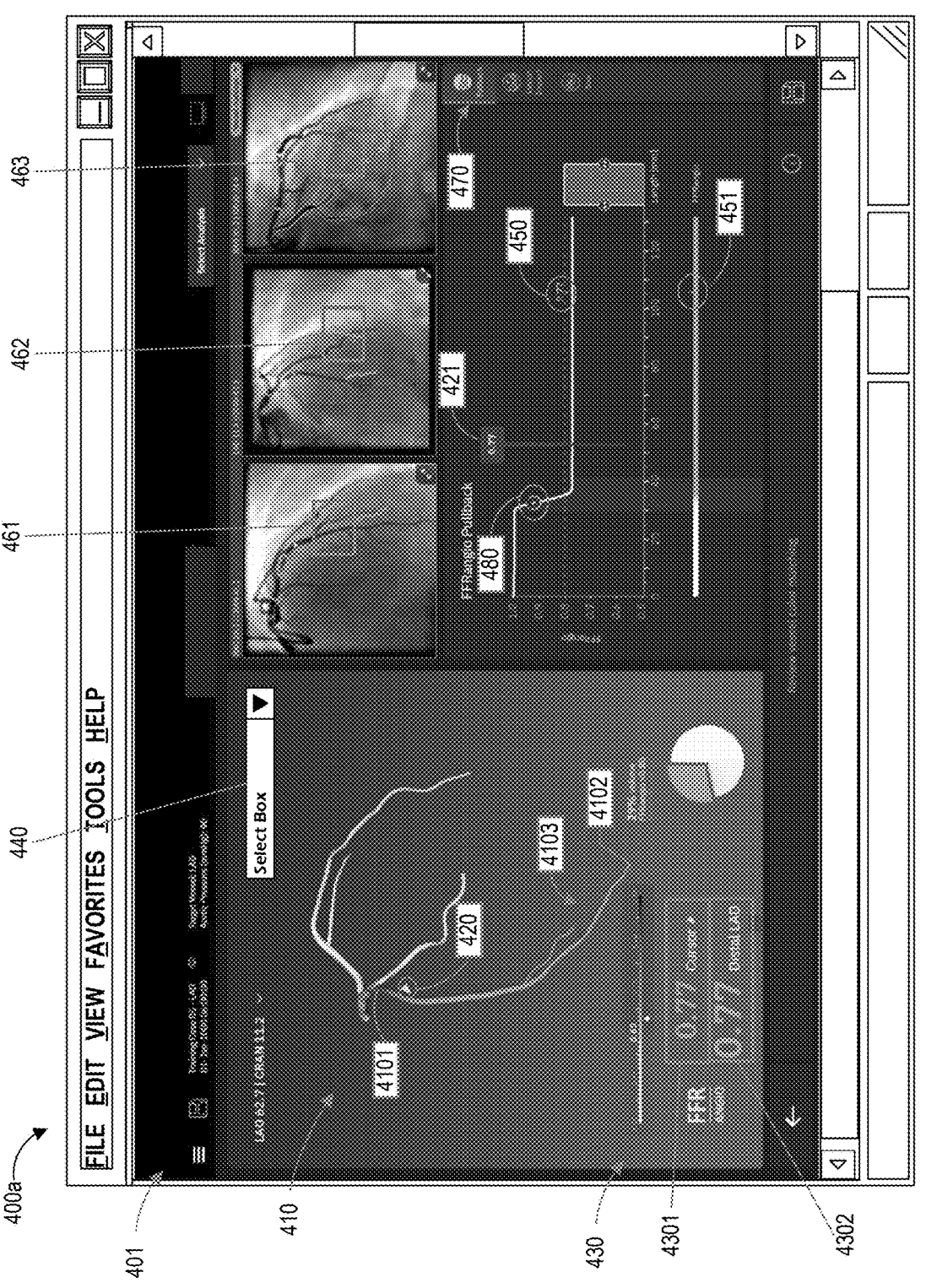

As illustrated in FIG. 1B, the user interface 400a may include a first selectable parameter 470. The first selectable parameter 470 may include a pullback curve icon. In some cases, when the interface 401 receives an input to select the first selectable parameter 470, the interface 401 may display an FFR pullback curve. The FFR pullback curve may include the target lesion marker 480 and a first distal marker 450. The FFR pullback curve may provide a graphical representation of FFR values for various positions along the vessel 410. The FFR pullback curve may include an X-axis corresponding to length along the vessel 410 and a Y-axis corresponding to FFR value.

The first distal marker 450 may indicate a position along the length of the vessel 410 where the system computed the distal FFR value. For example, the distal FFR value computed at the distal point 4103. The first distal marker 450 may include an identifier, such as a geometric shape indicating a position along the FFR pullback curve associated with the distal point 4103.

The FFR pullback curve may include a one-dimensional graphic further displaying a color associated with each position along the length of the vessel 410, with the color being selected based on an FFR value, and a position of a second distal marker 451. The color associated with each position may correspond to an FFR value at each of the positions. The one-dimensional graphic may be associated with a length of the vessel 410. In this way, a position along the one-dimensional graphic may correspond to a position along the vessel 410. Accordingly, the one-dimensional graphic may indicate a position of the distal point 4103. The second distal marker 451 may include an identifier, such as a geometric shape indicating a position along the FFR pullback curve associated with the distal point 4103.

Figure 1C:
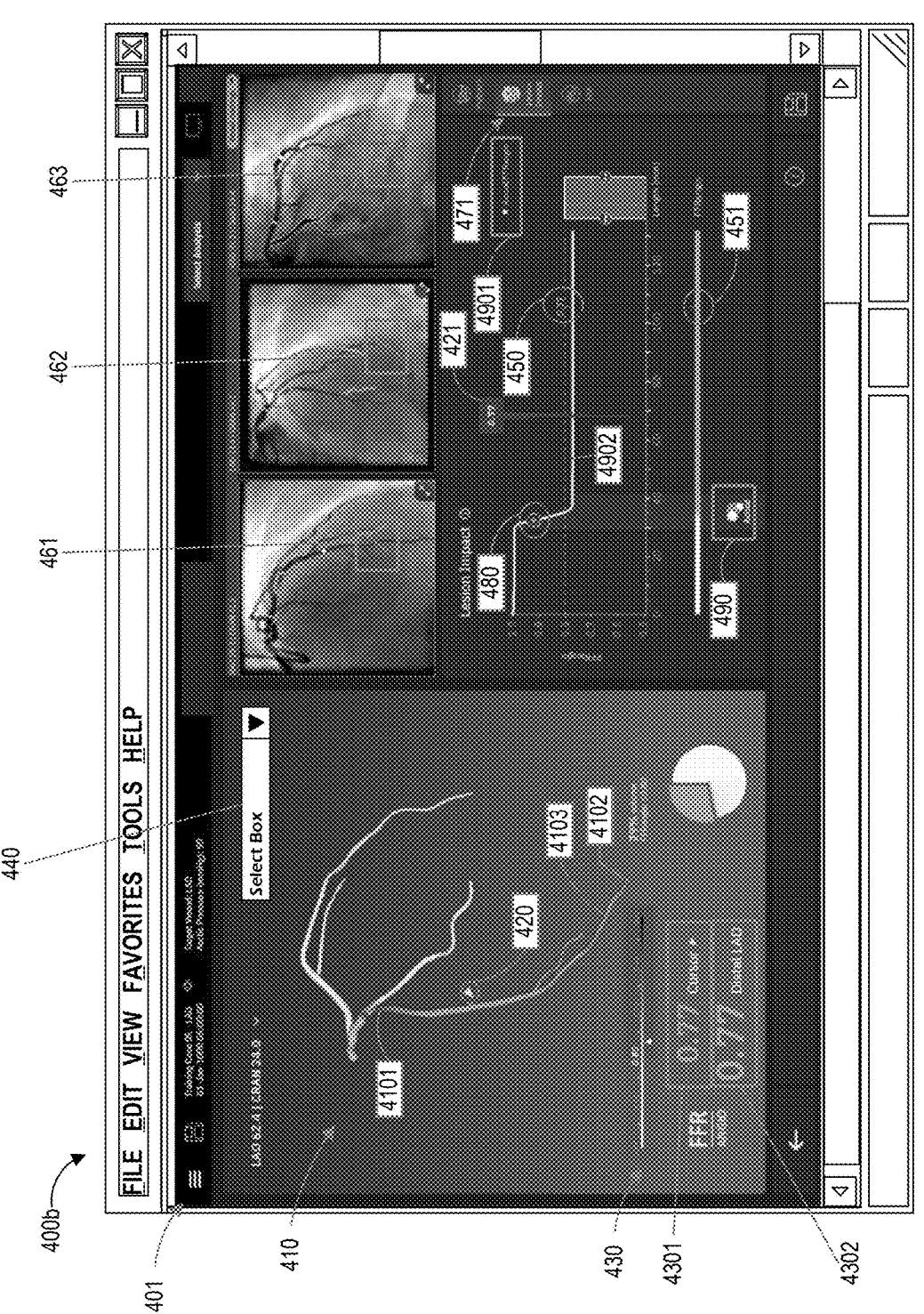
Figure 1D:
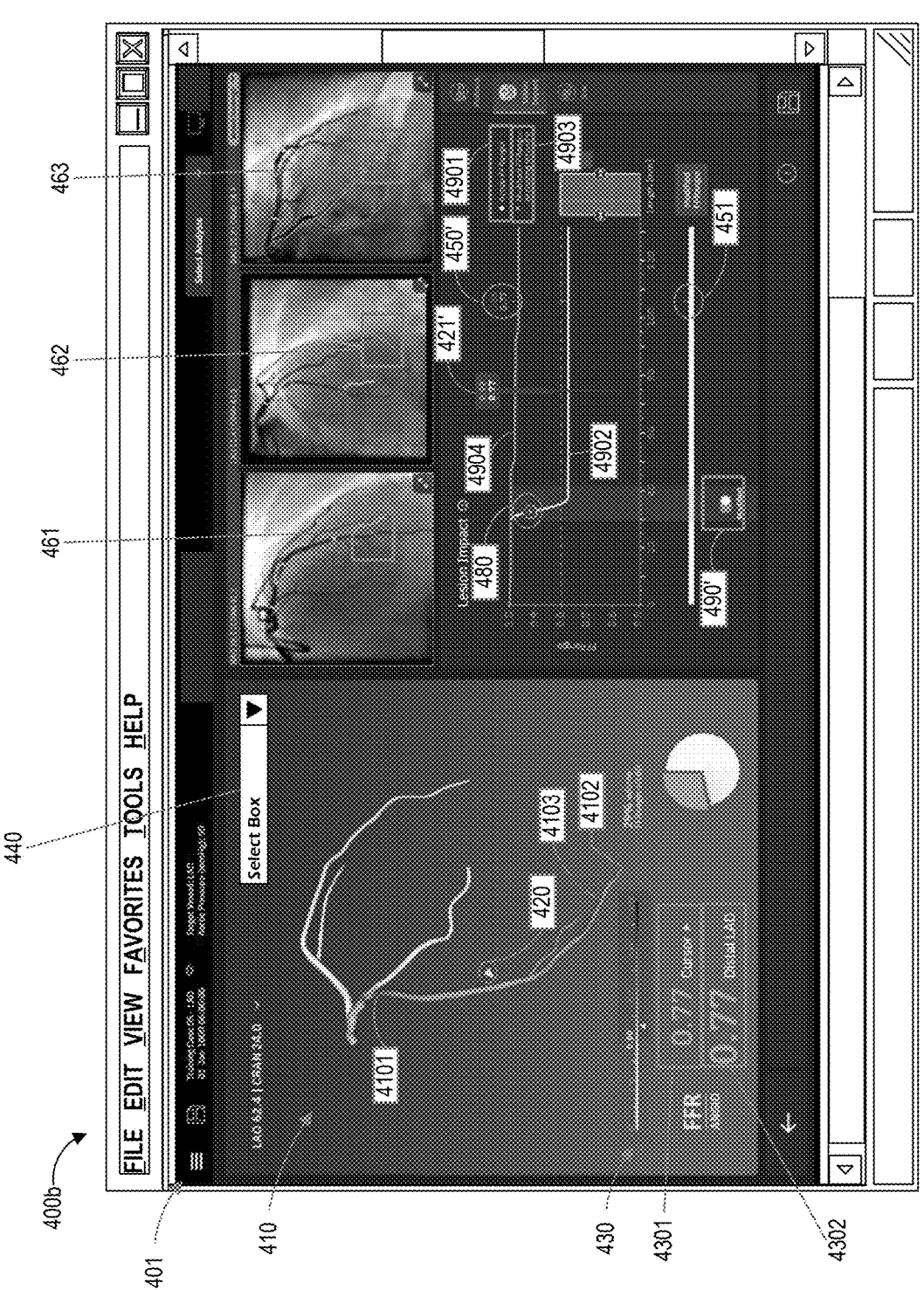

As illustrated in FIGS. 1C and 1D, the user interface 400c may include a second selectable parameter 471. The second selectable parameter 471 may include a lesion impact icon. In some cases, when the interface 401 receives an input to select the second selectable parameter 471, the interface 401 may display a lesion impact curve. The lesion impact curve may display an estimated adjustment to FFR values according to a cardiac response with and without a lesion, for example, displaying an actual FFR curve as compared to an estimated FFR curve (in response to removal of the effects of the lesion). In some cases, the interface 401 may include an FFR toggle 490. Adjustments of the FFR toggle 490 may cause the interface 401 to display various elements. For example, in a first toggle position, the interface 401 displays the actual FFR curve, and in a second toggle position, the interface 401 displays the estimated FFR curve. In some examples, the interface 401 as shown in FIG. 1C may correspond to the FFR toggle 490 being in a first toggle position. In this way, the lesion impact curve may include an actual FFR notification 4901 and a first FFR curve 4902.

The interface 401 as shown in FIG. 1D may correspond to the FFR toggle 490' being in a second toggle position. The lesion impact curve, in this example, may include the actual FFR notification 4901, a modified FFR notification 4903, the first FFR curve 4902, and a second FFR curve 4904. As illustrated in FIG. 1D, the system may update the vessel length marker 421' to indicate FFR values along the second FFR curve 4904 and depict a first FFR value and a second FFR value. The first FFR value may include a measured FFR value (may be referred to herein as "actual FFR value"). The second FFR value may include an estimated FFR value (may be referred to herein as "modified FFR value"). In some cases, the interface 401 may include the first FFR value in any position along the interface 401 (for example, vertically aligned and positioned below the second FFR value). In some examples, the interface 401 may include the second FFR value in any position along the interface 401 (for example, vertically aligned and positioned above the first FFR value).

As illustrated in FIG. 1D, the system may update the first distal marker 450' to indicate distal FFR values along the second FFR curve 4904 and depict a first distal FFR value and a second distal FFR value. The first distal FFR value may include a measured distal FFR value (may be referred to herein as "actual distal FFR value"). The second distal FFR value may include an estimated distal FFR value (may be referred to herein as "modified distal FFR value"). In some cases, the interface 401 may include the first distal FFR value in any position along the interface 401 (for example, vertically aligned and positioned below the second distal FFR value). In some examples, the interface 401 may include the second distal FFR value in any position along the interface 401 (for example, vertically aligned and positioned above the first distal FFR value).

Figure 1E:
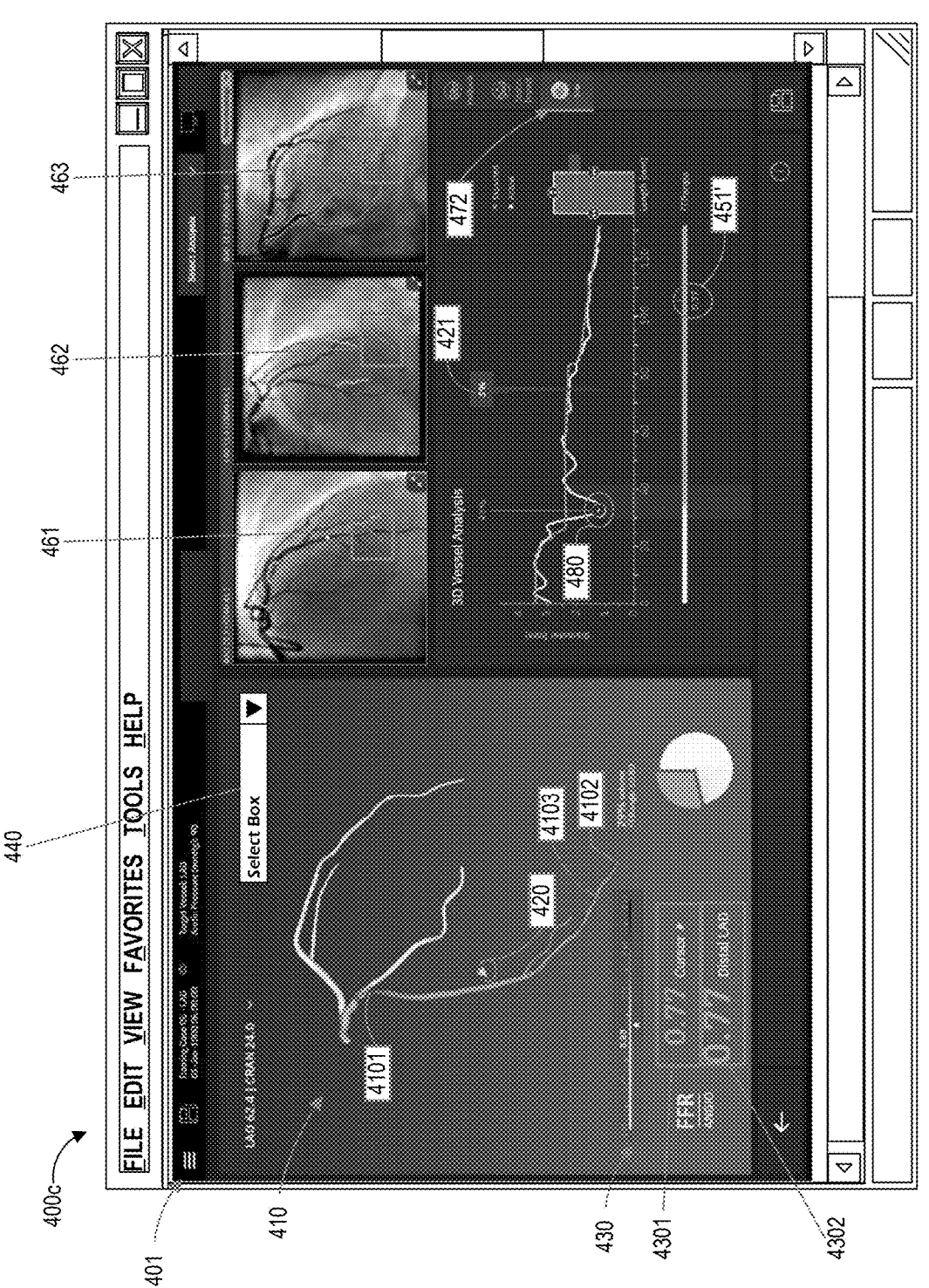

As illustrated in FIG. 1E, the user interface 400c may include a third selectable parameter 472. The third selectable parameter 472 may include a size icon. In some cases, when the interface 401 receives an input to select the third selectable parameter 472, the interface 401 may display a size curve. The size curve may display a geometric characteristic value of the vessel 410. For example, the size curve may include an X-axis corresponding to a length along the vessel 410 and a Y-axis corresponding to a diameter of the vessel 410. As illustrated in FIG. 1E, the system may update the second distal marker 451' to indicate distal FFR values along a one-dimensional graphic indicating FFR values, as disclosed herein.

Block Diagram—Flow Value Index Display

Figure 2:
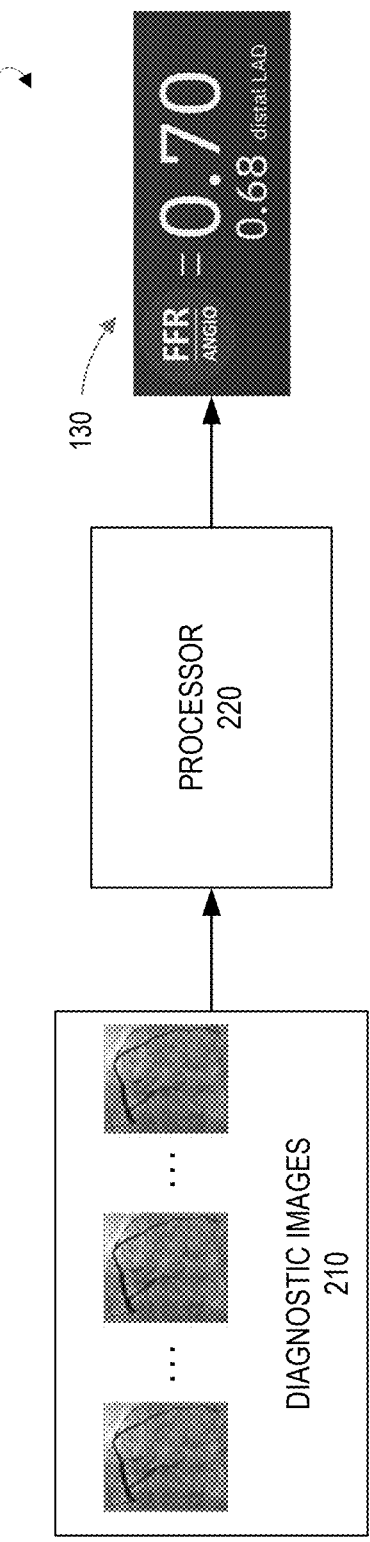
FIG. 2 illustrates a block diagram of an example vascular information display system.

FIG. 2 illustrates an example of a system 200 for vascular assessment. The system 200 may include diagnostic images 210, a processor 220, and a parameter display 130. The diagnostic images 210 may serve as the input for the system 200, capturing a portion of a subject's vasculature. In some examples, the diagnostic images 210 may include angiographic images. The system 200 may automatically select the diagnostic images 210 from a set of diagnostic images. For example, the system 200 may apply image analysis techniques to identify the diagnostic images 210 for vascular assessment. The system 200 can analyze a series of images and automatically choose the ones that provide an optimal visualization of the vessels of interest. In some cases, the system 200 may receive an input from a user for selecting the diagnostic images 210. The user may review a set of available images and select the ones that provide the most suitable visual characteristics for accurate assessment. In this manner, the system 200 may provide the user an interface to select the images manually. In some examples, the visual characteristics can include factors such as the angle of view, where specific angles are preferred to visualize the vessel and its surrounding structures. Example techniques to identify angles for the diagnostic images 210 are described in U.S. Pat. No. 10,595,807 and incorporated herein by reference in its entirety. Example techniques to determine optimal images are described in U.S. Patent Pub. 2023/0252632 which is hereby incorporated herein by reference in its entirety.

The number of diagnostic images 210 in the system 200 can vary depending on the implementation. In some examples, the system 200 may obtain a predetermined number of images. For example, the system 200 may obtain between approximately 1 and approximately 100 diagnostic images. The system 200 may obtain a predetermined number of images based on the vascular assessment and the desired level of detail needed for accurate diagnosis. In some instances, the system 200 may impose limitations on the number of diagnostic images 210 that can be processed. The limitations can be set to ensure optimal performance and efficient use of system resources. For example, the system 200 may limit the number of diagnostic images to prevent constraining computational resources for the system 200, the processing capabilities of the system 200, and/or to maintain real-time responsiveness for the system 200. Additionally, the number of diagnostic images 210 may be influenced by the memory capacity of the system 200. The system 200 may have a finite amount of memory available for storing and processing the images. As a result, the number of diagnostic images that can be accommodated may be constrained by the available memory resources for the system 200. By considering factors such as the desired level of detail, system performance, and memory limitations, the system 200 can manage and process the diagnostic images 210. This ensures that the system 200 operates efficiently and provides accurate and reliable results for the vascular assessment process. Regardless of the selection method, the diagnostic images 210 may provide visual information for the assessment of the vasculature. The diagnostic images 210 may serve as the foundation for subsequent processing and analysis by the system 200, enabling the calculation of flow index values and the generation of a three-dimensional vascular model.

The processor 220 may receive the diagnostic images 210 and extract vascular parameters, such as vessels, of the diagnostic images 210. In some examples, the processor 220 may extract the vascular parameters by applying image segmentation, feature extraction, and/or other image processing techniques to identify and analyze the vessels of interest. For example, the processor 220 may segment the diagnostic images 210, which may involve separating the vasculature from the surrounding tissues and background in the diagnostic images 210. This segmentation process may allow the processor 220 to isolate the vessels of interest and create a distinct representation for further analysis. In some examples, the processor 220 can extract various vascular parameters from segmented (or non-segmented) images. The vascular parameters may include vessel diameter, vessel length, tortuosity, plaque burden, or other relevant metrics that provide insights into the vascular health and functionality. In some examples, the processor 220 may apply feature extraction techniques to identify features (such as characteristics or landmarks) within the vasculature. The features can include bifurcations, stenoses, or other anatomical structures that may be used for assessing the severity of any potential obstructions or abnormalities. In some examples, the processor 220 may compute mathematical models and algorithms to calculate flow index values, such as FFR values, as disclosed herein. The computations performed by the processor 220 may provide accurate and reliable vascular parameters that aid in the assessment and diagnosis of vascular conditions. The parameters may serve as valuable information for users to make informed decisions regarding treatment strategies and patient care.

The parameter display 130 may receive the processed data from the processor 220 and present the flow index values and other relevant information. The parameter display 130 may provide a visual representation of the vascular assessment results, allowing the user to interpret and analyze the vascular health and functionality. The parameter display 130 may provide a comprehensive visualization of the vascular parameters. In some examples, the parameter display 130 may display both the FFR value and the distal FFR value. For example, the parameter display 130 may display both values, which may allow the user to rapidly diagnose the patient and interpret the significance of the values. The parameter display 130 may present the FFR value. By displaying the FFR value, the parameter display 130 may provide an efficient display of vascular information to the user for assessing the severity of the condition and make informed treatment decisions. In addition to the FFR value, the parameter display 130 may also display the distal FFR value. The distal FFR value corresponds to the FFR measurement at the predetermined distal point along the vessel. By displaying both the FFR value and the distal FFR value, the parameter display 130 may enable the user to compare and evaluate the impact of lesions or obstructions along the vessel's length. The simultaneous display of both the FFR value and the distal FFR value on the parameter display 130 may allow the user to quickly interpret the values and gain a comprehensive understanding of the vascular condition.

Example Flowchart—Flow Value Index Display

FIG. 3 is a flowchart of an example process 300 for displaying FFR values for a patient. For convenience, process 300 will be described as being performed by a system of one or more computers (e.g., the system 200 in FIG. 2).

At block 302, the system may receive a plurality of medical images that image a portion of a vasculature of a subject. In some examples, the system may receive a set of medical images, such as CT scans, MRI scans, or another medical procedure that captures a portion of the subject's vasculature. In this manner, the images may be obtained using imaging equipment and techniques described in FIG. 2. The received images may serve as the input for the subsequent steps disclosed herein.

At block 304, the system may produce a three-dimensional vascular model of the portion of the vasculature. Building upon the diagnostic images received in block 302, the system processes the images to produce a three-dimensional vascular model. The model, as described in FIG. 2, may represent the captured portion of the vasculature and provides a comprehensive visualization of the vessels of interest. Example techniques to generate the model are described in U.S. Pat. No. 10,595,807 and incorporated herein by reference in its entirety.

At block 306, the system may calculate flow index values that quantify vascular function along each of the vessels. Using the three-dimensional vascular model generated in block 304, the system may perform calculations to determine flow index values (e.g., FFR values). These values, as described in FIG. 2, may quantify the vascular function along each of the vessels within the model. The calculations may involve analyzing blood flow patterns, vessel geometry, and other factors to assess the hemodynamic significance of any potential stenosis or blockages.

At block 308, the system may display a representation of the three-dimensional vascular model comprising the vessels. In some examples, the system may present a visual representation of the three-dimensional vascular model generated in block 304. This representation, as described in FIG. 2, may include interactive visualizations, such as color-coded maps or graphs, that provide a comprehensive view of the vasculature. The display allows the user to assess the vessel's morphology, identify any abnormalities, and gain insights into the overall vascular health.

At block 310, the system may simultaneously display the flow value index for a designated location of the designated vessel along with the flow value index for a predetermined distal location along the length of the designated vessel. In some examples, the system may simultaneously display the flow value index for a designated location on the vessel, as identified in FIG. 1, along with the flow value index for a predetermined distal location along the length of the vessel. This simultaneous display allows the user to compare and evaluate the impact of lesions or obstructions along the vessel's length. By visualizing the flow value indexes side by side, the user can gain insights into the severity and location of potential abnormalities and make informed decisions regarding treatment strategies.

Example User Interface—QR Code

Figure 4A:
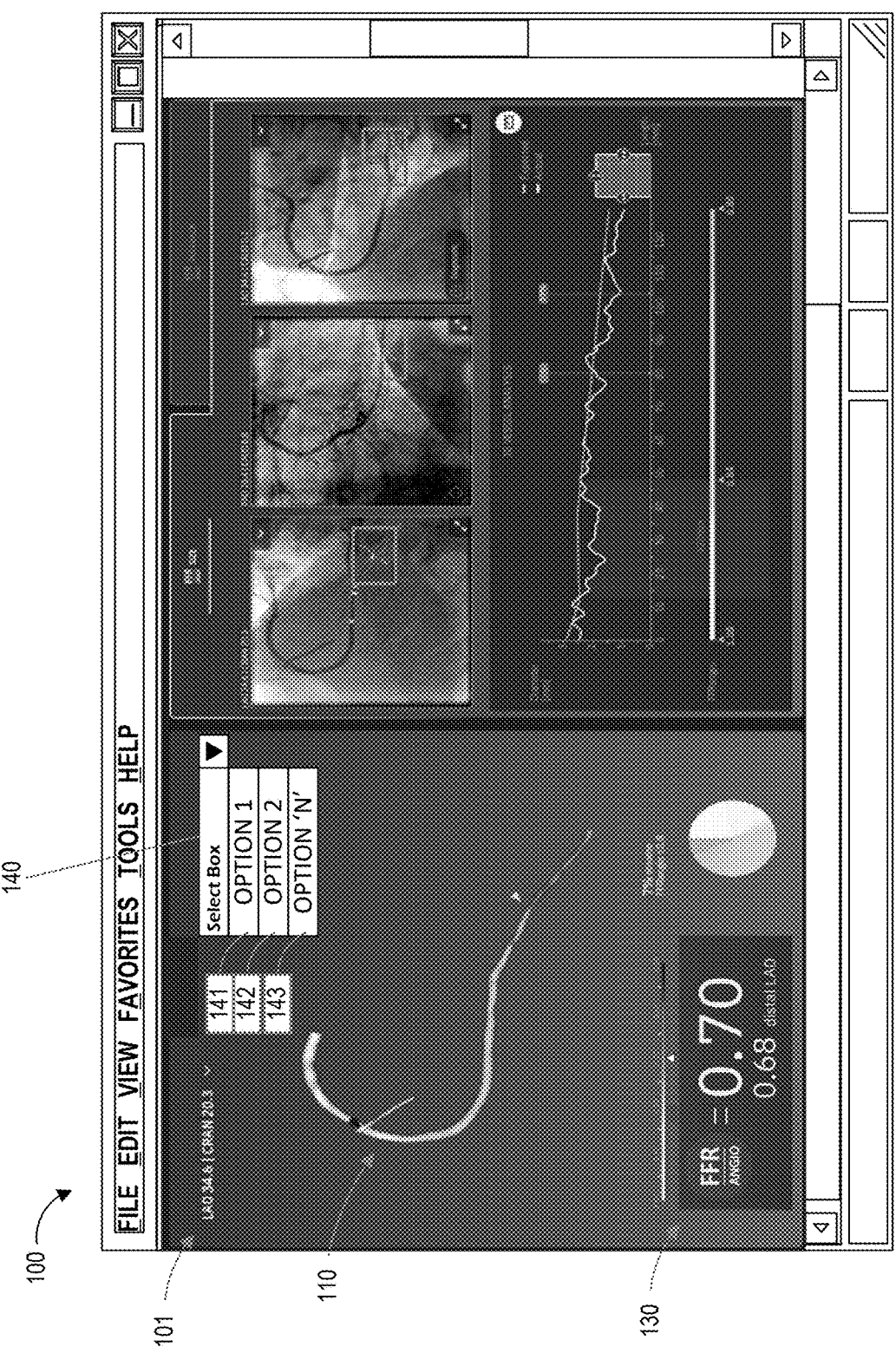
FIG. 4A illustrates a user interface for displaying vascular information for a patient, including a QR code selection interface.

FIG. 4A illustrates an example embodiment of a user interface 100 for vascular assessment. The user interface 100 includes an interface 101, a vessel 110, a parameter display 130, and a select box 140 with options including a first option 141, a second option 142, and an nth option 143. The interface 101 may be a graphical user interface (GUI) that allows users to interact with the user interface 100. The interface 101 may provide a platform to receive input commands, view visualization requests, and access requests to various functionalities. The interface 101 may be similar to the interface as disclosed herein (such as the interface 101 in FIG. 1). The interface 101 may provide for the user to interact with the application and access various features and functionalities. The interface 101 may receive inputs from devices such as a mouse, keyboard, or touch screen. The interface 101 may include graphical elements, buttons, menus, and input fields that the user can interact with to perform different actions. For example, the interface 101 may receive an instruction from the user to select a vessel 110 from the displayed representation of the three-dimensional vascular model. In this manner, the interface 101 may receive an action by the user, such as clicking or tapping on the vessel 110 in the interface 101. The interface 101 may display the selected vessel 110 by highlighting or visually indicating the vessel to show that the vessel has been chosen. The interface 101 may include a parameter display 130, which can show various information related to the selected vessel 110. This information may include flow value index, FFR value, and distal FFR value. The parameter display 130 can be updated in real-time as the user interacts with the application. Additionally, the interface 101 may include a select box 140 that allows the user to choose different options or settings related to the displayed vascular information.

As described herein, the vessel 110 is a three-dimensional model that represents a portion of a subject's vasculature. The vessel may be generated based on medical images, such as angiographic images, using image processing and reconstruction techniques. The vessel 110 accurately depicts the anatomical structure of the vasculature, including the arteries, veins, and their branching patterns. The vessel 110 may be similar to the vessel as disclosed herein (such as the vessel 110 in FIG. 1).

The parameter display 130 presents calculated flow index values and other relevant parameters derived from the analysis of the vessel 110. It may include visual representations such as graphs, charts, or color-coded maps to convey the information effectively. The parameter display 130 provides a comprehensive view of the vascular assessment results, allowing users to interpret and analyze the data. The parameter display 130 may be similar to the parameter display 130 as disclosed herein (such as parameter display 130 in FIG. 1).

The select box 140 may be an interface element to receive an input. In some examples, the select box 140 may display options for customization and control within the user interface 100. The select box 140 can include display options such as different views, analysis modes, or measurement parameters. The select box 140 may receive an input from the user to select an option. For example, by clicking or tapping on the corresponding option in the select box 140. In this manner, the select box 140 corresponds to inputs that cause the system to generate a QR code associated with various options. For example, the various options may include cardiac analysis, system logs, screenshots, and reports. In this way, the select box 140 may allow users to choose between different modes, settings, or parameters that affect the analysis or display of the vascular assessment. The options, such as the first option 141, second option 142, third option 143, provide flexibility and adaptability to meet specific user requirements.

The first option 141 in the select box 140 may correspond to a QR code generated for log reporting purposes. When this option is selected, the user interface 100 may generate a QR code that includes information intended for support teams to debug system errors. The QR code may include network information, log data, and other relevant data that can assist in identifying and resolving issues within the system. The QR code corresponding to the first option 141 may allow the support teams to quickly access the information for debugging and troubleshooting purposes.

The second option 142 in the select box 140 may correspond to an interface QR code. For example, the interface QR code may encode a snapshot of the interface 101 at the moment the second option 142 is selected.

The third option 143 in the select box 140 may correspond to a medical information QR code. When this option is selected, the user interface 100 may generate a QR code that includes information which forms the interactive user interface 100. For example, in contrast to the second option 142, the third option 143 may enable an end-user to view a similar user interface 100. As an example, the QR code may encode mappings between FFR values and positions along the vessel (e.g., lengths along the vessel). The information may additionally include a geometrical representation of the three-dimensional model. The information may additionally include the distal FFR value described herein. In some embodiments, the QR code may encode a subset of the information. For example, the mapping between FFR value and length may be encoded (e.g., as a CSV value or other format). An end-user device may obtain the mapping from the QR code, and a user of the end-user device may understand how FFR values change along the length of the vessel.

Advantageously, the system may remove protected health information (PHI) associated with a patient. For example, the system may analyze the information included in interface 100 and remove information from categories associated with PHI. As another example, when the user of user interface 100 selects an option to share the underlying information which forms the interface 100, the system may analyze the information to remove any PHI.

Figure 4B:
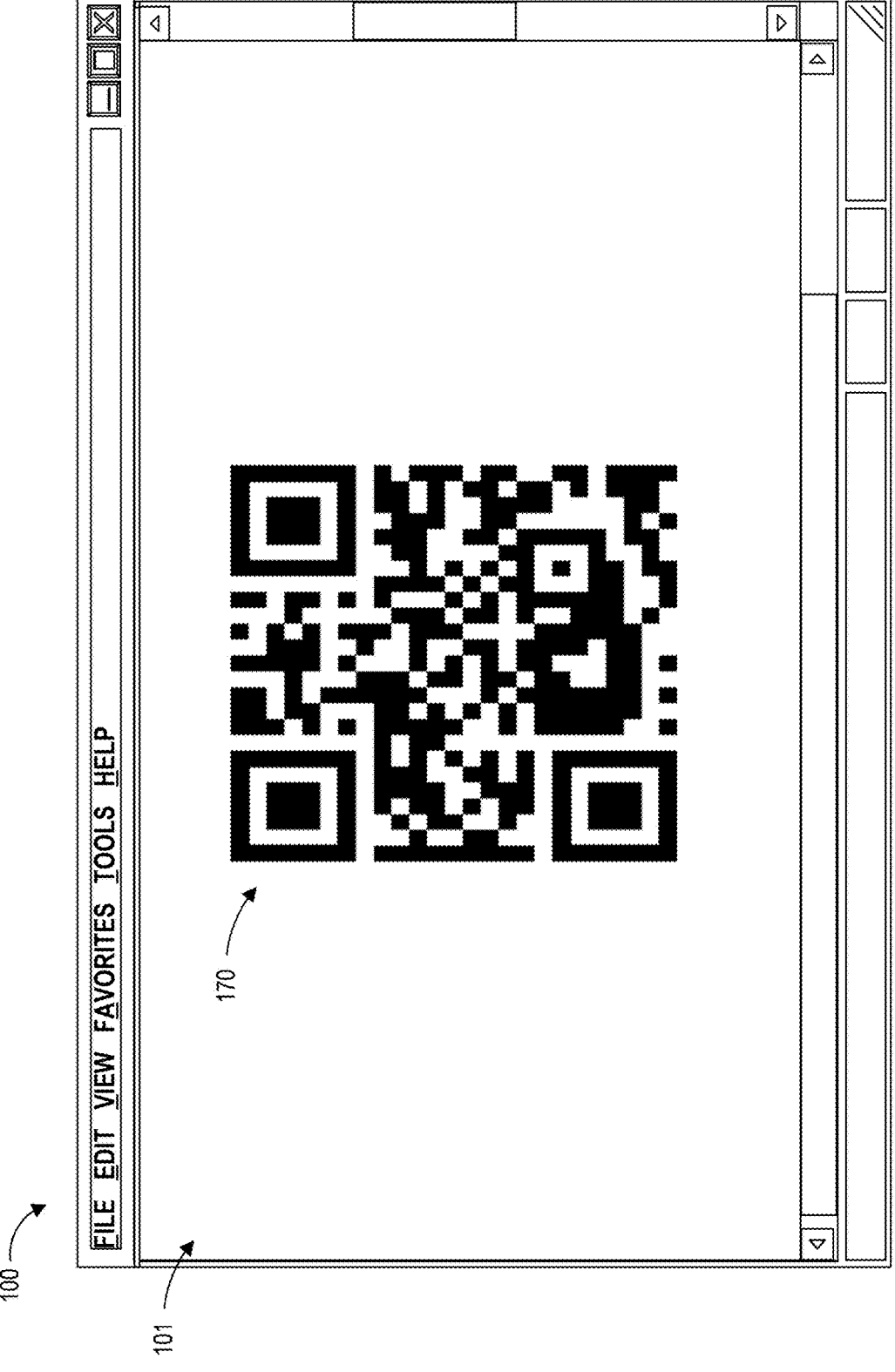
FIG. 4B illustrates a user interface for displaying an QR code, such as a debugging QR code or a medical information QR code.

FIG. 4B depicts an example of a QR code 170 displayed on user interface 100. As described above, a user may select an option (e.g., example box 140), and the user interface 100 may update to present QR code 170. In some examples, the QR code 170 is displayed in the entirety of the display screen, occupying the entire available space. This allows for a clear and easily scannable QR code 170. In other examples, the user interface 100 may display the QR code 170 along a portion of the interface 101. In some examples, as illustrated, the QR code 170 captures an entirety of the interface 101. In some examples, the QR code 170 may be displayed alongside other information or interface elements. The arrangement provides flexibility in the interface 101 of the user interface 100 and allows for efficient use of screen real estate.

While a single QR code 170 is illustrated, in some embodiments there may be 2, 4, 8 QR codes which collectively encode information. Additionally, the QR code(s) may be cycled, or otherwise adjusted, at a particular frame rate (e.g., 5 Hz, 10 Hz, 24 Hz). In this way, the QR codes may encode substantially greater quantities of data. An end-user device may take images at a particular framerate, such as via video, and analyze the images to identify unique QR codes presented via interface 100.

The QR code 170 may serve as a visual representation of encoded information related to the selected option. When scanned by a device equipped with a camera and appropriate decoding software, the QR code 170 can be processed to retrieve the information as disclosed with respect to the options from the select box (such as select box 140). This information may include data relevant to the FFR calculations, such as medical images, vascular model information, or analysis results. By displaying the QR code 170, the user interface 100 enables users to easily capture and transfer the encoded information to other devices or systems. This facilitates seamless sharing, collaboration, or further analysis of the FFR calculations performed by the system.

In some examples, the QR code 170 may be encoded corresponding to a security scheme. For example, the QR code 170 may include a number of pixels corresponding to an encryption protocol. In some examples, on at least one edge of the QR code 170, the QR code 170 may include between 5 and 177 pixels. In some examples, the QR code 170 may comply with applicable standards. For example, the QR code 170 may comply with ISO/IEC 18004:2015 and/or ISO/IEC 23941:2022, or another standard applicable. In some examples, the QR code 170 may be version 1 to version 40. In some examples, the QR code 170 may be square, rectangular, circular, or another two-dimensional or three-dimensional shape. In some examples, the QR code 170 may be black and white (or any other combination of colors).

Block Diagram—QR Code

Figure 5:
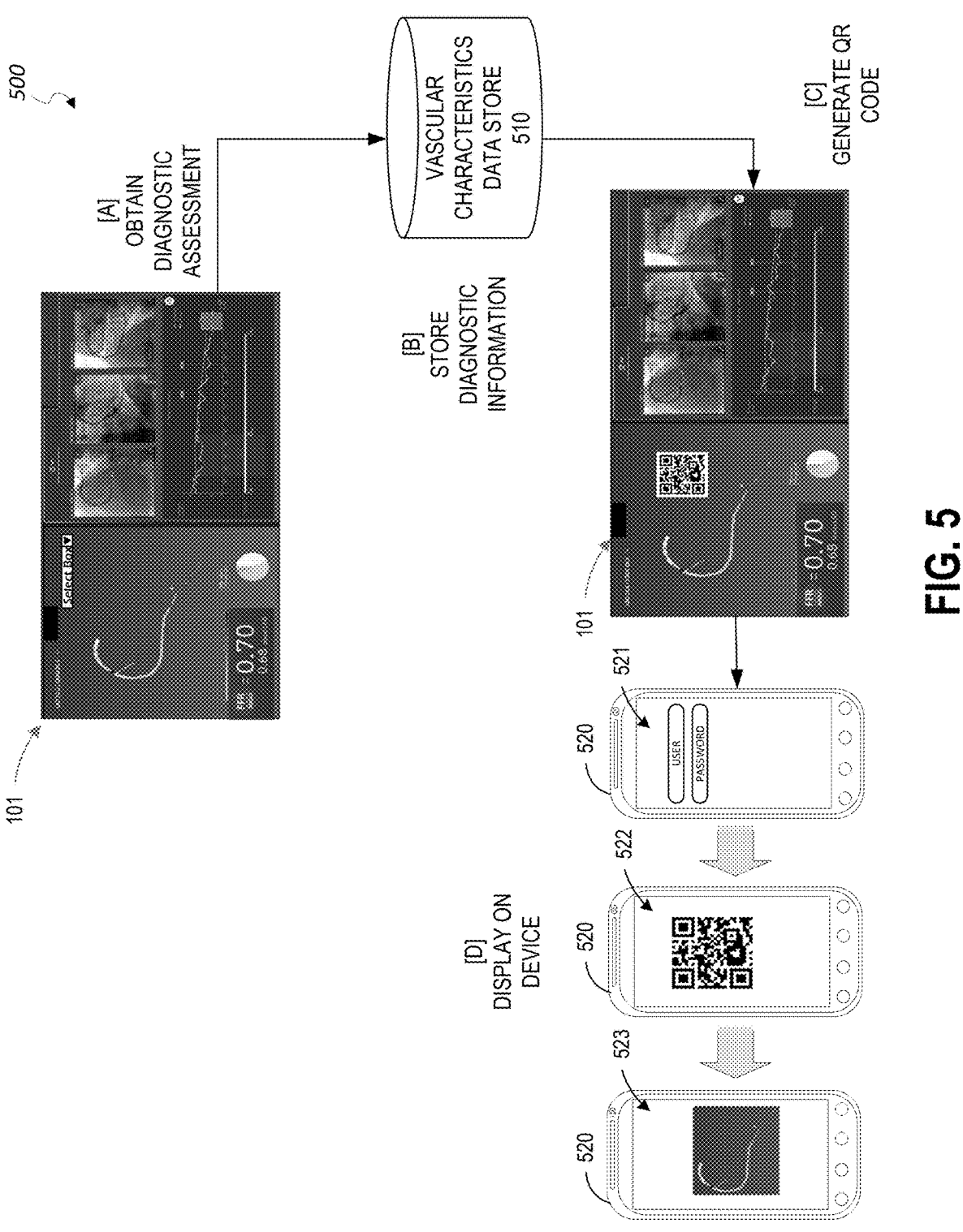
FIG. 5 illustrates a block diagram of an example QR code generation system and capturing the QR code on a device.

FIG. 5 illustrates one example of a system 500 for displaying vascular information on a device 520. The system 500 includes a vascular characteristics data store 510, a device 520 with a first screen 521, a second screen 522, and a third screen 523. The vascular characteristics data store 510 may store diagnostic information obtained from a diagnostic assessment. The device 520 may receive input to capture and/or receive a QR code. The first screen 521 of the device 520 may optionally prompt for user authentication, the second screen 522 may display the QR code, and the third screen 523 may display the information.

The vascular characteristics data store 510 may serve as a repository for storing vascular characteristic data obtained from a diagnostic assessment. The vascular characteristic data may include information related to the characteristics and properties of the vasculature being assessed. The vascular characteristic data can include medical images, three-dimensional vascular models, flow index values, FFR values, and other relevant parameters. The vascular characteristics data store 510 may receive the vascular characteristic data from various sources, such as imaging devices, diagnostic software, or other systems involved in the diagnostic assessment process. The data may be generated through techniques like medical imaging, computational modeling, or physiological measurements. The vascular characteristics data store 510 may apply data encryption, access control mechanisms, backup and recovery procedures, and compliance with relevant data protection regulations. The stored data can be retrieved and utilized by the interface 101 to generate QR codes, display vascular information, and facilitate secure data transfer. The vascular characteristics data store 510 may interact with the interface 101 to provide the data for generating and displaying the QR code.

The device 520 may interface between a user and the vascular information. In some examples, the device 520 may represent a computing device that can be a smartphone, tablet, laptop, or any other suitable device capable of displaying the vascular information and interacting with the system. The specific type of device may vary depending on the implementation and user preferences. The device 520 may receive an input to launch an application (such as a medical information display application). In this manner, the device 520 may prompt a user to enter authentication credentials (as illustrated with the first screen 521). In this manner, the application operating on the device 520 may allow for secure and efficient transfer of data to authorized users. In some examples, the application operating on the device 520 may include an ability to display medical information associated to a patient. In some examples, the application may prompt the user to capture an image of a QR code to access medical information for display. The device 520 may obtain the QR code through various means, depending on the system 500 design and user requirements. The goal is to provide users with convenient and flexible options for accessing and sharing the QR code and the associated vascular information.

The first screen 521 of the device 520 prompts for user authentication. In some examples, the device 520 is operating the application which may provide a secure login interface where users can enter their credentials, such as a username and password, to gain access to the application. In some examples, the device 520 may be connected to a hospital communication network (such as a hospital server). For example, the device 520 may have a wireless, wired, virtual connection to the hospital communication network. In some examples, the device 520 may connect to a virtual private network (VPN) established by the hospital communication network, such that the user may be able to access medical information. The authentication step ensures that only authorized individuals can view and interact with the sensitive data. The first screen 521 in FIG. 5 represents a prompt for user authentication to access an application that displays the vascular data. The first screen 521 may serve as a secure login interface where users are required to authenticate themselves before gaining access to the application and the associated vascular data.

The second screen 522 illustrates the device 520 capturing the QR code data when the interface 101 displays the QR code. There are several methods by which the device 520 can capture the QR code data. In some examples, the device 520 may capture the QR code with a camera. The device 520 may have a built-in camera that allows users to capture the QR code data. The user can open the application and navigate to the QR code scanning feature. The device's camera can then be activated, and the user can position the camera to align with the QR code displayed on a screen or physical medium. The camera captures the QR code image, and the application processes the image to extract the encoded data. In some examples, the device may capture the QR code by scanning the QR scan from within an application operating on the device. The application running on the device 520 may have a built-in QR code scanning feature. The user can open the application, navigate to the scanning feature, and activate it. The application's scanning feature utilizes the device's camera to capture the QR code image. The application then processes the image to extract the encoded data.

In some examples, the device may capture the QR code by image upload. The user may capture the QR code image using a separate device, such as a digital camera or another smartphone. The user can then transfer the image file to the device 520, either by connecting the devices or by uploading the image file to the device through a file-sharing platform or email. Once the image file is on the device 520, the application can access and process the image to extract the QR code data.

In some examples, the device may capture the QR code by screen capture. The user may capture a screenshot of the QR code displayed on another device or screen. The device 520 allows users to capture screenshots by pressing specific buttons or using gesture controls. Once the screenshot is captured, the user can open the application and navigate to the QR code scanning feature. The application can then access the screenshot image and process it to extract the QR code data.

The third screen 523 illustrates the device 520 displaying vascular information. The third display screen 523 may present the diagnostic information in a user-friendly format, allowing healthcare professionals to review and interpret the data effectively. In some examples, the third screen 523 may include visualizations, charts, graphs, reports, or textual information to provide a comprehensive overview of the vascular characteristics. The specific information the device 520 displays on the third screen 523 can vary depending on the application and the nature of the vascular assessment. In some examples, the device 520 may display information on the third screen 523 which may be static, dynamic, or a combination of static and dynamic.

In some examples, the third screen 523 may display three-dimensional model. The third screen 523 may present a three-dimensional model of the vasculature, allowing users to visualize the structure and geometry of the blood vessels. This model can provide a detailed representation of the vascular system, including the arteries, veins, and their branching patterns. In some examples, the third screen 523 may display flow index values. The screen can display flow index values that quantify vascular function along the vessels. These values may be calculated based on the three-dimensional model and provide insights into blood flow characteristics, such as velocity, pressure, or resistance. In some examples, the third screen 523 may display lesion analysis. In some examples, the device 520 may display the flow index values as described herein (such as with the parameter display 130, flow value index 1301, and distal flow value index as disclosed in at least FIGS. 1, 2, and 4A). If the vascular assessment involves lesion analysis, the third screen 523 may highlight specific areas of interest, such as stenoses or plaques. The third screen 523 can display detailed information about these lesions, including their location, severity, and impact on blood flow. In some examples, the third screen 523 may display graphs and charts.

The third screen 523 may include graphical representations, such as line graphs or bar charts, to visualize trends or comparisons in the vascular data. These graphs can provide a visual summary of parameters like flow index values, vessel diameter, or lesion characteristics. In some examples, the third screen 523 may display annotations and markers. The device 520 may have the ability to add annotations or markers to the vascular data on the third screen 523. These annotations can help highlight specific points of interest or provide additional context for analysis. In some examples, the third screen 523 may display interactive features. The third screen 523 may offer interactive functionality, allowing users to manipulate the vascular data. For example, users may be able to rotate, zoom, or navigate through the three-dimensional model to explore different perspectives. They may also have the ability to adjust parameters or toggle between different views to customize the display according to their preferences. In some examples, updating or annotating the vascular data (or other information) from the device 520 may update information of the vascular characteristics data store 510. For example, the device 520 may generate QR code(s) that encode changes and the system described above may capture images of the QR code(s) to effectuate the changes.

In some examples, the third screen 523 may display static full analysis report page. The full analysis report page may include detailed information about the patient. The screen can provide detailed information about the patient's vascular condition, including measurements, calculations, and diagnostic findings. This information can help healthcare professionals make informed decisions and plan appropriate treatment strategies. The third screen 523 may receive interactions from the user with the vascular information through various means, depending on the application's features and functionalities. The third screen 523 may receive interactions which can include touch gestures, mouse clicks, or keyboard inputs to navigate, zoom, or select specific elements of the vascular data. In some examples, the device 520 may export or share the displayed information.

In some examples, in response to the QR code being scanned, the system 500 may anonymize the information and send the anonymized information (such as, the report) to a remote or cloud-based storage system (such as, the vascular characteristics data store 510). In this way, the system 500 anonymizing and sending the information may reduce a document size from being sent over a network, for example, rather than texting, emailing, etc. the information. In some examples, the information may be downloaded (for example, by a user device) and then uploaded to the remote storage system. Storing the information in the remote storage system may allow for access to the information by various devices, providing increased accessibility to the information.

Example Flowcharts—QR Code

Figure 6:
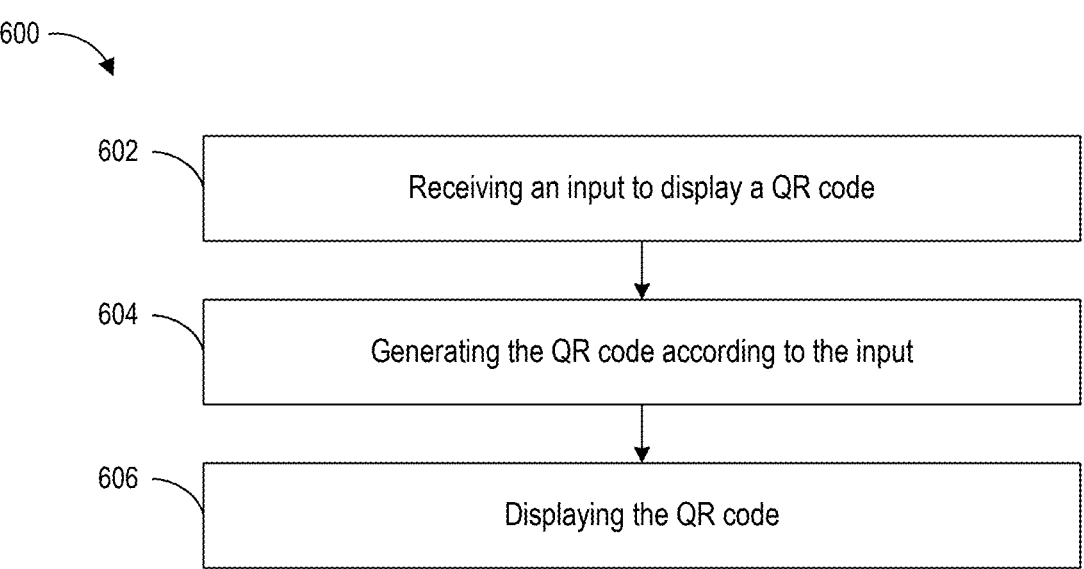
FIG. 6 illustrates a flow chart of another example process for generating and displaying a QR code.

FIG. 6 illustrates an example process 600 for generating a QR code for display on an interface. For convenience, process 600 will be described as being performed by a system of one or more computers (e.g., the system 500 in FIG. 5).

At step 602, the system may receive an input to display a QR code. The QR code, as described herein, may represent an animated QR code. The QR code may also include multiple QR codes presented at a same time. In some examples, the QR code may correspond to a debugging information, medical information, or another type of information. The system may apply the QR code techniques described herein (such as in FIG. 5).

At step 604, the system may generate the QR code according to the input. The system may generate the QR code for medical information and/or debugging information in response to the input received. The system may generate the QR code according to techniques described herein (such as in FIG. 5).

At step 606, the system may display the QR code. In some examples, the system may display the QR code on an interface (such as interface 101 in at least FIGS. 1, 2, 4A, 4B, and 5). The system may apply the QR code displaying techniques described herein (such as in FIG. 5).

Figure 7:
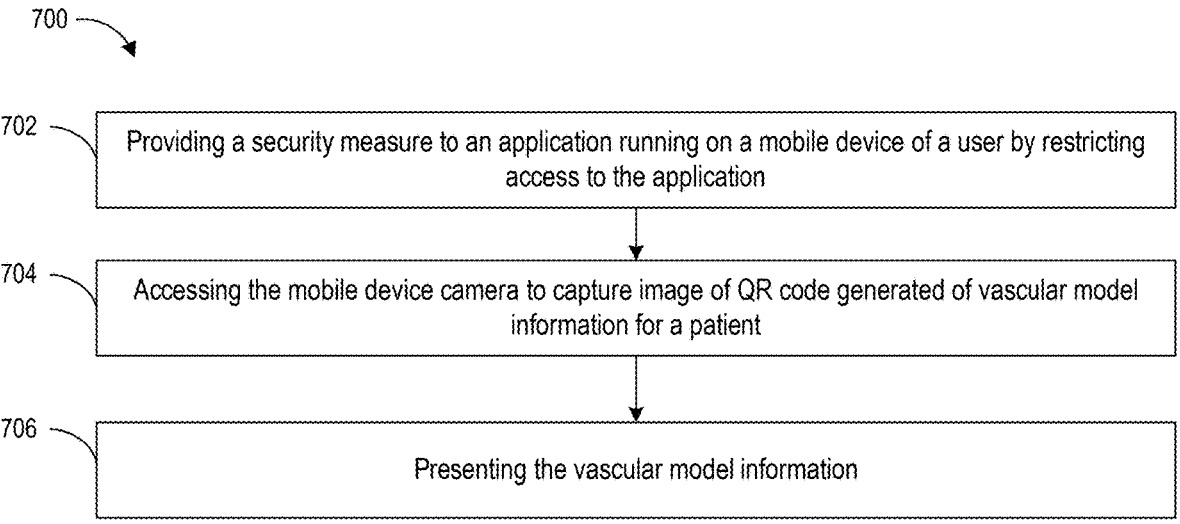
FIG. 7 illustrates a flow chart of another example process for displaying medical information on a device.

FIG. 7 illustrates an example process 700 for managing vascular model information on a mobile device. For convenience, process 700 will be described as being performed by a device (e.g., the device 520 in FIG. 5).

At step 702, the device may provide a security measure to an application running on a mobile device of a user by restricting access to the application. For example, the device may prompt a user to input a username and password as an authentication technique. In some examples, the device may connect to a network to obtain access to medical information. The device may restrict access to the application as disclosed herein (such as described in FIG. 5).

At step 704, the device may access the mobile device camera to capture image of QR code generated of vascular model information for a patient. In some examples, the QR code may encode a URL to establish communication between the device and a datastore. The device may access the camera to capture an image of the QR code as disclosed herein (such as described in FIG. 5).

At step 706, the device may present the vascular model information. In some examples, the device may display a vascular model in the form of a three-dimensional model. The device may present the vascular model information as disclosed herein (such as described in FIG. 5).

Three-Dimensional Sizing Tool

FIGS. 8A-8C illustrate examples of a three-dimensional sizing tool 802 which is presented on a three-dimensional model of a portion of a vasculature. The sizing tool 802 may surround a portion of the vasculature, with the portion being defined based on a range of lengths selected by the user. In some embodiments, the user may select the lengths using portion 804. For example, portion 804 maps geometrical information (e.g., vessel diameter) to length along the vessel. Thus, the portion 804 may extend along a same length as specified in portion 804.

The three-dimensional models described herein may be viewable at different orientations, such that a user may rotate, translate, or otherwise adjust the viewing perspective of the three-dimensional model. The sizing tool 802 may similarly be adjusted in viewing perspective based on adjustments to the three dimensional model. In this way, the sizing tool 802 may rotate, translate in the interface, and so on, in accordance with the model.

The sizing tool 802 may reflect, in some embodiments, the geometrical information included in portion 804. As an example, the shape or contour of the tool 802 may be based on diameters of individual portions of the vessel. As another example, the tool 802 may be adjusted in diameter in individual portions based on diameters of individual portions of the vessel. In this example, the tool 802 may be offset from the surface of the vessel by a same distance. As another example, the tool 802 may include concentric rings (e.g., ring 806) which is of a diameter based on a diameter of the vessel. For example, ring 806 may represent an average diameter for a subset of the lengths included in the range of lengths.

FIG. 8B illustrates the sizing tool 802 being moved to a bifurcation. For example, a user may have adjusted portion 804 to move the white shape (e.g., rectangle) to a different range of lengths. The white shape may thus be used to identify arbitrary ranges of lengths. The sizing tool 802 moves in conjunction with movement of the white shape in portion 804. At the bifurcation, the sizing tool 802 moves along the vessel heading down instead of along the vessel to the right of the bifurcation. The vessel may represent a vessel which is being analyzed, for example as depicted in portion 812. This portion 812 represents one of the medical images used to generate the three-dimensional model with colors reflecting the vessel being analyzed (e.g., red may indicate the particular vessel being analyzed). Thus, the system has automatically adjusted the sizing tool 802 to stick to the vessel being analyzed when portion 804 is updated.

FIG. 8C illustrates the three-dimensional model and sizing tool 802 described above. Portion 824 has been updated to select a different range of lengths. In this example, the interface is showing a mapping between FFR value and lengths of the vessel. For example, the user has selected option 828 to show a 'pullback' curve which depicts a mapping between individual FFR values and individual positions along the vessel.

On the three-dimensional model, a visual indicator 826 is included which reflects a position (e.g., a specific length) along the vessel of interest to the user. For this selected location (e.g., selected using selector 830), the FFR value 832A is included in the user interface proximate to the three-dimensional model. As described above, the distal FFR 832B value may additionally be shown.

With respect to option 828, the options in the illustrated example include a pullback curve, lesion impact, and a sizing tool. These options may be in a particular ordering which is useful to medical professionals. For example, the pullback curve may inform mappings between FFR and lengths along the vessel. The lesion impact may be used to cancel, or otherwise reduce the effects to substantially zero, of lesions in the vessel. As described herein, lesions may cause constrictions of vessels resulting in reduced diameters in potions of the vessels. Thus, the lesion impact may be used to 'turn' off a lesion, or lesions. The sizing tool may inform mappings between geometrical information (e.g., diameters) and lengths along the vessel.

In some embodiments, the system described herein may implement a process that includes presenting a user interface displaying a three-dimensional vascular model. The user interface may include a portion which visually maps FFR values and lengths along at least one vessel depicted in the vascular model. User input is received to select a particular length along the vessel. The user input may be received at the portion visually mapping the FFR values and lengths, and may include defining a shape (e.g., a rectangle or square) that extends between a range of lengths. The user interface is updated to present a three dimensional sizing tool or indicator along (e.g., surrounding) the vascular model.

In some examples, the three-dimensional model may have a co-registration with another image or model (e.g., a two-dimensional image of one or more vessels). The placement of a vessel may be challenging to identify as the vessels provided in a two-dimensional image may overlap with one another. For example, and with respect to bifurcations of a vessel, the co-registration may provide positioning of various vessels of the one or more vessel in three-dimensions (such as, geometric realignment of potentially overlapping vessels from the two-dimensional image). The co-registration between the two-dimensional image and the three-dimensional model may be able to show the bifurcation in relation to the other vessels of the one or more vessels. The separation of vessel placement may provide for increased accuracy in assessing vessel flow (such as, FFR values and other measurements as described herein). In some examples, the three-dimensional sizing tool 802 may extend along the three-dimensional model according to the co-registration between the three-dimensional model and the two-dimensional image.

Terminology and Additional Considerations

Some inventive aspects of the disclosure are set forth in the following clauses:

Clause 1. A method comprising: displaying a representation of a three-dimensional vascular model including a three-dimensional (3D) sizing tool that surrounds a portion of the three-dimensional vascular model, wherein the portion comprises a volume of the three-dimensional vascular model which is based on a mapping of geometrical information of one or more vessels which form the three-dimensional vascular model to a length along the portion; displaying an interface for adjusting the 3D sizing tool, wherein an area along the interface corresponds to a length of the 3D sizing tool; receiving input to adjust the length of the 3D sizing tool via the area along the interface; and adjusting the length of the 3D sizing tool according to the input.

Clause 2. The method of Clause 1, wherein the geometrical information includes at least one of vessel radius or vessel diameter.

Clause 3. The method of Clause 1, further comprising: receiving user input to adjust a position of the 3D sizing tool along the three-dimensional vascular model; and adjusting the position of the 3D sizing tool along the three-dimensional vascular model, wherein a visual appearance of the 3D sizing tool is adjusted based on geometrical information associated with the three-dimensional vascular model.

Clause 4. The method of Clause 3, further comprising adjusting the position along the three-dimensional vascular model in conjunction with movement of the area along the interface.

Clause 5. The method of Clause 1, further comprising displaying the mapping of geometrical information to the length along the portion in the interface.

Clause 6. The method of Clause 1, further comprising selecting, via the interface, a pullback curve to display a mapping between individual FFR values and individual positions along the three-dimensional vascular model.

Clause 7. The method of Clause 1, further comprising, based on the 3D sizing tool being adjusted along the three-dimensional vascular model and the 3D sizing tool surrounding a bifurcated vessel, adjusting a position of the 3D sizing tool along a first vessel, wherein the bifurcated vessel includes the first vessel and a second vessel.

Clause 8. A system comprising: a non-transitory data store storing computer-executable instructions; and a processor in communication with the non-transitory data store, wherein the computer-executable instructions, when executed by the processor, cause the processor to: display a representation of a three-dimensional vascular model including a three-dimensional (3D) sizing tool that surrounds a portion of the three-dimensional vascular model, wherein the portion comprises a volume of the three-dimensional vascular model for which to determine a mapping of geometrical information to a length along the portion; display an interface for adjusting the 3D sizing tool, wherein an area along the interface corresponds to a length of the 3D sizing tool; receive input to adjust the length of the 3D sizing tool via the area along the interface; and adjust the length of the 3D sizing tool according to the input.

Clause 9. The system of Clause 8, wherein the geometrical information includes at least one of radius, one or more vessel diameter.

Clause 10. The system of Clause 8, wherein the computer-executable instructions, when executed by the processor, cause the processor to: receive an input to adjust a position of the 3D sizing tool along the three-dimensional vascular model; and adjust the position along the three-dimensional vascular model.

Clause 11. The system of Clause 10, wherein the computer-executable instructions, when executed by the processor, cause the processor to adjust the position along the three-dimensional vascular model in conjunction with movement of the area along the interface.

Clause 12. The system of Clause 8, wherein the computer-executable instructions, when executed by the processor, cause the processor to display the mapping of geometrical information to the length along the portion in the interface.

Clause 13. The system of Clause 8, wherein the computer-executable instructions, when executed by the processor, cause the processor to select, via the interface, a pullback curve to display a mapping between individual FFR values and individual positions along the three-dimensional vascular model.

Clause 14. The system of Clause 8, wherein the computer-executable instructions, when executed by the processor, cause the processor to, when the 3D sizing tool is adjusted along the three-dimensional vascular model and the 3D sizing tool surrounds a bifurcated vessel, adjust a position of the 3D sizing tool along a first vessel, wherein the bifurcated vessel having the first vessel and a second vessel.

Clause 15. One or more non-transitory computer-readable media comprising computer-executable instructions that, when executed by a computing system, cause the computing system to: display a representation of a three-dimensional vascular model including a three-dimensional (3D) sizing tool that surrounds a portion of the three-dimensional vascular model, wherein the portion comprises a volume of the three-dimensional vascular model for which to determine a mapping of geometrical information to a length along the portion; display an interface for adjusting the 3D sizing tool, wherein an area along the interface corresponds to a length of the 3D sizing tool; receive input to adjust the length of the 3D sizing tool via the area along the interface; and adjust the length of the 3D sizing tool according to the input.

Clause 16. The one or more non-transitory computer-readable media of Clause 15, wherein the geometrical information includes at least one of radius, one or more vessel diameter.

Clause 17. The one or more non-transitory computer-readable media of Clause 15, further comprising: receiving an input to adjust a position of the 3D sizing tool along the three-dimensional vascular model; and adjusting the position along the three-dimensional vascular model.

Clause 18. The one or more non-transitory computer-readable media of Clause 17, further comprising adjusting the position along the three-dimensional vascular model in conjunction with movement of the area along the interface.

Clause 19. The one or more non-transitory computer-readable media of Clause 15, further comprising displaying the mapping of geometrical information to the length along the portion in the interface.

Clause 20. The one or more non-transitory computer-readable media of Clause 15, further comprising selecting, via the interface, a pullback curve to display a mapping between individual FFR values and individual positions along the three-dimensional vascular model.

Clause 21. A method for vascular assessment comprising: receiving a plurality of medical images imaging a portion of a vasculature of a subject, wherein the portion of the vasculature comprises one or more vessels; producing, by automatic processing of the medical images, a three-dimensional vascular model of the portion of the vasculature comprising the one or more vessels based on the medical images; calculating flow index values quantifying vascular function along each of the one or more vessels based on the three-dimensional vascular model; displaying a representation of the three-dimensional vascular model comprising the one or more vessels; and for a designated vessel of the one or more vessels, simultaneously displaying the flow value index for a designated location of the designated vessel along with the flow value index for a predetermined distal location along a length of the designated vessel.

Clause 22. The method of Clause 21, wherein the predetermined distal location is 80% of a length of the designated vessel.

Clause 23. The method of Clause 21, wherein the predetermined distal location is located at 80% of a length of the designated vessel, measured from a proximal end of the designated vessel.

Clause 24. The method of Clause 21, wherein the predetermined distal location is located between about 50% and 100% of a length of the designated vessel, measured from a proximal end of the designated vessel.

Clause 25. The method of Clause 21, wherein the predetermined distal location is proximal to a distal end of the designated vessel.

Clause 26. The method of Clause 21, wherein the predetermined distal location is identified via an icon displayed in connection with the three-dimensional vascular model.

Clause 27. The method of Clause 26, wherein the icon allows for the predetermined distal location to be adjustable along the designated vessel.

Clause 28. The method of Clause 26, wherein the icon restricts the predetermined distal location to be static along the designated vessel.

Clause 29. The method of Clause 21, wherein the predetermined distal location is based on one or more geometric characteristics, wherein the one or more geometric characteristic includes a target diameter of the designated vessel.

Clause 30. The method of Clause 21, wherein the predetermined distal location is based on a combination of a target distance along the designated vessel and one or more geometric characteristics, wherein the one or more geometric characteristic includes a target diameter of the designated vessel.

Clause 31. The method of Clause 21, wherein the designated vessel is automatically selected.

Clause 32. The method of Clause 21, wherein the designated vessel is manually selected.

Clause 33. The method of Clause 21, wherein the flow value index for the designated location is displayed above the flow value index for a predetermined distal location along a length of the designated vessel.

Clause 34. A system comprising: a non-transitory data store storing computer-executable instructions; and a processor in communication with the non-transitory data store, wherein the computer-executable instructions, when executed by the processor, cause the processor to: receive a plurality of medical images imaging a portion of a vasculature of a subject, wherein the portion of the vasculature comprises one or more vessels; produce, by automatic processing of the medical images, a three-dimensional vascular model of the portion of the vasculature comprising the one or more vessels based on the medical images; calculate flow index values quantifying vascular function along each of the one or more vessels based on the three-dimensional vascular model; display a representation of the three-dimensional vascular model comprising the one or more vessels; and for a designated vessel of the one or more vessels, simultaneously display the flow value index for a designated location of the designated vessel along with the flow value index for a predetermined distal location along a length of the designated vessel.

Clause 35. The system of Clause 34, wherein the predetermined distal location is 80% of a length of the designated vessel.

Clause 36. The system of Clause 34, wherein the predetermined distal location is located between about 50% and 100% of a length of the designated vessel, measured from a proximal end of the designated vessel.

Clause 37. The system of Clause 34, wherein the predetermined distal location is proximal to a distal end of the designated vessel.

Clause 38. The system of Clause 34, wherein the predetermined distal location is identified via an icon displayed in connection with the three-dimensional vascular model.

Clause 39. The system of Clause 38, wherein receipt of user input to adjust the icon causes adjustment of the predetermined distal location along the designated vessel.

Clause 40. The system of Clause 38, wherein the icon is static.

Clause 41. A method comprising: presenting a cardiac analysis on a user interface; receiving, on the user interface, user input to display at least one QR code configured to share the cardiac analysis; in response to the input, generating the at least one QR code which encodes at least a portion of the cardiac analysis and removes protected health information (PHI), wherein the portion includes one or more of a screenshot or a report associated with the cardiac analysis; and displaying the at least one QR code on the user interface.

Clause 42. The method of Clause 41, wherein displaying the at least one QR code on the user interface further comprises displaying an animated QR code, wherein the animated QR code alternates a displayed QR code by sequentially cycling through a plurality of QR codes.

Clause 43. The method of Clause 41, wherein displaying the at least one QR code on the user interface further comprises displaying a series of QR codes, wherein the series of QR codes includes two or more of the at least one QR code displayed on the user interface.

Clause 44. The method of Clause 41, wherein displaying the at least one QR code on the user interface further comprises displaying each of the at least one QR code according to threshold frequency.

Clause 45. The method of Clause 44, wherein the threshold frequency is between 5 Hz and 24 Hz.

Clause 46. The method of Clause 41, further comprising, in response to a mobile device capturing the at least one QR code, causing transfer of data to the mobile device.

Clause 47. The method of Clause 46, further comprising causing transfer of the data relating to the cardiac analysis with removed PHI to the mobile device.

Clause 48. The method of Clause 41, further comprising generating the at least one QR code that encodes: log data, the one or more screenshots, and the one or more reports, wherein the log data includes medical device network performance, wherein the one or more screenshots include redacted medical information of a patient, and wherein the one or more reports include medical diagnostic information regarding the patient.

Clause 49. The method of Clause 48, further comprising in response to a mobile device capturing the at least one QR code, causing transfer of data relating to the log data, the one or more screenshots, and the one or more reports to the mobile device.

Clause 50. The method of Clause 41, wherein the cardiac analysis is an interactive cardiac analysis responsive to user input, and wherein the method further comprises: causing presentation, via a user device based on the QR code, of the interactive cardiac analysis, wherein the interactive cardiac analysis is responsive to user input received via the user device.

Clause 51. A system comprising: a non-transitory data store storing computer-executable instructions; and a processor in communication with the non-transitory data store, wherein the computer-executable instructions, when executed by the processor, cause the processor to: present a cardiac analysis on a user interface; receive, on the user interface, an input to display at least one QR code to share the cardiac analysis; in response to the input, generate the at least one QR code that encodes at least a portion of the cardiac analysis and removes protected health information (PHI); and display the at least one QR code on the user interface.

Clause 52. The system of Clause 51, wherein the computer-executable instructions, when executed by the processor, cause the processor to display an animated QR code, wherein the animated QR code alternates a displayed QR code by sequentially cycling through a plurality of QR codes.

Clause 53. The system of Clause 51, wherein the computer-executable instructions, when executed by the processor, cause the processor to display a series of QR codes, wherein the series of QR codes includes two or more of the at least one QR code displayed on the user interface.

Clause 54. The system of Clause 51, wherein the computer-executable instructions, when executed by the processor, cause the processor to display each of the at least one QR code according to threshold frequency.

Clause 55. The system of Clause 54, wherein the threshold frequency is between 5 Hz and 24 Hz.

Clause 56. The system of Clause 51, wherein the computer-executable instructions, when executed by the processor, cause the processor to, in response to a mobile device capturing the at least one QR code, cause transfer of data to the mobile device.

Clause 57. The system of Clause 56, wherein the computer-executable instructions, when executed by the processor, cause the processor to cause transfer of the data relating to the cardiac analysis with removed PHI to the mobile device.

Clause 58. The system of Clause 51, wherein the computer-executable instructions, when executed by the processor, cause the processor to generate the at least one QR code that encodes at least one of: log data, one or more screenshots, and one or more reports, wherein the log data includes medical device network performance, wherein the one or more screenshots include redacted medical information of a patient, and wherein the one or more reports include medical diagnostic information regarding the patient.

Clause 59. The system of Clause 58, wherein the computer-executable instructions, when executed by the processor, cause the processor to, in response to a mobile device capturing the at least one QR code, cause transfer of data relating to the log data, one or more screenshots, and one or more reports to the mobile device.

Clause 60. One or more non-transitory computer-readable media comprising computer-executable instructions that, when executed by a computing system, cause the computing system to: present a cardiac analysis on a user interface; receive, on the user interface, an input to display at least one QR code to share the cardiac analysis; in response to the input, generate the at least one QR code that encodes at least a portion of the cardiac analysis and removes protected health information (PHI); and display the at least one QR code on the user interface.

Clause 61. The one or more non-transitory computer-readable media of Clause 60, wherein displaying the at least one QR code on the user interface further comprises displaying an animated QR code, wherein the animated QR code alternates a displayed QR code by sequentially cycling through a plurality of QR codes.

Clause 62. The one or more non-transitory computer-readable media of Clause 60, wherein displaying the at least one QR code on the user interface further comprises displaying a series of QR codes, wherein the series of QR codes includes two or more of the at least one QR code displayed on the user interface.

Clause 63. The one or more non-transitory computer-readable media of Clause 60, wherein displaying the at least one QR code on the user interface further comprises displaying each of the at least one QR code according to threshold frequency.

Clause 64. The one or more non-transitory computer-readable media of Clause 63, wherein the threshold frequency is between 5 Hz and 24 Hz.

Clause 65. The one or more non-transitory computer-readable media of Clause 60, further comprising, in response to a mobile device capturing the at least one QR code, causing transfer of data to the mobile device.

Clause 66. The one or more non-transitory computer-readable media of Clause 65, further comprising causing transfer of the data relating to the cardiac analysis with removed PHI to the mobile device.

Clause 67. The one or more non-transitory computer-readable media of Clause 60, further comprising generating the at least one QR code that encodes at least one of: log data, one or more screenshots, and one or more reports, wherein the log data includes medical device network performance, wherein the one or more screenshots include redacted medical information of a patient, and wherein the one or more reports include medical diagnostic information regarding the patient.

Clause 68. The one or more non-transitory computer-readable media of Clause 67, further comprising, in response to a mobile device capturing the at least one QR code, causing transfer of data relating to the log data, one or more screenshots, and one or more reports to the mobile device. All of the processes described herein may be embodied in, and fully automated, via software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence or can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and engines described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

As used herein, the term "about" refers to within ±10%.

The terms "comprises", "comprising", "includes", "including", "having", "such as" and their conjugates mean: "including but not limited to".

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical, and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It should be emphasized that many variations and modifications may be made to the above-described embodiments, the elements of which are to be understood as being among other acceptable examples. All such modifications and variations are intended to be included herein within the scope of this disclosure.

What is claimed:

1. A method for vascular assessment comprising:
receiving a plurality of medical images imaging a portion of a vasculature of a subject, wherein the portion of the vasculature comprises one or more vessels;
producing, by automatic processing of the medical images, a three-dimensional vascular model of the portion of the vasculature comprising the one or more vessels based on the medical images;
calculating flow index values quantifying vascular function along each of the one or more vessels based on the three-dimensional vascular model;
displaying a representation of the three-dimensional vascular model comprising the one or more vessels; and
for a designated vessel of the one or more vessels, simultaneously displaying a first flow index value for a designated location of the designated vessel along with a second flow index value for a predetermined distal location along a length of the designated vessel,
wherein the designated location represents a specific point along the designated vessel identified by an adjustable icon,
wherein the specific point along the designated vessel is associated with a target marker on a pullback curve displayed on a user interface.

2. The method of claim 1, wherein the predetermined distal location is 80% of a length of the designated vessel.

3. The method of claim 1, wherein the predetermined distal location is located at 80% of a length of the designated vessel, measured from a proximal end of the designated vessel.

4. The method of claim 1, wherein the predetermined distal location is located between about 50% and 100% of a length of the designated vessel, measured from a proximal end of the designated vessel.

5. The method of claim 1, wherein the predetermined distal location is proximal to a distal end of the designated vessel.

6. The method of claim 1, wherein the predetermined distal location is identified via an icon displayed in connection with the three-dimensional vascular model.

7. The method of claim 6, wherein the icon allows for the predetermined distal location to be adjustable along the designated vessel.

8. The method of claim 6, wherein the icon restricts the predetermined distal location to be static along the designated vessel.

9. The method of claim 1, wherein the predetermined distal location is based on one or more geometric characteristics, wherein the one or more geometric characteristic includes a target diameter of the designated vessel.

10. The method of claim 1, wherein the predetermined distal location is based on a combination of a target distance along the designated vessel and one or more geometric characteristics, wherein the one or more geometric characteristic includes a target diameter of the designated vessel.

11. The method of claim 1, wherein the designated vessel is automatically selected.

12. The method of claim 1, wherein the designated vessel is manually selected.

13. The method of claim 1, wherein the flow value index for the designated location is displayed above the flow value index for a predetermined distal location along a length of the designated vessel.

14. A system comprising:
a non-transitory data store storing computer-executable instructions; and
a processor in communication with the non-transitory data store, wherein the computer-executable instructions, when executed by the processor, cause the processor to:
receive a plurality of medical images imaging a portion of a vasculature of a subject, wherein the portion of the vasculature comprises one or more vessels;
produce, by automatic processing of the medical images, a three-dimensional vascular model of the portion of the vasculature comprising the one or more vessels based on the medical images;
calculate flow index values quantifying vascular function along each of the one or more vessels based on the three-dimensional vascular model;
display a representation of the three-dimensional vascular model comprising the one or more vessels; and
for a designated vessel of the one or more vessels, simultaneously display a first flow index value for a designated location of the designated vessel along with a second flow index value for a predetermined distal location along a length of the designated vessel,
wherein the designated location represents a specific point along the designated vessel identified by an adjustable icon,
wherein the specific point along the designated vessel is associated with a target marker on a pullback curve displayed on a user interface.

15. The system of claim 14, wherein the predetermined distal location is 80% of a length of the designated vessel.

16. The system of claim 14, wherein the predetermined distal location is located between about 50% and 100% of a length of the designated vessel, measured from a proximal end of the designated vessel.

17. The system of claim 14, wherein the predetermined distal location is proximal to a distal end of the designated vessel.

18. The system of claim 14, wherein the predetermined distal location is identified via an icon displayed in connection with the three-dimensional vascular model.

19. The system of claim 18, wherein receipt of user input to adjust the icon causes adjustment of the predetermined distal location along the designated vessel.

20. The system of claim 18, wherein the icon is static.

* * * * *